(12) United States Patent
Pantoliano et al.

(10) Patent No.: US 6,569,631 B1
(45) Date of Patent: *May 27, 2003

(54) MICROPLATE THERMAL SHIFT ASSAY FOR LIGAND DEVELOPMENT USING 5-(4"-DIMETHYLAMINOPHENYL)-2-(4'-PHENYL) OXAZOLE DERIVATIVE FLUORESCENT DYES

(75) Inventors: Michael W. Pantoliano, Avondale, PA (US); Eugenio C. Petrella, Wayne, PA (US); F. Raymond Salemme, Yardley, PA (US); Barry A. Springer, Wilmington, DE (US)

(73) Assignee: 3-Dimensional Pharmaceuticals, Inc., Yardley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/438,357

(22) Filed: Nov. 12, 1999

Related U.S. Application Data

(60) Provisional application No. 60/108,085, filed on Nov. 12, 1998.

(51) Int. Cl.[7] .......................... G01N 33/53; G01N 21/76
(52) U.S. Cl. .............................. 435/7.1; 435/7.4; 435/4; 435/DIG. 1; 435/DIG. 14; 435/DIG. 41; 436/172; 436/501; 436/518
(58) Field of Search .............................. 435/4, 7.1, 7.4, 435/DIG. 1, DIG. 12, DIG. 41, DIG. 14; 436/501, 518, 172

(56) References Cited

U.S. PATENT DOCUMENTS

| | | | |
|---|---|---|---|
| 4,580,895 A | 4/1986 | Patel | 356/39 |
| 4,626,684 A | 12/1986 | Landa | 250/328 |
| 4,628,026 A | 12/1986 | Gardell et al. | 435/7 |
| 4,774,055 A | 9/1988 | Wakatake et al. | 422/64 |
| 4,778,763 A | 10/1988 | Makiguchi et al. | 436/47 |
| 4,859,609 A | 8/1989 | Dull et al. | 436/501 |
| 4,963,263 A | 10/1990 | Kauvar | 210/635 |
| 5,096,807 A | 3/1992 | Leaback | 435/6 |
| 5,133,866 A | 7/1992 | Kauvar | 210/635 |
| 5,200,504 A | 4/1993 | Ghadiri | 530/304 |
| 5,217,869 A | 6/1993 | Kauvar | 435/7.9 |
| 5,255,976 A | 10/1993 | Connelly | 374/31 |
| 5,260,207 A | 11/1993 | Pantoliano et al. | 435/221 |
| 5,290,513 A | 3/1994 | Berthold et al. | 422/52 |
| 5,300,425 A | 4/1994 | Kauvar | 435/7.9 |
| 5,314,825 A | 5/1994 | Weyrauch et al. | 436/43 |
| 5,324,635 A | 6/1994 | Kawase et al. | 435/7.94 |
| 5,325,295 A | 6/1994 | Fratantoni et al. | 364/413.08 |
| 5,338,659 A | 8/1994 | Kauvar et al. | 435/7.1 |
| 5,340,747 A | 8/1994 | Eden | 436/172 |
| 5,355,215 A | 10/1994 | Schroeder et al. | 356/317 |
| 5,356,784 A | 10/1994 | Kauvar | 435/7.9 |
| 5,383,023 A | 1/1995 | Walleczek | 356/417 |
| 5,409,611 A | 4/1995 | Kauvar | 210/635 |
| 5,415,839 A | 5/1995 | Zaun et al. | 422/64 |
| 5,436,718 A | 7/1995 | Fernandes et al. | 356/73 |
| 5,463,564 A | 10/1995 | Agrafiotis et al. | 364/496 |
| 5,496,519 A | 3/1996 | Schacher | 422/64 |

(List continued on next page.)

FOREIGN PATENT DOCUMENTS

| | | |
|---|---|---|
| EP | 0 512 334 B1 | 11/1992 |
| EP | 0 613 007 A2 | 8/1994 |
| EP | 0 640 828 A1 | 3/1995 |
| EP | 0 770 876 A1 | 5/1997 |
| WO | WO 92/03542 A1 | 3/1992 |
| WO | WO 93/14781 | 8/1993 |
| WO | WO 94/05394 | 3/1994 |
| WO | WO 95/18969 | 7/1995 |
| WO | WO 96/23879 | 8/1996 |
| WO | WO 97/09342 | 3/1997 |
| WO | WO 97/14038 | 4/1997 |
| WO | WO 97/20952 | 6/1997 |
| WO | WO 97/42500 | 11/1997 |
| WO | WO 98/15969 A2 | 4/1998 |
| WO | WO 98/39484 | 9/1998 |
| WO | WO 98/15969 A3 | 7/2000 |

OTHER PUBLICATIONS

Bergdoll, M., et al., "All in the family: Structural and evolutionary relationships among three modular proteins with diverse functions and variable assembly," *Protein Sci.* 7:1661–1670, Cambridge University Press (Aug. 1998).

Blattner, F.R., et al., "The Complete Genome Sequence of *Escherichia coli* K–12," *Science* 277:1453–1462, American Association for the Advancement of Science (Sep. 1997).

Bowie, J.U. and Sauer, R.T., "Equilibrium Dissociation and Unfolding of the Arc Repressor Dimer," *Biochem.* 28:7139–7143, American Chemical Society (1989).

(List continued on next page.)

*Primary Examiner*—Padmashri Ponnaluri
(74) *Attorney, Agent, or Firm*—Sterne, Kessler, Goldstein & Fox P.L.L.C.

(57) ABSTRACT

The present invention provides a method for ranking the affinity of each of a multiplicity of different molecules for a target molecule which is capable of unfolding due to a thermal change. The method comprises (a) contacting the target molecule with one molecule of a multiplicity of different molecules, in the presence of a 5-(4"-dimethylaminopheny-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to the thermal unfolding information for the target molecule in the absence of any of the molecules in the multiplicity of different molecules; and (f) ranking the affinities of each of the molecules according to the difference in the thermal unfolding information between the target molecule in each of the containers and the target molecule in the absence of any of the molecules in the multiplicity of different molecules.

12 Claims, 43 Drawing Sheets

U.S. PATENT DOCUMENTS

| | | | |
|---|---|---|---|
| 5,506,097 A | 4/1996 | Potter et al. | 435/4 |
| 5,525,300 A | 6/1996 | Danssaert et al. | 422/99 |
| 5,557,398 A | 9/1996 | Wechsler et al. | 356/318 |
| 5,567,317 A | 10/1996 | Kauvar | 210/635 |
| 5,585,277 A | 12/1996 | Bowie et al. | 436/518 |
| 5,587,293 A | 12/1996 | Kauvar et al. | 435/7.21 |
| 5,589,351 A | 12/1996 | Harootunian | 435/29 |
| 5,599,504 A | 2/1997 | Hosoi et al. | 422/82.08 |
| 5,620,901 A | 4/1997 | Kauvar | 436/518 |
| 5,631,734 A | 5/1997 | Stern et al. | 356/317 |
| 5,679,582 A | 10/1997 | Bowie et al. | 436/518 |
| 6,020,141 A | 2/2000 | Pantoliano et al. | 435/7.1 |
| 6,036,920 A | 3/2000 | Pantoliano et al. | 422/67 |
| 6,214,293 B1 | 4/2001 | Pantoliano et al. | 422/67 |
| 6,232,085 B1 | 5/2001 | Pantoliano et al. | 435/7.1 |
| 6,268,158 B1 | 7/2001 | Pantoliano et al. | 435/7.1 |
| 6,268,218 B1 | 7/2001 | Pantoliano et al. | 436/86 |
| 6,291,192 B1 | 9/2001 | Pantoliano et al. | 435/7.1 |
| 6,303,322 B1 | 10/2001 | Pantoliano et al. | 435/7.1 |

OTHER PUBLICATIONS

Chen, L., et al., "Microtiter Plate Binding Assay for Cholinergic Compounds Utilizing the Nicotinic Acetylcholine Receptor," *Anal. Chem. 64:*3018–3023, American Chemical Society (1992).

Denessiouk, K.A., et al., "Enzyme–mononucleotide interactions: Three different folds share common structural elements for ATP recognition," *Protein Sci. 7:*1768–1771, Cambridge University Press (Aug. 1998).

Dennis, S., et al., "Use of fragments of hirudin to investigate thrombin–hirudin interaction," *Eur. J. Biochem. 188:*61–66, Springer International (1990).

Fraser, C.M., et al., "Complete Genome Sequence of *Treponema pallidum,* the Syphilis Spirochete," *Science 281:*375–388, American Association for the Advancement of Science (Jul. 1998).

Friguet, B., et al., "Immunochemical analysis of protein conformation," in: *Protein Structure: A Practical Approach,* Creighton, T.E., ed., IRL Press at Oxford University Press, Oxford, England, pp. 287–310 (1989).

Grant, S.K., et al., "Use of Protein Unfolding Studies to Determine the Conformational and Dimeric Stabilities of HIV–1 and SIV Proteases," *Biochem. 31:*9491–9501, American Chemical Society (1992).

Haff, L.A., et al., "A High–Performance System for Automation of the Polymerase Chain Reaction," *BioTechniques 10:*102–103, 106–112, Eaton Publishing Co. (1991).

Harrington, J.P., "Spectroscopic Analysis of the Unfolding of Transition Metal–Ion Complexes of Human Lactoferrin and Transferrin," *Int. J. Biochem. 24:*275–280, Pergamon Press (1992).

Herrero, M.E. and Castell, J.V., "Fluorometric Microassay to Quantify Microsomal Epoxide Hydrolase in 96–Well Plates," *Anal. Biochem. 230:*154–158, Academic Press Inc. (1995).

Hieter, P. and Boguski, M., "Functional Genomics: It's All How You Read It," *Science 278:*601–602, American Association for the Advancement of Science (Oct. 1997).

Higuchi, R., et al., "Simultaneous Amplification and Detection of Specific DNA Sequences," *Bio/Technology 10:*413–417, Nature Publishing Co. (1992).

Higuchi, R., et al., "Kinetic PCR Analysis: Real–time Monitoring of DNA Amplification Reactions," *Bio/Technology 11:*1026–1030, Nature Publishing Co. (1993).

Hogg, P.J. and Jackson, C.M., "Fibrin monomer protects thrombin from inactivation by heparin–antithrombin III: Implications for heparin efficacy," *Proc. Natl. Acad. Sci. USA 86:*3619–3623, National Academy of Sciences (1989).

Hogg, P.J. and Jackson, C.M., "Formation of a Ternary Complex between Thrombin, Fibrin Monomer, and Heparin Influences the Action of Thrombin on Its Substrates," *J. Biol. Chem. 265:*248–255, American Society for Biochemistry and Molecular Biology, Inc. (1990).

Hotchkiss, K.A., et al., "Inhibition of Heparin Activity in Plasma by Soluble Fibrin: Evidence for Ternary Thrombin–Fibrin–Heparin Complex Formation," *Blood 84:*498–503, W.B. Saunders Company (1994).

Janknecht, R., et al., "Rapid and efficient purification of native histidine–tagged protein expressed by recombinant vaccinia virus," *Proc. Natl. Acad. Sci. USA 88:*8972–8976, National Academy of Sciences (1991).

Kan, M., et al., "An Essential Heparin–Binding Domain in the Fibroblast Growth Factor Receptor Kinase," *Science 259:*1918–1921, American Association for the Advancement of Science (1993).

Kenndey, M.W., et al., "The ABA–1 Allergen of the Parasitic Nematode Ascaris suum: Fatty Acid and Retinoid Binding Function and Structural Characterization," Biochem. 34:6700–6710, American Chemical Society (1995).

Kikuchi, T., et al., "Measurement of Chemiluminescence from Neutrophils in a 96–Well Microplate using Lumi Box U–800 II," *J. Biolum. Chemilum. 12:*149–153, John Wiley & Sons, Ltd. (May 1997).

Lewis, M., et al., "Crystal Structure of the Lactose Operon Repressor and Its Complexes with DNA and Inducer," *Science 271:*1247–1254, American Association for the Advancement of Science (1996).

Mach, H., et al., "Effect of Polyanions on the Folding and Unfolding of Acidic Fibroblast Growth Factor," in: Harnessing Biotechnology for the 21st Century. Proceedings of the Ninth International Biotechnology Symposium and Exposition, Ladisch, M.R. and Bose, A., eds., American Chemical Society, Washington, DC, pp. 290–293 (1992).

Mach, H., et al., "Nature of the Interaction of Heparin with Acidic Fibroblast Growth Factor," *Biochem 32:*5480–5489, American Chemical Society (1993).

Mach, H., et al., "Partially Structured Self–Associating States of Acidic Fibroblast Growth Factor," *Biochem 32:*7703–7711, American Chemical Society (1993).

Mansfield, E.S., et al., "Nucleic acid detection using nonradioactive labeling methods," *Mol. Cell. Probes 9:*145–156, Academic Press Ltd. (1995).

Marquis–Omer, D., et al., "Stabilization of the FK506 Binding Protein by Ligand Binding," *Biochem. Biophys. Res. Commun. 179:*741–748, Academic Press, Inc. (1991).

Martin, C.S. and Bronstein, I., "Imaging of Chemiluminescent Signals with Coo CCD Camera Systems," *J. Biolum. Chemilum 9:*148–183, John Wiley & Sons, Ltd. (1994).

Middaugh, C.R., et al., "Nature of the Interaction of Growth Factors with Suramin," *Biochem. 31:*9016–9024, American Chemical Society (1992).

Middaugh, C.R., et al., "Selected Problems in the Formulation of Protein Pharmaceuticals," *Book of Abstracts of the 205th ACS National Meeting, Abstract No. 126,* American Chemical Society (1993).

Milligan, G., et al., "$G_{16}$ as a universal G protein adapter: implications for agonist screening strategies," *Trend Pharm. Sci. 17:*235–237, Elsevier Science Ltd. (1996).

Nakatani, H., et al., "Temperature–jump Studies on Benzeneboronic Acid–Serince Protease Interactions," *J. Biochem.* 77:905–908, The Japanese Biochemical Society (1975).

Nilsson, B., "Proper and Improper Folding of Proteins in the Cellular Environment," *Annu. Rev. Microbiol.* 45:607–635, Annual Reviews, Inc. (1991).

Pace, C.N. and Marshall, H.F., Jr., "A Comparison of the Effectiveness of Protein Denaturants for β–Lactoglobulin and Ribonuclease," *Arch. Biochem. Biophys.* 199:270–276, Academic Press, Inc. (1980).

Pakula, A.A., "A Genetic and Biochemical Analysis of the Bacteriophage λ Cro Protein," *Doctoral Thesis*, Department of Biology, Massachusetts Institute of Technology (1988).

Pakula, A.A. and Sauer, R.T., "Genetic Analysis of Protein Stability and Function," *Annu. Rev. Genet.* 23:289–310, Annual Reviews Inc. (1989).

Pakula, A.A. and Sauer, R.T., "Amino Acid Substitutions That Increase the Thermal Stability of the λ Cro Protein," *Proteins: Struct. Funct. Genet.* 5:202–210, Alan R. Liss, Inc. (1989).

Pan, P., "β–Site Covalent Reactions Trigger Transitions between Open and Closed Conformations of the Tryptophan Synthase Bienzyme Comples," *Biochem* 35:5002–5013 American Chemical Society (1996).

Pantoliano, M.W., et al., "Multivalent Ligand–Receptor Binding Interactions in the Fibroblast Growth Factor System Produce a Cooperative Growth Factor and Heparin Mechanism for Receptor Dimerization," *Biochem.* 33:10229–10248, American Chemical Society (1994).

Pennisi, E., "Laboratory Workhorse Decoded," *Science* 277:1432–1434, American Association for the Advancement of Science (Sep. 1997).

Qasba, P.K. and Kumar, S., Molecular Divergence of Lysozymes and α–Lactalbumi *Crit. Rev. Biochem. Mol. Biol.* 32:255–306, CRC Press LLC (Dec. 1997).

Ramm, P., "Imaging systems in assay screening," *Drug Disc. Today* 4:401–410, Elsevier Science Ltd. (Sep. 1999).

Ramsay, G. and Eftink, M.R., "A Multidimensional Spectorphotometer for Monito Thermal Unfolding Transitions of Macromolecules," *Biophys. J.* 31:516–523, The Biophysical Society (1994).

Randall, L.L., "Peptide Binding by Chaperone SecB: Implications for Recognition of Nonnative Structure," *Science* 257:241–245, American Association for the Advancement of Science (1992).

Rosengart, T.K., et al., "Heparin Protects Heparin–Binding Growth Factor–I from Proteolytic Inactivation In Vitro," *Biochem. Biophys. Res. Commun.* 152:432–440, Academic Press, Inc. (1988).

Rowen, L., et al., "Sequencing the Human Genome," *Science* 278:605–607, American Association for the Advancement of Science (Oct. 1997).

Sackett, D.L., et al., "Local Unfolding and the Stepwise Loss of the Functional Properties of Tubulin," *Biochem.* 33:12868–12878, American Chemical Society (1994).

Tanigaki, N., et al., "Unfolding HLA Class I α Chains and Their Use in an Assay of HLA Class–I–Peptide Binding," *Hum. Immunol.* 36:119–127, Elsevier Science (1993).

Tapparelli, C., et al., "In Vitro and In Vivo Characterization of a Neutral Boron–containing Thrombin Inhibitor," *J. Biol. Chem.* 268:4734–4741, American Society for Biochemistry and Molecular Biology, Inc. (1993).

Tatusov, R.L., et al., "A Genomic Perspective on Protein Families," *Science* 278:631–637, American Association for the Advancement of Science (Oct. 1997).

Tong, L., et al., "Conserved mode of peptidomimetic inhibition and substrate recognition of human cytomegalovirus protease," *Nature Structural Biol.* 5:819–826, Nature Publishing Co. (Sep. 1989).

Vijayalakshim, J., et al., "The isomorphous structures of prethrombin2, hirugen–and PPACK–thrombin: Changes accompanying activation and exosite binding to thrombin," *Protein Sci.* 3:2254–2271, Cambridge University Press (1994).

Volkin, D.B. and Klibanov, A.M., "Mechanism of Thermoinactivation of Immobilized Glucose Isomerase," *Biotech. Bioengin.* 33:1104–1111, John Wiley & Sons, Inc. (1989).

Volkin, D.B., et al., "Sucralfate and soluble sucrose octasulfate bind and stabilize acidic fibroblast growth factor," *Biochim. Biophys. Acta.* 1203:18–26, Elsevier Science Publishers B.V. (1993).

Waring, M.J., "Stabilization of Two–Stranded Ribohomopolymer Helices and Destabilization of a Three–Stranded Helix by Ethidium Bromide," *Biochem. J.* 143:483–486, The Biochemical Society (1974).

Wiseman, T., et al., "Rapid Measurement of Binding Constants and Heats of Binding Using a New Titration Calorimeter," *Anal. Biochem.* 179:131–137, Academic Press Inc. (1989).

Bagshaw, C.R. and Harris, D.A., "Chapter 4. Measurement of Ligand Binding to Proteins," in *Spectrophotometry & spectrofluorimetry: a practical approach*, Bashford, C.L. and Harris, D.A., Eds., IRL Press, Washington, DC, pp. 91–113 (1987).

Barcelo, F., et al., "A Scanning Calorimetric Study of Natural DNA and Antitumoral Anthracycline Antibiotic–DNA Complexes," *Chem.–Biol. Interactions* 74:315–324, Elsevier Scientific Publishers Ireland Ltd. (1990).

Becktel. W.J., et al., "Protein Stability Curves," *Biopolymers* 26:1859–1877, John Wiley & Sons, Inc. (1987).

Belevitch, G.V., et al., "Calcium antagonists, riodipin, niphedipine and verapamil, binding to model and biological membranes; fluorescence analysis," *Biologicheskie Membrany* 5:768–776, Rossiiskaya Akademiya Nauk (1988).

Bell, J.E., "Chapter 4. Fluorescence; Solution Studies," in *Spectrometry in Biochemistry*, vol. I, Bell, J.E., ed., CRC Press, Inc., Boca Raton, FL, pp. 155–194 (1981).

Bone, R., et al., "Inhibition of Thymidine Kinase by $P^1$–(Adenosine–5')–$P^5$–(thymidine–5')–pentaphosphate," *J. Biol. Chem.* 261:5731–5735, The American Society of Biological Chemists, Inc. (1986).

Bouvier, M. and Wiley, D.C., "Importance of Peptide Amino and Carboxyl Termini to the Stability of MHC Class I Molecules," *Science* 265:398–402, American Association for the Advancement of Science (1994).

Brand, L. and Gohlke, J.R., "Fluorescence Probes for Structure," *Ann. Rev. Biochem.* 41:843–868, Annual Reviews Inc. (1972).

Brandts, J.F. and Lin. L.–N., "Study of Strong to Ultratight Protein Interactions Using Differential Scanning Calorimetry," *Biochem.* 29:6927–6940, American Chemical Society (1990).

Brandts, J.F., et al., "An instrument for rapid determination of binding constants for biomolecules," *Am. Lab. 22:*30–41, International Scientific Communications, Inc. (1990).

Buchner, J., et al., "Alternatively Folded States of an Immunoglobulin," *Biochem. 30:*6922–6929, American Chemical Society (1991).

Burke, C.J., et al., "Effect of Polyanions on the Unfolding of Acidic Fibroblast Growth Factor," *Biochem. 32:*6419–6426, American Chemical Society (1993).

Butour, J.–L., et al., "Effect of the amine non–leaving group on the structure and stability of DNA complexes with cis–[Pt(R–NH$_2$)$_2$(NO$_3$)$_2$]," *Eur. J. Biochem. 202:*975–980, Springer International (1991).

Chavan, A.J., et al., "Interaction of Nucelotides With Acidic Fibroblast Growth Factor (FGF–1)," *Biochem. 33:*7193–7202, American Chemical Society (1994).

Clegg, R.M., et al., "Observing the helical geometry of double–stranded DNA in solution by fluorescence resonance energy transfer," *Proc. Natl. Acad. Sci. USA 90:*2994–2998, The National Academy of Sciences of the USA (1993).

Copeland, R.A., et al., "The Structure of Human Acidic Fibroblast Growth Factor and Its Interaction with Heparin," *Arch. Biochem. Biophys. 289:*53–61, Academic Press, Inc. (1991).

Cox, M.J. and Weber, P.C., "An Investigation of Protein Crystallization Parameters Using Successive Automated Grid Searches (SAGS)," *J. Crystal Growth 90:*318–324, Elsevier Science Publishers B.V. (1988).

Darzynkiewicz, Z., et al., "DNA Denaturation In Situ: Effect of Divalent Cations and Alcohols," *J. Cell Biol. 68:*1–10, The Rockefeller University Press (1976).

Davidson, A.R., et al., "Cooperatively folded proteins in random sequence libraries," *Nature Struct. Biol. 2:*856–864, Macmillan Magazines Ltd. (Oct. 1995).

Diwu, Z., et al., "Fluorescent Molecular Probes II. The Synthesis, Spectral Properties and Use Fluorescent Solvatochromic Dapoxyl™ Dyes," *Photochem. Photobiol. 66:*424–431, American Society Photobiology (Oct. 1997).

Draper, D.E. and Gluick, T.C., "Melting Studies of RNA Unfolding and RNA–Ligand Interactions," *Meth. Enzymol. 259:*281–305, Academic Press, Inc. (Sep. 1995).

Eftink, M.R., "The Use of Fluorescent Method to Monitor Unfolding Transitions in Proteins," *Biophys. J. 66:*482–501, Biophysical Society (1994).

Elwell, M. and Schellman, J., "Phage T4 Lysozyme Physical Propeties and Reversible Unfolding," *Biochim. Biophys. Acta 386:*309–323, Elsevier Scientific Publishing Company, Amsterdam (1975).

Elwell, M.L. and Schellman, J.A., "Stability of Phage T4 Lysozymes. I. Native Properties and Thermal Stability of Wild Type and Two Mutants Lysozymes," *Biochim. Biophys. Acta 494:*367–383, Elsevier/North–Holland Biomedical Press (1977).

Eriksson, A.E., et al., "Similar Hydrophobic Replacements of Leu99 and Phe153 within the Core of T4 Lysozyme Have Different Structural and Thermodynamic Consequences," *J. Mol. Biol. 229:*747–769, Academic Press Ltd. (1993).

Freire, E., "Thermal Denaturation Methods in the Study of Protein Folding," *Meth. Enzymol. 259:*144–168, Academic Press, Inc. (1995).

Fukada, H., "Calorimetry of the Ligand Binding to Proteins," *Tanpakushitsu Kakusan Koso 33:*328–336, Kyoritsu Shuppan Co. Ltd. (1988).

Gordon, E.M., et al., "Applications of Combinatorial Technologies to Drug Discovery. 2. Combinatorial Organic Synthesis, Library Screening Strategies, and Future Directions," *J. Med. Chem. 37:*1385–1401, American Chemical Society (1994).

Green, S.N., et al., "Roles of Metal Ions in the Maintenance of the Tertiary and Quaternary Structure of Arginase from *Saccharomyces cerevisiae,*" *J. Biol. Chem. 266:*21474–21481, American Society for Biochemistry and Molecular Biology (1991).

Hanna, M. and Szostak, J.W., Supression of mutations in the core of the Tetrahymena ribozyme spermidine, ethanol and by substrate stabilization, *Nucl. Acids Res. 22:*5326–5331 Oxford University Press (1994).

Hei, D.J. and Clark, D.S., "Estimation of Melting Curves From Enzymatic Activity–Temperature Profiles," *Biotechnol. Bioeng. 42:*1245–1251, John Wiley & Sons, Inc. (1993).

Hofmann, A., et al., "A Sparse Matrix Screen to Establish Initial Conditions for Protein Renaturation," *Anal. Biochem. 230:*8–15, Academic Press, Inc. (1995).

Hutton, J.R., "Renaturation kinetics and thermal stability of DNA in aqueous solutions of formamide and urea," *Nucl. Acids Res. 4:*3537–3555, Oxford University Press (1977).

Iida, K., "Structure and biological activity of complement receptors CR1, CR2 and CR3," *Seikagaku 58:*1471–1474, Nihon Seikagakkai (1986).

Jensen, D.E., and von Hippel, P.H., "DNA 'Melting' Proteins: I. Effects of Bovine pancreatic ribonuclease binding on the conformation and stability of DNA," *J. Biol. Chem. 251:*7198–7214, American Society of Biological Chemists, Inc. (1976).

Johnson, C.M., et al., "Differential Scanning Calorimetry of Thermal Unfolding of the Methionine Repressor Protein (MetJ) from *Escherichia coli,*" *Biochem. 31:*9717–9724, American Chemical Society (1992).

Kogtev, L.S., et al., "Use of fluorescein–labeled lipid probes for analyzing Substance P and its derivatives binding to the rat brain tachykinin receptors," *Biologicheskie Membrany 6:*34–41, Rossiiskaya Akademiya Nauk (1989).

Kuroki, R. and Inaka, K., "Stabilization of a Protein by Constructing a Ligand Binding Site," *Tanpakushitsu Kakusan Koso 37:*314–321, Kyoritsu Shuppan Co. Ltd. (1992).

Kuwajima, K., "Kinetic pathway of globular–protein folding," *Seikagaku 62:*117–121, Nihon Seikagakkai (1990).

Lapadat, M.A. and Spremulli, L.L., "Effect of Guanine Nucleotides on the Conformation and Stability of Chloroplast Elongation Factor Tu," *J. Biol. Chem. 264:*5510–5514, American Society for Biochemistry and Molecular Biology, Inc. (1989).

Lee, M., et al., "In Vitro Cytotoxicity of GC Sequence Directed Alkylating Agents Related to Distamycin," *J. Med. Chem. 36:*863–870, American Chemical Society (1993).

Lennick, M., et al., "Changes in Protein Conformation and Stability Accompany Complex Formation Between Human C1 Inhibitor and Cls," *Biochem. 24:*2561–2568, American Chemical Society (1985).

Lin, L.–N., et al., "Calorimetric Studies of Serum Transferrin and Ovotransferrin. Estimates of Domain Interactions, and Study of the Kinetic Complexities of Ferric Ion Binding," *Biochem. 33:*1881–1888, American Chemical Society (1994).

Ma, C.-Y. and Harwalkar, V.R., "Effects of Medium and Chemical Modification on Thermal Characteristics of β-lactoglobulin," *J. Thermal Analysis 47*:1513–1525, John Wiley & Sons, Ltd. (Jan. 1996).

Manevich, E.M., et al., "The binding of the B-chain of ricin to Burkitt lymphoma cells," *FEBS Lett. 194*:313–316, Elsevier Science Publishers B.V. (1986).

Markovic–Housley, Z. and Garavito, R.M., "Effect of temperature and low pH on structure and stability of matrix porin and micellar detergent solutions," *Biochim. Biophys. Acta 869*:158–170, Elsevier Science Publishers B.V. (1986).

Merabet, E.K., et al., "Differential scanning calorimetric study of 5–enolpyruvoyl shikimate–3–phosphate synthase and its complexes with shikimate–3–phosphate and glyphosphate: irreversible thermal transitions," *Biochim. Biophys. Acta 1161*:272–278, Elsevier Science Publishers B.V. (1993).

Molotskovskaya, I.M., et al., "The concaval in A binding to the plasma membranes of young and old mouse lymphocytes: a fluorescent probe study," *Biologicheskie Membrany 9*:32–39, Rossiiskaya Akademiya Nauk (1991).

Molotkovskaya, I.M., et al., "Immunosuppressive activity of glycosphingolipids: a study of the interaction of interleukin–2 with gangliosides using cells and model systems," *Biologicheskie Membrany 9*:143–151, Rossiiskaya Akademiya Nauk (1992).

Morton, A., et al., "Energetic Origins of Specificity of Ligand Binding in an Interior Nonpolar Cavity of T4 Lysozyme," *Biochem. 34*:8564–8575, American Chemical Society (1995).

Muriana, F.J.G., et al., "Further thermal characterization of an aspartate aminotransferase from a halophilic organisms," *Biochem. J. 298*:465–470, The Biochemical Society, London (1994).

Murray–Brelier, A. and Goldberg, M.E., "A physicalchemical and immunological comparison shows that native and renatured *Escherichia coli* tryptophan synthase $\beta_2$ subunits are identical," *Biochimie 71*:533–543, Editions Scientifique Medicales Elsevier (1989).

Otto, A. and Seckler, R., "Characterization, stability and refolding of recombinant hirudin," *Eur. J. Biochem. 202*:67–73, Springer International (1991).

Pace, C.N. and Grimsley, G.R., "Ribonuclease $T_1$ Is Stabilized by Cation and Anion Binding," *Biochem 27*:3242–3246, American Chemical Society (1988).

Pantoliano, M.W., "Automated Receptor Screening By Thermal Physical Assays," Department of Health and Human Services Small Business Research Program Phase I Grant Application (1995).

Pantoliano, M.W., "Automated Receptor Screening By Thermal Physical Assays," Department of Health and Human Servies Small Business Research Program Phase II Grant Application (1996).

Pantoliano, M.W., "A Miniaturized Thermal Shift Assay Technology for Directly Evaluating Targets Derived from Genomics," poster presented at the Society For Biomolecular Screening Annual Meeting, Baltimore, MD (Sep. 1998).

Petrella, E., "A Miniaturized Thermal Shift Assay Technology for Directly Evaluating Targets Derived from Genomics," poster presented at the Society For Biomolecular Screening Annual Meeting, Edinburgh, Scotland (Sep. 1999).

Pilch, D.S. et al., "Characterization of a Triple Helix–Specific Ligand: BePI {3–methoxy–7H–8–methyl–11–[3'–amino)propylamino]benzo[e]pyrido[4,3–b]indole} Intercalates into Both Double–helical and Triple–helical DNA," *J. Mol. Biol. 232*:926–946, Academic Press Ltd (1993).

Pilch, D.S. and Breslauer, K.J., "Ligand–induced formation of nucleic acid triple helices," *Pro Natl. Acad. Sci. USA 91*:9332–9336, The National Academy of Sciences of the USA (1994).

Pörschke, D. and Jung, M., "Stability decrease of RNA double helices by phenylalanin–, tyrosine–and tryptophane–amides. Analysis in terms of site binding and relation to melting proteins," *Nucl. Acids Res. 10*:6163–6176, Oxford University Press (1982).

Porter, P.N., et al., "Stabilization of $SV_{40}$ transformed human fibroblast cytoplasmic thymidine kinase by ATP," *Mol. Cell. Biochem. 35*:59–64, Martinus Nijhoff/Dr. W. Junk Publishers b.v. (1980).

Privalov, P.L., "Thermal Investigations of Biopolymer Solutions and Scanning Microcalorimetry," *FEBS Lett. 40(Suppl.)*:S140–S153, North–Holland Publishing Company (1974).

Rakhamininova, A.B., et al., "Model for auxin receptor," *Biokhimiya 43*:806–823, Rossiiskaya Akademiya Nauk (1978).

Rakhaminov, A.B., et al., "Construction of a model of the auxin receptor," *Biorak 43*:639–653, Plenum Publishing Corporation (1978).

Ramalingam, K., et al., "Conformational Studies of Anionic Melittin Analogues: Effect of Peptide Concentration, pH, Ionic Strength, and Temperature—Models for Protein Folding and Halophilic Proteins," *Biopolymers 32*:981–992, John Wiley & Sons, Inc. (1992).

Roy, K.B., et al., "Hairpin and Duplex Forms of a Self-Complementary Dodecamer, d–AGATCTAGATCT, and Interaction of the Duplex Form with the Peptide KGWGK: Can a Pentapeptide Destabilize DNA?," *Biochem 31*:6241–6245, American Chemical Society (1992).

Sagar, S.L. and Domach, M.M., "Thermostability of Drifted Oligomeric, Reduced and Refolded Proteins," Chapter 5 in: *ACS Symposium Series: Protein Refolding*, Georgiou, G. and De Bernardez–Clark, E., Eds., American Chemical Society, publ., pp. 64–78, American Chemical Society (1991).

Schellman, J. A., "Macromolecular Binding," *Biopolymers 14*:999–1018, John Wiley & Sons, Inc. (1975).

Schellman, J.A., "The Effect of Binding on the Melting Temperature of Biopolymers," *Biopolymers 15*:999–1000, John Wiley & Sons, Inc. (1976).

Schellman, J.A., "The Thermodynamic Stability of Proteins," *Ann. Rev. Biophys. Chem. 16*:115–137, Annual Reviews Inc. (1987).

Schellman, J.A., "Fluctuation and Linkage Relations in Macromolecular Solution," *Biopolymers 29*:215–224, John Wiley & Sons, Inc. (1990).

Schellman, J.A., "A simple model for solvation in mixed solvents. Applications to the stabilization and destabilization of macromolecular structures," *Biophys. Chem. 37*:121–140, Elsevier Science Publishers B.V. (1990).

Schellman, J.A., "The relation between the free energy of interaction and binding," *Biophys. Chem. 45*:273–279, Elsevier Science Publishers B.V. (1993).

Schellman, J.A., "The Thermodynamics of Solvent Exchange," *Biopolymers* 34:1015–1026, John Wiley & Sons, Inc. (1994).

Schwarz, F.P., et al., "Thermodynamics of the Binding of Galactopyranoside Derivatives to the Basic Lectin from Winged Bean (*Psophocarpus tetrogonolobus*)," *J. Biol. Chem.* 266:24344–24350, American Society for Biochemistry and Molecular Biology, Inc. (1991).

Shchyolkina, A.K., et al., "The R–Form of DNA Does Exist," *FEBS Lett.* 339:113–118, Elsevier Science Publsihers B.V. (1994).

Shrake, A., et al., "Partial Unfolding of Dodecameric Glutamine Synthetase from *Escherichia coli* Temperature––Induced, Reversible Transitions of Two Domains," *Biochem.* 28:6281–6294, American Chemical Society (1989).

Smirnov, O.N., et al., "Study on the Interaction of the cholera toxin and its B–subunit with liposomes containing ganglioside GM1 and fluorescent–labeled gangliosides," *Biologicheskie Membrany* 12:174–184, Rossiiskaya Akademiya Nauk (1995).

Sominsky, V. N., et al., "Using a fluorescent probe for investigating β–adrenoreceptive fun of human erythrocytes," *Biofizika* 30:642–645, Rossiiskaya Akademiya Nauk (1985).

Surin, A.M., et al., "A study of the interaction of cholera toxin B–subunit with liposomes containing ganglioside GM1 and fluorescein–labeled lipids," *Biologicheskie Membrany* 9:495–508, Rossiiskaya Akademiya Nauk (1992).

Tachibana, H., et al., "Relationship between the Optimal Temperature for Oxidative Refolding and the Thermal Stability of Refolded State of Hen Lysozyme Three–Disulfide Derivatives," *Biochem.* 33:15008–15016, American Chemical Society (1994).

Takahashi, N., "Cyclophiin and FJ506–binding protein," *Seikagaku* 64:325–331, Nihon Seikagakkai (1992).

Timasheff, S.N. and Arakawa, T. "Stabilizations of protein structure of solvents," Chapter 14 in Protein Structure, a practical approach, Creighton, T.E., Ed., IRL Press, Oxford, England, pp. 331–345 (1994).

Timofeev, A.A., et al., "Ispol'zovanie spektral'nykh kharakteristik riodipina dlia izucheniia digidropirinin–retseptornogo kompleksa neironal'nykh membran (The use of spectral characterisitics of ryodipine for the study of dihydropiridin receptor complex in neuronal membranes)," *Biull. Eksp. Biol. Med.* 114: 29–32, Rossiiskaya Akademiya Nauk (1992).

Tsai, P.K., "Formulation Design of Acidic Fibroblast Growth Factor," *Pharm. Res.* 10:649–659, Plenum Publishing Corporation (1993).

Viguera, A.R., et al., "Thermodynamic and Kinetic Analysis of the SH3 Domain of Spectrin Shows a Two–State Folding Transition," *Biochem.* 33:2142–2150, American Chemical Society (1994).

Volkin, D.B., et al., "The Effect of Polyanions on the Stabilization of Acidic Fibroblast Growth Factor," in *Harnessing Biotechnology for the 21st Century. Proceedings of the Ninth International Biotechnology Symposium and Exposition,* Ladisch, M.R. and Bose, A., Eds., American Chemical Society, pp. 298–302 (1992).

Volkin, D.B., et al., "Physical Stabilization of Acidic Fibroblast Growth Factor by Polyanions," *Arch. Biochem. Biophys.* 300:30–41, Academic Press, Inc. (1993).

Wagenhöfer, M., et al., "Thermal Denaturation of Engineered Tet Repressor Proteins and Their Complexes with tet Operator and Tetracycline Studied by Temperature Gradient Gel Electrophoresis," *Anal. Biochem.* 175:422–432, Academic Press, Inc. (1988).

Walz, F.G. and Kitareewan, S., "Spermine Stabilization of a Folded Ribonuclease $T_1$," *J. Biol. Chem.* 265:7127–7137, American Society for Biochemistry and Molecular Biology, Inc. (1990).

Waring, M.J. and Henley, S.M., "Stereochemical aspects of the interaction between steroidal diamine and DNA," *Nucl. Acids Res.* 2:567–586, Oxford University Press (1975).

Weber, P.C., et al., "Structure–Based Design of Synthetic Azobenzene Ligands for Streptavidin," *J. Am. Chem. Soc.* 116:2717–2724, American Chemical Society (1994).

Zahnley, J.C., "Effects of Manganese and Calcium on Conformational Stability of Concanavalin A: A Differential Scanning Calorimetric Study," *J. Inorg. Biochem.* 15:67–78, Elsevier North Holland, Inc. (1981).

Zolkiewski, M. and Ginsburg, A., "Thermodynamic Effects of Active–Site Ligands on the Reversible, Partial Unfolding of Dodecameric Glutamine Synthetase from *Escherichia coli:* Calorimetric Studies," *Biochem.* 31:11991–12000, American Chemical Soceity (1992).

Partial English translation of Fukada, H., "Calorimetry of the Ligand Binding to Proteins," *Tanpakushitsu Kakusan Koso* 33:328–336 (1988).

English translation of Kogtev, L.S., et al., "Use of fluorescein–labeled lipid probes for analyzing Substance P and its derivatives binding to the rat brain tachykinin receptors," *Biologicheskie Membrany* 6:34–41 (1989).

Partial English translation of Kuroki, R. and Inaka, K., "Stabilization of a Protein by Constructing a Ligand Binding Site," *Tanpakushitsu Kakusan Koso* 37:314–321 (1992).

Partial English translation of Kuwajima, K., "Kinetic pathway of globular–protein folding," *Seikagaku* 62:117–121 (1990).

Molecular Probes Catalog, "BioProbes 25, New Products and Applications," Molecular Probes, Inc., pp. 8–9 (May 1997).

435/550 bandpass

475/550 bandpass

MICROPLATE THERMAL SHIFT ASSAY FOR LIGAND DEVELOPMENT USING 5-(4"-DIMETHYLAMINOPHENYL)-2-(4'-PHENYL) OXAZOLE DERIVATIVE FLUORESCENT DYES

This application claims priority benefit of U.S. provisional Appl. No. 60/108,085, filed Nov. 12, 1998, the entirety of which is hereby incorporated by reference.

This invention was made with government support under grant nos. 1 R43 GM52786-01 and 2 R44 GM52786-02 awarded by the NIGMS.

STATEMENT AS TO RIGHTS TO INVENTIONS MADE UNDER FEDERALLY-SPONSORED RESEARCH AND DEVELOPMENT

BACKGROUND OF THE INVENTION

1. Field of the Invention

The present invention relates generally to the screening of compound and combinatorial libraries. More particularly, the present invention relates to a method and apparatus for performing assays, particularly thermal shift assays.

2. Related Art

In recent years, pharmaceutical researchers have turned to combinatorial libraries as sources of new lead compounds for drug discovery. A combinatorial library is a collection of chemical compounds which have been generated, by either chemical synthesis or biological synthesis, by combining a number of chemical "building blocks" as reagents. For example, a combinatorial polypeptide library is formed by combining a set of amino acids in every possible way for a given compound length (i.e., the number of amino acids in a polypeptide compound). Millions of chemical compounds can theoretically be synthesized through such combinatorial mixing of chemical building blocks. Indeed, one investigator has observed that the systematic, combinatorial mixing of 100 interchangeable chemical building blocks results in the theoretical synthesis of 100 million tetrameric compounds or 10 billion pentameric compounds (Gordon, E. M. et al., *J. Med. Chem.* 37:1233–1251 (1994)).

The rate of combinatorial library synthesis is accelerated by automating compound synthesis and evaluation. For example, DirectedDiversity® is a computer based, iterative process for generating chemical entities with defined physical, chemical and/or bioactive properties. The DirectedDiversity® system is disclosed in U.S. Pat. No. 5,463,564, which is herein incorporated by reference in its entirety.

Once a library has been constructed, it must be screened to identify compounds which possess some kind of biological or pharmacological activity. To screen a library of compounds, each compound in the library is equilibrated with a target molecule of interest, such as an enzyme. A variety of approaches have been used to screen combinatorial libraries for lead compounds. For example, in an encoded library, each compound in a chemical combinatorial library can be made so that an oligonucleotide "tag" is linked to it. A careful record is kept of the nucleic acid tag sequence for each compound. A compound which exerts an effect on the target enzyme is selected by amplifying its nucleic acid tag using the polymerase chain reaction (PCR). From the sequence of the tag, one can identify the compound (Brenner, S. et al., *Proc. Natl. Acad. Sci. USA* 89:5381–5383 (1992)). This approach, however, is very time consuming because it requires multiple rounds of oligonucleotide tag amplification and subsequent electrophoresis of the amplification products.

A filamentous phage display peptide library can be screened for binding to a biotinylated antibody, receptor or other binding protein. The bound phage is used to infect bacterial cells and the displayed determinant (i.e., the peptide ligand) is then identified (Scott, J. K. et al., *Science* 249:386–390 (1990)). This approach suffers from several drawbacks. It is time consuming. Peptides which are toxic to the phage or to the bacterium cannot be studied. Moreover, the researcher is limited to investigating peptide compounds.

In International Patent Application WO 94/05394 (1994), Hudson, D. et al., disclose a method and apparatus for synthesizing and screening a combinatorial library of biopolymers on a solid-phase plate, in an array of 4×4 to 400×400. The library can be screened using a fluorescently labeled, radiolabeled, or enzyme-linked target molecule or receptor. The drawback to this approach is that the target molecule must be labeled before it can be used to screen the library.

A challenge presented by currently available combinatorial library screening technologies is that they provide no information about the relative binding affinities of different ligands for a receptor protein. This is true whether the process for generating a combinatorial library involves phage library display of peptides (Scott, J. K. et al., *Science* 249:386–390 (1990)), random synthetic peptide arrays (Lam, K. S. et al., *Nature* 354:82–84 (1991)), encoded chemical libraries (Brenner, S. et al., *Proc. Natl. Acad. Sci. USA* 89:5381–5383 (1992)), the method of Hudson (Intl. Appl. WO 94/05394), or most recently, combinatorial organic synthesis (Gordon, E. et al., *J. Med. Chem.* 37:1385–1399 (1994)).

To acquire quantitative binding data from the high throughput screening of ligand affinities for a target enzyme, researchers have relied on assays of enzyme activity. Enzymes lend themselves to high throughput screening because the effect of ligand binding can be monitored using kinetic assays. The experimental endpoint is usually a spectrophotometric change. Using a kinetic assay, most researchers use a two-step approach to lead compound discovery. First, a large library of compounds is screened against the target enzyme to determine if any of the library compounds are active. These assays are usually performed in a single concentration (between $10^{-4}$–$10^{-6}$ M) with one to three replicates. Second, promising compounds obtained from the first screen (i.e., compounds which display activity greater than a predetermined value) are usually re-tested to determine a 50% inhibitory concentration ($IC_{50}$), an inhibitor association constant ($K_i$), or a dissociation constant ($K_d$). This two-step approach, however, is very labor intensive, time-consuming and prone to error. Each retested sample must either be retrieved from the original assay plate or weighed out and solubilized again. A concentration curve must then be created for each sample and a separate set of assay plates must be created for each assay.

There are other problems associated with the biochemical approach to high throughput screening of combinatorial libraries. Typically, a given assay is not applicable to more than one receptor. That is, when a new receptor becomes available for testing, a new assay must be developed. For many receptors, reliable assays are simply not available. Even if an assay does exist, it may not lend itself to automation. Further, if a $K_i$ is the endpoint to be measured in a kinetic assay, one must first guess at the concentration of inhibitor to use, perform the assay, and then perform additional assays using at least six different concentrations of inhibitor. If one guesses too low, an inhibitor will not exert its inhibitory effect at the suboptimal concentration tested.

In addition to the drawbacks to the kinetic screening approach described above, it is difficult to use the kinetic approach to identify and rank ligands that bind outside of the active site of the enzyme. Since ligands that bind outside of the active site do not prevent binding of spectrophotometric substrates, there is no spectrophotometric change to be monitored. An even more serious drawback to the kinetic screening approach is that non-enzyme receptors cannot be assayed at all.

Thermal protein unfolding, or thermal "shift," assays have been used to determine whether a given ligand binds to a target receptor protein. In a physical thermal shift assay, a change in a biophysical parameter of a protein is monitored as a function of increasing temperature. For example, in calorimetric studies, the physical parameter measured is the change in heat capacity as a protein undergoes temperature induced unfolding transitions. Differential scanning calorimetry has been used to measure the affinity of a panel of azobenzene ligands for streptavidin (Weber, P. et al., *J. Am. Chem. Soc.* 16:2717–2724 (1994)). Titration calorimetry has been used to determine the binding constant of a ligand for a target protein (Brandts, J. et al., *American Laboratory* 22:30–41 (1990)). The calorimetric approach, however, requires that the researcher have access to a calorimetric device. In addition, calorimetric technologies do not lend themselves to the high throughput screening of combinatorial libraries, three thermal scans per day are routine. Like calorimetric technologies, spectral technologies have been used to monitor temperature induced protein unfolding (Bouvier, M. et al., *Science* 265:398–402 (1994); Chavan, A. J. et al., *Biochemistry* 33:7193–7202 (1994); Morton, A. et al., *Biochemistry* 1995:8564–8575 (1995)).

The single sample heating and assay configuration, as conventionally performed, has impeded the application of thermal shift technologies to high throughput screening of combinatorial libraries. Thus, there is a need for a thermal shift technology which can be used to screen combinatorial libraries, can be used to identify and rank lead compounds, and is applicable to all receptor proteins.

Thermal shift assays have been used to determine whether a ligand binds to DNA. Calorimetric, absorbance, circular dichroism, and fluorescence technologies have been used (Pilch, D. S. et al., *Proc. Natl. Acad. Sci. U.S.A.* 91:9332–9336 (1994); Lee, M. et al., *J. Med. Chem.* 36:863–870 (1993); Butour, J.-L. et al., *Eur. J. Biochem.* 202:975–980 (1991); Barcelo, F. et al., *Chem. Biol. Interactions* 74:315–324 (1990)). As used conventionally, however, these technologies have impeded the high throughput screening of nucleic acid receptors for lead compounds which bind with high affinity. Thus, there is a need for a thermal shift technology which can be used to identify and rank the affinities of lead compounds which bind to DNA sequences of interest.

When bacterial cells are used to overexpress exogenous proteins, the recombinant protein is often sequestered in bacterial cell inclusion bodies. For the recombinant protein to be useful, it must be purified from the inclusion bodies. During the purification process, the recombinant protein is denatured and must then be renatured. It is impossible to predict the renaturation conditions that will facilitate and optimize proper refolding of a given recombinant protein. Usually, a number of renaturing conditions must be tried before a satisfactory set of conditions is discovered. In a study by Tachibana et al., each of four disulfide bonds were singly removed, by site-directed mutagenesis, from hen lysozyme (Tachibanaetal, *Biochemistry* 33:15008–15016 (1994)). The mutant genes were expressed in bacterial cells and the recombinant proteins were isolated from inclusion bodies. Each of the isolated proteins were renatured under different temperatures and glycerol concentrations. The efficacy of protein refolding was assessed in a bacteriolytic assay in which bacteriolytic activity was measured as a function of renaturing temperature. The thermal stability of each protein was studied using a physical thermal shift assay. In this study, however, only one sample reaction was heated and assayed at a time. The single sample heating and assay configuration prevents the application of thermal shift technologies to high throughput screening of a multiplicity of protein refolding conditions. Thus, there is a need for a thermal shift technology which can be used to rank the efficacies of various protein refolding conditions.

Over the past four decades, X-ray crystallography and the resulting atomic models of proteins and nucleic acids have contributed greatly to an understanding of structural, molecular, and chemical aspects of biological phenomena. However, crystallographic analysis remains difficult because there are not straightforward methodologies for obtaining X-ray quality protein crystals. Conventional methods cannot be used quickly to identify crystallization conditions that have highest probability of promoting crystallization (Garavito, R. M. et al., *J. Bioenergtics and Biomembranes* 28:13–27 (1996)). Even the use of factorial design experiments and successive automated grid searches (Cox, M. J., & Weber, P. C., *J. Appl. Cryst.* 20:366–373 (1987); Cox, M. J., & Weber, P. C., *J. Crystal Growth* 90:318–324 (1988)) do not facilitate rapid, high throughput screening of biochemical conditions that promote the crystallization of X-ray quality protein crystals. Moreover, different proteins are expected to require different conditions for protein crystallization, just as has been the experience for their folding (McPherson, A., In: *Preparation and Analysis of Protein Crystals*, Wiley Interscience, New York, (1982)). Conventional methods of determining crystallization conditions are cumbersome, slow, and labor intensive. Thus, there is a need for a rapid, high throughput technology which can be used to rank the efficacies of protein crystallization conditions.

Rapid, high throughput screening of combinatorial molecules or biochemical conditions that stabilize target proteins in thermal shift assays would be facilitated by the simultaneous heating of many samples. To date, however, thermal shift assays have not been performed that way. Instead, the conventional approach to performing thermal shift assays has been to heat and assay only one sample at a time. That is, researchers conventionally 1) heat a sample to a desired temperature in a heating apparatus; 2) assay a physical change, such as absorption of light or change in secondary, tertiary, or quaternary protein structure; 3) heat the samples to the next highest desired temperature; 4) assay for a physical change; and 5) continue this process repeatedly until the sample has been assayed at the highest desired temperature.

This conventional approach is disadvantageous for at least two reasons. First, this approach is labor intensive. Second, this approach limits the speed with which thermal shift screening assays can be performed and thereby precludes rapid, high-throughput screening of combinatorial molecules binding to a target receptor and biochemical conditions that stabilize target proteins.

Fluorescent molecules whose spectra or quantum yields are sensitive to their environments are valuable in the study of heterogeneous media, organized media and biological media and many fluorescent dyes have been developed for these applications. However, many dyes either have short absorption and emission wavelengths (potentially causing high background due to the auto fluorescence of samples), low extinction coefficients, low quantum yields, or small Stokes shifts.

Rapid, high-throughput screening using fluorescence methodologies would also be facilitated by the use of fluorescence probe molecules that fluoresce at wavelengths longer than fluorescence molecules such as 1-anilinonaphthalene-8-sulfonate. That is because many molecules in compound and combinatorial libraries fluoresce at the same wavelengths at which fluorescence probe molecules fluoresce. In addition, plastic microplates used in high-throughput screening assays may also fluoresce at the same wavelengths at which fluorescence probe molecules fluoresce.

Thus, there is a need for a rapid, high-throughput, fluorescence screening procedure in which fluorescence readings are taken at wavelengths longer than fluorescence molecules such as 8-anilinonaph-thalene-8-sulfonate.

SUMMARY OF THE INVENTION

The present invention provides a method for ranking the affinity of each of a multiplicity of different molecules for a target molecule which is capable of unfolding due to a thermal change, the method comprising (a) contacting the target molecule with one molecule of a multiplicity of different molecules, in the presence of a 5-(4"-dimethylaminophenyl)-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule in the absence of any of the molecules in the multiplicity of different molecules; and (f) ranking the affinities of each of the molecules according to the difference in the thermal unfolding information between the target molecule in each of the containers and the target molecule in the absence of any of the molecules in the multiplicity of different molecules.

The present invention also provides a multi-variable method for ranking the affinity of a combination of two or more of a multiplicity of different molecules for a target molecule which is capable of unfolding due to a thermal change, the method comprising: (a) contacting the target molecule with a combination of two or more different molecules of the multiplicity of different molecules, in the presence of 5-(4"-dimethylaminophenyl)-2-(4'-phenyl) oxazole derivative dye, in each of a multiplicity of containers; (b) simultaneously heating the multiplicity of containers; (c) measuring in the fluorescence in each of the containers; (d) generating thermal unfolding information for the target molecule as a function of temperature in each of the containers; (e) comparing the thermal unfolding information obtained for each of the containers to (i) the thermal unfolding information obtained for each of the other containers, and (ii) the thermal unfolding information obtained for the target molecule in the absence of any of the two or more different molecules; and (f) ranking the affinities of the combinations of the two or more of the multiplicity of different molecules according to the difference in the thermal unfolding information between the target molecule in each of the containers and the thermal unfolding information obtained for the target molecule in the absence of any of the molecules in the multiplicity of different molecules.

The present invention also provides a method for assaying a collection of a multiplicity of different molecules for a molecule which binds to a target molecule which is capable of unfolding due to a thermal change, the method comprising: (a) contacting the target molecule with a collection of at least two molecules of the multiplicity of different molecules, in the presence of a 5-(4"-dimethylaminophenyl)-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule in the absence of any of the multiplicity of different molecules; and (f) ranking the affinities of the collections of different molecules according to the difference in the thermal unfolding information between the target molecule in each of the containers and the thermal unfolding information obtained for the target molecule in the absence of any of the molecules in the multiplicity of different molecules; (g) selecting the collection of different molecules which contains a molecule with affinity for the target molecule; (h) dividing the selected collection into smaller collections of molecules in each of a multiplicity of containers; and (i) repeating the above steps until a single molecule, from the multiplicity of different molecules, is identified.

The present invention also provides a multi-variable method for ranking the efficacy of one or more of a multiplicity of different biochemical conditions for stabilizing a target molecule which is capable of unfolding due to a thermal change, the method comprising: (a) contacting the target molecule with one or more of the multiplicity of biochemical conditions, in the presence of a 5-(4"-dimethylaminophenyl)-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

The present invention also provides a multi-variable method for optimizing the shelf life of a target molecule which is capable of unfolding due to a thermal change, the method comprising: (a) contacting the target molecule with one or more of a multiplicity of different molecules or different biochemical conditions, in the presence of a 5-(4"-dimethylaminophenyl)-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

The present invention also provides a multi-variable method for ranking the efficacies of one or more of a multiplicity of different biochemical conditions to facilitate the refolding or renaturation of a sample of a denatured or unfolded protein, the method comprising: (a) placing one of the refolded protein samples, in the presence of a 5-(4"-dimethylaminophenyl)-2-(4'-phenyl)oxazole derivative dye, in each of a multiplicity of containers, wherein each of the refolded protein samples has been previously refolded or renatured according to one or more of the multiplicity of conditions; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and (f) ranking the efficacies of each of the biochemical conditions for each of the containers according to the difference in the thermal unfolding information between the target molecule for each of the containers and the target molecule under the reference set of biochemical conditions.

The present invention also provides a multi-variable method for ranking the efficacies of one or more of a multiplicity of different biochemical conditions to facilitate the refolding or renaturation of a sample of a denatured unfolded protein, the method comprising: (a) determining one or more combinations of a multiplicity of different conditions which promote protein stabililty, incubating denatured protein under the one or more combinations of biochemical conditions that were identified as promoting protein stabilization; (b) assessing folded protein yield; (c) ranking the efficacies of the multiplicity of different refolding conditions according to folded protein yield; and (d) repeating these steps until a combination of biochemical conditions that promote optimal protein folding are identified.

The present invention also provides a multi-variable method for ranking the efficacy of one or more of a multiplicity of different biochemical conditions for facilitating the crystallization of a protein which is capable of unfolding due to a thermal change, the method comprising: (a) contacting the protein with one or more of the multiplicity of different biochemical conditions, in the presence of a 5-(4"-dimethylaminophenyl)-2-(4'-phenyl)oxazole derivative dye, in each of a multiplicity of containers; (b) simultaneously heating the multiplicity of containers; (c) measuring the fluorescence in each of the containers; (d) generating thermal unfolding information for the target molecule as a function of temperature for each of the containers; (e) comparing the thermal unfolding information obtained for each of the containers to (i) the thermal unfolding information obtained for each of the other containers, and (ii) the thermal unfolding information obtained for the target molecule under a reference set of biochemical conditions; and ranking the efficacies of each of the biochemical conditions for each of the containers according to the difference in the thermal unfolding information between the target molecule for each of the containers and the target molecule under the reference set of biochemical conditions.

Optimization of protein stability, ligand binding, protein folding, and protein crystallization are multi-variable events. Multi-variable optimization problems require large numbers of parallel experiments to collect as much data as possible in order to determine which variables influence a favorable response. For example, multi-variable optimization problems require large numbers of parallel experiments to collect as much data as possible in order to determine which variables influence protein stabililty. In this regard, both protein crystallization and quantitative structure activity relationship analyses have greatly benefited from mass screening protocols that employ matrix arrays of incremental changes in biochemical or chemical composition. Thus, in much the same way that quantitative structure activity relationships are constructed to relate variations of chemical finctional groups on ligands to their effect on binding affinity to a given therapeutic receptor, the methods and apparatus of the present invention facilitate the construction of a quantitative model that relates different biochemical conditions to experimentally measured protein stability, ligand specificity, folded protein yield, and crystallized protein yield.

Using the fluorescence microplate thermal shift assay, one can determine one or more biochemical conditions that have an additive effect on protein stability. Once a set of biochemical conditions that facilitate an increase in protein stability have been identified using the thermal shift assay, the same set of conditions can be used in protein folding experiments with recombinant protein. If the conditions that promote protein stability in the thermal shift assay correlate with conditions that promote folding of recombinant protein, conditions can be further optimized by performing additional thermal shift assays until a combination of stabilizing conditions that result in further increase protein stability are identified. Recombinant protein is then folded under those conditions. This process is repeated until optimal folding conditions are identified.

The present invention offers a number of advantages over previous technologies that are employed to optimize multi-variable events such as protein stabilization, ligand binding, protein folding, and protein crystallization. Foremost among these advantages is that the present invention facilitates high throughput screening. The use of 5-(4"-dimethylaminophenyl)-2-(4'-phenyl)oxazole derivative dyes to practice the microplate thermal shift assay of the present invention affords increased assay sensitivity and increased assay throughput, because these dyes have long emission wavelengths, high extinction coefficients, high quantum yields, and large Stokes shifts.

Further, the methods of the present invention offers a number of advantages over previous technologies that are employed to screen combinatorial libraries. Foremost among these advantages is that the present invention facilitates high throughput screening of combinatorial libraries for lead compounds. Many current library screening technologies simply indicate whether a ligand binds to a receptor or not. In that case, no quantitative information is provided. No information about the relative binding affinities of a series of ligands is provided. In contrast, the present invention facilitates the ranking of a series of compounds for their relative affinities for a target receptor. With this information in hand, a structure-activity relationship can be developed for a set of compounds. The ease, reproducibility, and speed of using ligand-dependent changes in midpoint unfolding temperature ($T_m$) to rank relative binding affinities makes the present invention a powerful tool in the drug discovery process.

Typically, the conventional kinetic screening approach requires at least six additional well assays at six different concentrations of inhibitor to determine a $K_i$. Using the present invention, throughput is enhanced ~6 fold over the enzyme based assays because one complete binding experiment can be performed in each well of a multiwell microplate. The kinetic screening approached are even further limited by the usual compromise between dilution and signal detection, which usually occurs at a protein concentration of about 1 nM. In this regard, the calorimetric approaches, either differential scanning calorimetry or isothermal titrating calorimetry, are at an even worse disadvantage since they are limited to solitary binding experiments, usually 1 per hour. In contrast, the present invention affords a wide dynamic range of measurable binding affinities, from $\sim 10^{-4}$ to $10^{-15}$ M, in a single well.

A very important advantage of the present invention is that it can be applied universally to any receptor that is a drug target. Thus, it is not necessary to invent a new assay every time a new receptor becomes available for testing. When the receptor under study is an enzyme, researchers can determine the rank order of affinity of a series of compounds more quickly and more easily than they can using conventional kinetic methods. In addition, researchers can detect ligand binding to an enzyme, regardless of whether binding occurs at the active site, at an allosteric cofactor binding site, or at a receptor subunit interface. The present invention is equally applicable to non-enzyme receptors, such as proteins and nucleic acids.

Further features and advantages of the present invention are described in detail below with reference to the accompanying drawings.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

In FIG. 17A, the fluorophore is 1,8-ANS. In FIG. 17B, the fluorophore is 2,6-ANS. In FIG. 17C, the fluorophore is 2,6-TNS. In FIG. 17D, the fluorophore is bis-ANS.

FIG. 32A shows a side view of the thermal electric stage. FIG. 32B shows a top view of the thermal electric stage. FIGS. 32C–E show three configurations of inserts that can be attached to the thermal electric stage. In one embodiment, inserts accommodate a microtitre plate. In such an embodiment, assay samples are contained within the containers of the microtitre plate.

FIG. 41A: V-bottom well microplate. FIG. 41B: dimple microplate.

(FIG. 43B)

DETAILED DESCRIPTION OF THE PREFERRED EMBODIMENTS

Figure 1:
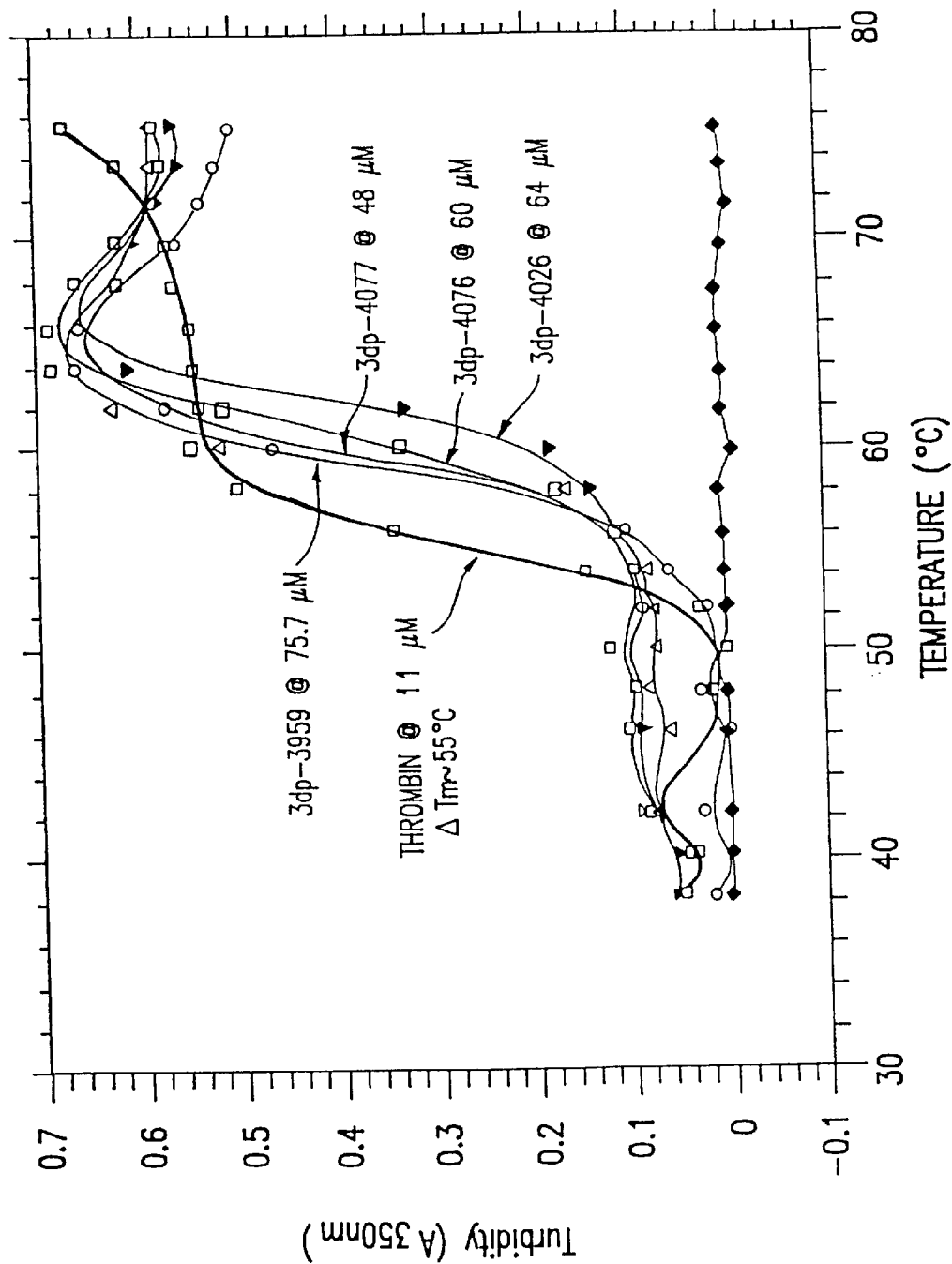
FIG. 1 shows the results of a microplate thermal shift assay for ligands which bind to the active site of human α-thrombin (with turbidity as the experimental signal).

In the following description, reference will be made to various terms and methodologies known to those of skill in the biochemical and pharmacological arts. Publications and other materials setting forth such known terms and methodologies are incorporated herein by reference in their entireties as though set forth in full.

The present invention provides a method for ranking a multiplicity of different molecules in the order of their ability to bind to a target molecule which is capable of unfolding due to a thermal change. In one embodiment of this method, the target molecule is contacted with one molecule of a multiplicity of different molecules in each of a multiplicity of containers. The containers are then simultaneously heated, in intervals, over a range of temperatures. After each heating interval, thermal unfolding information (e.g., the thermal unfolding temperature midpoint ($T_m$)) is measured. In an alternate embodiment of this method, the containers are heated in a continuous fashion, and thermal unfolding information (e.g., the thermal unfolding $T_m$) is obtained for each container. Preferably, the temperature midpoint $T_m$ is identified and is then compared to the $T_m$ for the target molecule in the absence of any of the molecules in the containers. Alternatively, an entire thermal unfolding curve can be compared to other entire thermal unfolding curves using computer analytical tools.

The steps in any of the methods of the present invention can be repeated, until a molecule that binds to a target molecule is identified, or until a set of biochemical conditions that stabilize a target molecule is determined, or until a set of biochemical conditions that facilitate refolding or renaturation of a protein is determined, or until a set of biochemical conditions that optimize the shelf life of a protein is determined, or until a set of biochemical conditions that facilitate protein crystallization is determined.

The term "combinatorial library" refers to a plurality of molecules or compounds which are formed by combining, in every possible way for a given compound length, a set of chemical or biochemical building blocks which may or may not be related in structure. Alternatively, the term can refer to a plurality of chemical or biochemical compounds which are formed by selectively combining a particular set of chemical building blocks. Combinatorial libraries can be constructed according to methods familiar to those skilled in the art. For example, see Rapoport et al., Immunology Today 16:43–49 (1995); Sepetov, N. F. et al., Proc. Natl. Acad. Sci.

U.S.A. 92:5426–5430 (1995); Gallop, M. A. et al., J. Med. Chem. 9:1233–1251 (1994); Gordon, E. M. et al., J. Med. Chem. 37:1385–1401 (1994); Stankova, M. et al., Peptide Res. 7:292–298 (1994); Erb, E. et al., Proc. Natl. Acad. Sci. U.S.A. 91:11422–11426 (1994); DeWitt, S. H. et al., Proc. Natl. Acad. Sci. U:S.A. 90:6909–6913 (1993); Barbas, C. F. et al., Proc. Natl. Acad. Sci. U.S.A. 89:4457–4461 (1992); Brenner, S. et al. Proc. Natl. Acad. Sci. U.S.A. 89:5381–5383 (1992); Lam, K. S. et al., Nature 354:82–84 (1991); Devlin, J. J. et al., Science 245:404–406 (1990); Cwirla, S. E. et al., Proc. Natl. Acad. Sci. U.S.A. 87:6378–6382 (1990); Scott, J. K. et al., Science 249:386–390 (1990). Preferably, the term "combinatorial library" refers to a directed diversity chemical library, as set forth in U.S. Pat. No. 5,463,564. Regardless of the manner in which a combinatorial library is constructed, each molecule or compound in the library is catalogued for future reference.

The term "compound library" refers to a plurality of molecules or compounds which were not formed using the combinatorial approach of combining chemical or biochemical building blocks. Instead, a compound library is a plurality of molecules or compounds which are accumulated and are stored for use in future ligand-receptor binding assays. Each molecule or compound in the compound library is catalogued for future reference.

The terms "multiplicity of molecules," "multiplicity of compounds," or "multiplicity of containers" refer to at least two molecules, compounds, or containers.

The term "multi-variable" refers to more than one experimental variable.

The term "screening" refers to the testing of a multiplicity of molecules or compounds for their ability to bind to a target molecule which is capable of unfolding. Screening is a repetitive, or iterative, process, in which molecules are tested for binding to a target molecule (e.g, a protein receptor) in a thermal shift assay. For example, if none of a subset of molecules from the multiplicity of molecules (e.g., a combinatorial library) bind to the target molecule, then a different subset is tested for binding in a thermal shift assay.

The term "ranking" refers to the ordering of the affinities of a multiplicity of molecules or compounds for a target molecule, according to the ability of the molecule or compound to shift the thermal unfolding information (e.g., thermal unfolding $T_m$)obtained for the target molecule, relative to the thermal unfolding information of the target molecule in the absence of any molecule or compound.

The term "high-throughput" encompasses screening activity in which human intervention is minimized, and automation is maximized. For example, high-throughput screening involves automated pipetting, mixing, and heating, software-controlled generation of thermal unfolding information, and software-controlled comparisons of thermal unfolding information. Alternatively, a high-throughput method is one in which hundreds of compounds can be screened per 24 hour period by a single individual operating a single suitable apparatus.

"Performed automatically" means that at least some aspects of the screening process are performed by a machine, and optionally are computer-controlled.

The term "ranking" also refers to the ordering of the efficacies of a multiplicity of biochemical conditions in optimizing protein stabilization, protein folding, protein crystallization, or protein shelf life. In the context of optimization of protein stabilization, optimization of protein folding, optimization of protein crystallization, and optimization of protein shelf life, the term "ranking" refers to the ordering of the efficacies of one or more combinations of biochemical conditions to shift the thermal unfolding information (e.g., thermal unfolding $T_m$) obtained for the target molecule, relative to the thermal unfolding information of the target molecule under a reference set of conditions.

As discussed above, ranking molecules, compounds, or biochemical conditions according to a change in the $T_m$ is preferable. Alternatively, molecules, compounds, or biochemical conditions can be ranked for their ability to stabilize a target molecule according to the change in entire thermal unfolding curve.

As used herein, the terms "protein" and "polypeptide" are synonymous. For proteins or peptides, the term "unfolding" encompasses any change in structure due to heating. For example, the term "unfolding" refers to the transition of from the liquid crystalline state to the molten globule state. In the molten globule state, tertiary and quaternary structure has been altered, relative to the native state of the protein, and at least some secondary structure remains intact. The term "unfolding" also encompasses loss of crystalline ordering of amino acid side-chains, secondary, tertiary or quaternary structure. The term "unfolding" also encompasses formation of a random coil.

The terms "folding," "refolding," and "renaturing" refer to the acquisition of the correct amino acid side-chain ordering, secondary, tertiary, or quaternary structure, of a protein or a nucleic acid, which affords the full chemical and biological function of the biomolecule.

The term "denatured protein" refers to a protein which has been treated to remove native amino acid side-chain ordering, secondary, tertiary, or quaternary structure. The term "native protein" refers to a protein which possesses the degree of amino acid side-chain ordering, secondary, tertiary or quaternary structure that provides the protein with full chemical and biological function. A native protein is one which has not been heated and has not been treated with a chemical unfolding agent, such as urea.

For nucleic acids, the term "unfolding" refers to the loss of secondary, tertiary and quaternary structure through unfolding, uncoiling, untwisting or loss of helical structure. The loss of double- or triple-helical structure through the interruption of base-paring is an example of unfolding of a nucleic acid.

The terms "unfolded nucleic acid" and "denatured nucleic acid" refer to a nucleic acid which has been treated to remove folded, coiled, helical, or twisted structure. Unfolding of a triple-stranded nucleic acid complex is complete when the third strand has been removed from the two complementary strands. Unfolding of a double-stranded DNA is complete when the base pairing between the two complementary strands has been interrupted and has resulted in single-stranded DNA molecules that have assumed a random form. Unfolding of single-stranded RNA is complete when intramolecular hydrogen bonds have been interrupted and the RNA has assumed a random, non-hydrogen bonded form.

An "unfolding curve" is a plot of the physical change associated with the unfolding of a protein as a function temperature, denaturant concentration, pressure, etc. An unfolding curve can be generated digitally or by plotting on paper or a computer screen. A "thermal unfolding curve" is a plot of the physical change associated with the unfolding of a protein or a nucleic acid as a function of temperature. See, for example, Davidson et al., *Nature Structure Biology* 2:859 (1995); and Clegg, R. M. et al., *Proc. Natl. Acad. Sci.*

U.S.A. 90:2994–2998 (1993). A thermal unfolding curve can be generated digitally or by plotting on paper or a computer screen, Preferably, a thermal unfolding curve is generated digitally The "midpoint temperature, $T_m$" is the temperature midpoint of a thermal unfolding curve. At the temperature midpoint $T_m$, one half of the target molecules in a sample are unfolded, and one half of the target molecules in the sample remain folded. The $T_m$ can be readily determined using methods well known to those skilled in the art. See, for example, Weber, P. C. et al., J. Am. Chem. Soc. 116:2717–2724 (1994); Clegg, R. M. et al., Proc. Natl. Acad. Sci. U.S.A. 90:2994–2998 (1993). Preferably, the $T_m$ is extracted digitally from a digital thermal unfolding curve "Thermal unfolding information" is information relating to target molecule unfolding in response to heating. For example, a thermal unfolding curve is one kind of thermal unfolding information. A thermal unfolding curve can be plotted on a computer screen, or on paper. Preferably, a thermal unfolding curve is generated digitally, using computer software, and may then be visualized on a computer screen. More preferably, thermal unfolding information is thermal unfolding $T_m$. A digitally generated thermal unfolding curve need not be printed or displayed in order for the thermal unfolding $T_m$ to be extracted from the digitally generated curve. Most preferably, the thermal unfolding $T_m$ is digitally extracted from a digitally generated thermal unfolding curve.

When thermal unfolding information is generated digitally, five fitting parameters are evaluated: (1) $y_f$, the pre-transitional fluorescence for the native protein; (2) $y_u$, the post-transitional fluorescence for the unfolded protein; (3) $T_m$, the temperature at the midpoint for the unfolding transition; (4) $\Delta H_u$, the van't Hoff unfolding enthalpy change; and (5) $\Delta C_{pu}$, the change in heat capacity upon protein unfolding. The non-linear least squares curve fitting can be performed using a suitable software, such as KALEIDAGRAPH™ 3.0 software (Synergy Software, Reading Pa.), which allows the five fitting parameters to float while utilizing Marquardt methods for the minimization of the sum of the squared residuals. The temperature midpoint $T_m$ is extracted from the digitally generated thermal unfolding information.

The term "lead molecule" refers to a molecule or compound, from a combinatorial library, which displays relatively high affinity for a target molecule.

The terms "lead compound" and "lead molecule" are synonymous. The term "relatively high affinity" relates to affinities in the $K_d$ range of from $10^{-4}$ to $10^{-15}$ M.

The term "target molecule" encompasses peptides, proteins, nucleic acids, and other receptors. The term encompasses both enzymes, and proteins which are not enzymes. The term encompasses monomeric and multimeric proteins. Multimeric proteins may be homomeric or heteromeric. The term encompasses nucleic acids comprising at least two nucleotides, such as oligonucleotides. Nucleic acids can be single-stranded, double-stranded or triple-stranded. The term encompasses a nucleic acid which is a synthetic oligonucleotide, a portion of a recombinant DNA molecule, or a portion of chromosomal DNA. The term target molecule also encompasses portions of peptides, proteins, and other receptors which are capable of acquiring secondary, tertiary, or quaternary structure through folding, coiling or twisting. The target molecule may be substituted with substituents including, but not limited to, cofactors, coenzymes, prosthetic groups, lipids, oligosaccharides, or phosphate groups.

The terms "target molecule" and "receptor" are synonymous. The term "target molecule" refers more specifically to proteins involved in the blood coagulation cascade, fibroblast growth factors, fibroblast growth factor receptors, urokinase, and factor D.

Examples of target molecules are included, but not limited to those disclosed in Faisst, S. et al., Nucleic Acids Research 20:3–26 (1992); Pimentel, E., Handbook of Growth Factors, Volumes I–III, CRC Press, (1994); Gilman, A. G. et al., The Pharmacological Basis of Therapeutics, Pergamon Press (1990); Lewin, B., Genes V, Oxford University Press (1994); Roitt, I., Essential Immunology, Blackwell Scientific Publ. (1994); Shimizu, Y., Lymphocyte Adhesion Molecules, R G Landes (1993); Hyams, J. S. et al., Microtubules, Wiley-Liss (1995); Montreuil, J. et al., Glycoproteins, Elsevier (1995); Woolley, P., Lipases: Their Structure Biochemistry and Applications, Cambridge University Press (1994); Kurjan, J., Signal Transduction: Prokaryotic and Simple Eukaryotic Systems, Academic Press (1993); Kreis, T., et al., Guide Book to the Extra Cellular Matrix and Adhesion Proteins, Oxford University Press (1993); Schlesinger, M. J., Lipid Modifications of Proteins, CRC Press (1992); Conn, P. M., Receptors: Model Systems and Specific Receptors, Oxford University Press (1993); Lauffenberger, D. A. et al., Receptors: Models For Binding Trafficking and Signaling, Oxford University Press (1993); Webb, E. C., Enzyme Nomenclature, Academic Press (1992); Parker, M. G., Nuclear Hormone Receptors; Molecular Mechanisms, Cellular Functions Clinical Abnormalities, Academic Press Ltd. (1991); Woodgett, J. R., Protein Kinases, Oxford University Press (1995); Balch, W. E. et al., Methods in Enzymology, 257, Pt. C: Small GTPases and Their Regulators: Proteins Involved in Transport, Academic Press (1995); The Chaperonins, Academic Press (1996); Pelech, L., Protein Kinase Circuitry in Cell Cycle Control, R G Landes (1996); Atkinson, Regulatory Proteins of the Complement System, Franklin Press (1992); Cooke, D. T. et al., Transport and Receptor Proteins of Plant Membranes: Molecular Structure and Function, Plenum Press (1992); Schumaker, V. N., Advances in Protein Chemistry: Lipoproteins, Apolipoproteins, and Lipases, Academic Press (1994); Brann, M., Molecular Biology of G-Protein-Coupled Receptors: Applications of Molecular Genetics to Pharmacology, Birkhauser (1992); Konig, W., Peptide and Protein Hormones: Structure, Regulations, Activity—A Reference Manual, VCH Publ. (1992); Tuboi, S. et al., Post-Translational Modification of Proteins, CRC Press (1992); Heilmeyer, L. M., Cellular Regulation by Protein Phosphorylation, Springer-Verlag (1991); Takada, Y., Integrin: The Biological Problem, CRC Press (1994); Ludlow, J. W., Tumor Suppressors: Involvement in Human Disease, Viral Protein Interactions, and Growth Regulation, R G Landes (1994); Schlesinger, M. J., Lipid Modification of Proteins, CRC Press (1992); Nitsch, R. M., Alzheimer's Disease: Amyloid Precursor Proteins, Signal Transduction, and Neuronal Transplantation, New York Academy of Sciences (1993); Cochrane, C. G. et al., Cellular and Molecular Mechanisms of Inflammation, Vol.3: Signal Transduction in Inflammatory Cells, Part A, Academic Press (1992); Gupta, S. et al., Mechanisms of Lymphocyte Activation and Immune Regulation IV: Cellular Communications, Plenum Press (1992); Authi, K. S. et al., Mechanisms of Platelet Activation and Control, Plenum Press (1994); Grunicke, H., Signal Transduction Mechanisms in Cancer, R G Landes (1995); Latchman, D. S., Eukaryotic Transcription Factors, Academic Press (1995).

The term "molecule" refers to the compound which is tested for binding affinity for the target molecule. This term encompasses chemical compounds of any structure, including, but not limited to nucleic acids and peptides. More specifically, the term "molecule" encompasses compounds in a compound or a combinatorial library.

The term "fluorescence" encompasses the release of fluorescent energy. Less broadly, the term "fluorescence" refers to fluorescent emission, the rate of change of fluorescence over time (i.e., fluorescence lifetime), fluorescence polarization, fluorescence anisotropy, and fluorescence resonance energy transfer. See Eftink, M. R., *Biophysical J.* 66: 482–501 (1994).

The term "contacting a target molecule" refers broadly to placing the target molecule in solution with the molecule to be screened for binding or with the condition(s) to be tested for stabilizing the target molecule. Less broadly, contacting refers to the turning, swirling, shaking or vibrating of a solution of the target molecule and the molecule to be screened for binding. More specifically, contacting refers to the mixing of the target molecule with the molecule to be tested for binding. Mixing can be accomplished, for example, by repeated uptake and discharge through a pipette tip, either manually or using an automated pipetting device. Preferably, contacting refers to the equilibration of binding between the target molecule and the molecule to be tested for binding. Contacting can occur in the container (infra) or before the target molecule and the molecule to be screened are placed in the container.

The target molecule may be contacted with a nucleic acid prior to being contacted with the molecule to be screened for binding. The target molecule may be complexed with a peptide prior to being contacted with the molecule to be screened for binding. The target molecule may be phosphorylated or dephosphorylated prior to being contacted with the molecule to be screened for binding.

A carbohydrate moiety may be added to the target molecule before the target molecule is contacted with the molecule to be screened for binding. Alternatively, a carbohydrate moiety may be removed from the target molecule before the target molecule is contacted with the molecule to be screened for binding.

The term "container" refers to any vessel or chamber in which the receptor and molecule to be tested for binding can be placed. The term "container" encompasses reaction tubes (e.g., test tubes, microtubes, vials, etc.). In the methods of the present invention, the the term "container" preferably refers to a well in a multiwell microplate or multiwell microtiter plate.

The term "sample" refers to the contents of a container.

The terms "spectral emission," "thermal change" and "physical change" encompass the release of energy in the form of light or heat, the absorption of energy in the form or light or heat, changes in turbidity and changes in the polar properties of light. Specifically, the terms refer to fluorescent emission, fluorescent energy transfer, absorption of ultraviolet or visible light, changes in the polarization properties of light, changes in the polarization properties of fluorescent emission, changes in the rate of change of fluorescence over time (i.e., fluorescence lifetime), changes in fluorescence anisotropy, changes in fluorescence resonance energy transfer, changes in turbidity, and changes in enzyme activity. Preferably, the terms refer to fluorescence, and more preferably to fluorescence emission. Fluorescence emission can be intrinsic to a protein or can be due to a fluorescence reporter molecule. The use of fluorescence techniques to monitor protein unfolding is well known to those of ordinary skill in the art. For example, see Eftink, M. R., *Biophysical J.* 66: 482–501 (1994).

The fluorescence microplate thermal shift assay is disclosed in U.S. Pat. Application Ser. Nos. 08/853,464 and 08/853,459, filed May 9, 1997, and in international patent Appl. No. PCT/US97/08154 (published Nov. 13, 1997 as publication no. WO 97/42500).

A 5-(4"-dimethylaminophenyl)-2-(4'-phenyl)oxazole "derivative" dye is a molecule that comprises the 5-(4"-dimethylaminophenyl)-2-(4'-phenyl)oxazole structure. In the methods of the present invention, 5-(4"-dimethylaminophenyl)-2-(4'-phenyl)oxazole derivative dyes can be selected from the group consisting of the following 5-(4"-dimethylaminophenyl)-2-(4'-phenyl) oxazole derivative dyes: 5-(4"-dimethylaminophenyl)-2-(4'-phenyl)oxazole butylsulfonamide, or a salt or ester thereof; 5-(4"-dimethylaminophenyl)-2-(4'-phenyl)oxazole-(2-aminoethyl)sulfonamide, or a salt or ester thereof; 5-(4"-dimethylaminophenyl)-2-(4'-phenyl)oxazole-3-sulfonamidophyenylboronic acid, or a salt or ester thereof; 5-(4"-dimethylaminophenyl)-2-(4'-phenyl)oxazole sulfonic acid, or a salt or ester thereof; 5-(4"-dimethylaminophenyl)-2-(4'-phenyl)oxazole sulfonyl hydrazine, 5-(4"-dimethylaminophenyl)-2-(4'-phenyl)oxazole-2-bromoacetamidoethyl)sulfonamide, or a salt or ester thereof; 5-(4"-dimethylaminophenyl)-2-(4'-phenyl)oxazole-2-(3-(2-pyridyldithio) propionamidoethyl)sulfonamide, or a salt or ester thereof; 5-(4"-dimethylaminophenyl)-2-(4'-phenyl) oxazole sulfonyl chloride, or a salt or ester thereof; 5-(4"-dimethylaminophenyl)-2-(4'-phenyl)oxazole-3-sulfonamidopropionic acid, or a salt or ester thereof; 5-(4"-dimethylaminophenyl)-2-(4'-phenyl)oxazole carboxylic acid, or a salt or ester thereof; and 5-(4"-dimethylaminophenyl)-2-(4'-phenyl)oxazole sulfonate, or a salt or ester thereof.

Examples of acid salts are hydrochloric, nitric, sulfuric, phosphoric, formic, acetic, trifluoroacetic, propionic, maleic, succinic, malonic, methane sulfonic and the like, salts formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The ester can be methyl; ethyl; butyl; acetate; maleate; pivaloyloxymethyl; phenyl; substituted phenyl; alkyl; benzyl; pivaloyloxymethyl; methoxyrnethyl; (1–6C) alkanoyloxymethyl esters, for example pivaloyloxymethyl, phthalidyl esters; (3–8C)cycloalkoxycarbonyloxy esters; (1–6C)alkyl esters, for example 1-cyclohexylcarbonyloxyethyl; 1,3-dioxolen-2-onylmethyl esters, for example 5-methyl-1,3-dioxolen-2-onylmethyl; (1–6C)alkoxycarbonyloxyethyl esters; phosphate esters; alpha-acyloxyalkyl ethers and related compounds which as a result of the in-vivo hydrolysis of the ester breakdown to give the parent hydroxy group acetoxymethoxy and 2,2-dimethylpropionyloxymethoxy.

5-(4"-dimethylaminophenyl)-2-(4'-phenyl)oxazole dyes can be purchased from Molecular Probes, Inc., Eugene, Oreg., and such dyes are provided in Diwu, Z. et al., *Photochemistry and Photobiology* 66 (4): 424–431 (1997), and in *BioProbes* 25: pp. 8–9, Molecular Probes, Inc., Eugene, Oreg. (1997). Such dyes include 5-(4"-dimethylaminophenyl)-2-(4'-phenyl)oxazole butylsulfonamide (Molecular Probes catalogue no. D-12801), 5-(4"-dimethylaminophenyl)-2-(4'-phenyl)oxazole-(2-aminoethyl)sulfonamide (Molecular Probes catalogue no.

D-10460), 5-(4"-dimethylaminophenyl)-2-(4'-phenyl) oxazole-3-sulfonamidophyenylboronic acid (Molecular Probes catalogue no. D-10402), 5-(4"-dimethylaminophenyl)-2-(4'-phenyl)oxazole sulfonic acid, sodium salt (Molecular Probes catalogue no. D-12800), 5-(4"-dimethylaminophenyl)-2-(4'-phenyl)oxazole sulfonyl hydrazine (Molecular Probes catalogue no. D-10430), 5-(4"-dimethylaminophenyl)-2-(4'-phenyl)oxazole-(2-bromoacetamidoethyl)sulfonamide (MolecularProbes catalogue no. D-10300), 5-(4"-dimethylaminophenyl)-2-(4'-phenyl)oxazole-2-(3-(2-pyridyldithio) propionamidoethyl) sulfonamide (Molecular Probes catalogue no. D-10301), 5-(4"-dimethylaminophenyl)-2-(4'-phenyl)oxazole sulfonyl chloride (Molecular Probes catalogue no. D-10160), 5-(4"-dimethylaminophenyl)-2-(4'-phenyl)oxazole-3-sulfonamidopropionic acid, succinimidyl ester (Molecular Probes catalogue no. D-10162), 5-(4"-dimethylaminophenyl)-2-(4'-phenyl)oxazole carboxylic acid, succinimidyl ester (Molecular Probes catalogue no. D-10161).

In the methods of the present invention, the 5-(4"-dimethylaminophenyl)-2-(4'-phenyl)oxazole derivative dye is preferably 5-(4"-dimethylaminophenyl)-2-(4'-phenyl) oxazole sulfonate, sodium salt (Molecular Probes catalogue no. D-12800).

5-(4"-dimethylaminophenyl)-2-(4'-phenyl)oxazole derivative dye provide a higher fluorescence signal than does 1-anilinonaphthalene-8-sulfonate (1,8-ANS). 5-(4"-dimethylaminophenyl)-2-(4'-phenyl)oxazole derivative dyes can be used to monitor fluorescence associated with protein unfolding in at a wavelength from about 475 nm to about 570 nm, more preferably from about 500 nm to about 550 nm, and still more preferably at about 500 nm or 525 nm.

Methods for synthesizing other 5-(4"-dimethylaminophenyl)-2-(4'-phenyl)oxazole derivative dyes are well known to those of ordinary skill in the art. For example, see Diwu, Z. et al., *Photochemistry and Photobiology* 66 (4): 424–431 (1997).

The term "fluorescence probe molecule" refers to an extrinsic fluorophore, which is a fluorescent molecule or a compound which is capable of associating with an unfolded or denatured receptor and, after excitement by light of a defined wavelength, emits fluorescent energy. The term fluorescence probe molecule encompasses all fluorophores. More specifically, for proteins, the term encompasses fluorophores such as thioinosine, and N-ethenoadenosine, formycin, dansyl, dansyl derivatives, fluorescein derivatives, 6-propionyl-2-(dimethylamino)-napthalene (PRODAN), 2-anilinonapthalene, and N-arylamino-naphthalene sulfonate derivatives such as 1-anilinonaphthalene-8-sulfonate (1,8-ANS), 2-anilinonaphthalene-6-sulfonate (2,6-ANS), 2-amino-naphthalene-6-sulfonate, N,N-dimethyl-2-aminonaphthalene-6-sulfonate, N-phenyl-2-aminonaphthal-ene, N-cyclohexyl-2-aminonaphthalene-6-sulfonate, N-phenyl-2-amino-naphthalene-6-sulfonate, N-phenyl-N-methyl-2-aminonaphthalene-6-sulfonate, N-(o-toluyl)-2-amino-naphthalene-6-sulfonate, N-(m-toluyl)-2-amino-naphthalene-6-sulfonate, N-(p-toluyl)-2-aminonaphthalene-6-sulfonate, 2-(p-toluidinyl)-naphthalene-6-sulfonic acid (2,6-TNS), 4-(dicyanovinyl) julolidine (DCVJ), 6-dodecanoyl-2-dimethylaminonaphthalene (LAURDAN), 6-hexadecanoyl-2-(((2-(trimethylammonium)ethyl)methyl)-amino) naphthalene chloride (PATMAN), nile red, N-phenyl-1-naphthylamine, 1,1-dicyano-2-[6-(dimethylamino) naphthalen-2-yl]propene (DDNP), 4,4'-dianilino-1,1-binaphthyl-5,5-disulfonic acid (bis-ANS), and 5-(4"-dimethylaminophenyl)-2-(4'-phenyl)oxazole derivative dyes, sold under the trademark DAPOXYL™ (Molecular Probes, Inc., Eugene, Oreg.), including the 5-(4"-dimethylaminophenyl)-2-(4'-phenyl)oxazole dyes provided in Diwu, Z. et al., *Photochemistry and Photobiology* 66 (4): 424–431 (1997), and in *BioProbes* 25: pp. 8–9, Molecular Probes, Inc., Eugene, Oreg. (1997).

If the target molecule or receptor to be studied is a nucleic acid, fluorescence spectrometry can be performed using fluorescence resonance emission transfer. The transfer of fluorescent energy, from a donor fluorophore on one strand of an oligonucleotide to an acceptor fluorophore on the other strand, is monitored by measuring the fluorescence of the acceptor fluorophore. Unfolding or denaturation prevent the transfer of fluorescent energy. The fluorescence resonance emission transfer methodology is well known to those skilled in the art. Fore example, see Ozaki, H. et al., Nucleic Acids Res. 20:5205–5214 (1992); Clegg, R. M. et al., Proc. NAtl. Acad. Sci. U.S.A. 90:2994–2998 (1993); Clegg, R. M. et al., Biochemistry 31:4846–4856 (1993).

One strand of a double-stranded oligonucleotide will contain the donor fluorophore. The other strand of the oligonucleotide will contain the acceptor fluorophore. For a nucleic acid to "contain" a donor or an acceptor fluorophore, the fluorophore can be incorporated directly into the oligonucleotide sequence. Alternatively, the fluorophore can be attached to either the 5'- or 3'-terminus of the oligonucleotide.

A donor fluorophore is one which, when excited by light, will emit fluorescent energy. The energy emitted by the donor fluorophore is absorbed by the acceptor fluorophore. The term "donor fluorophore" encompasses all fluorophores including, but not limited to, carboxyfluorescein, iodoacetamidofluorescein, and fluorescein isothiocyanate. The term "acceptor fluorophore" encompasses all fluorophores including, but not limited to, iodoacetamidoeosin and tetramethylrhodamine.

The term "carrier" encompasses a platform or other object, of any shape, which itself is capable of supporting at least two containers. The carrier can be made of any material, including, but not limited to glass, plastic, or metal. Preferably, the carrier is a multiwell microplate. The terms microplate and microtiter plate are synonymous. The carrier can be removed from the heating element. In the present invention, a plurality of carriers are used. Each carrier holds a plurality of wells.

The term "biochemical conditions" encompasses any component of a physical, chemical, or biochemical reaction. Specifically, the term refers to conditions of temperature, pressure, protein concentration, pH, ionic strength, salt concentration, time, electric current, potential difference, concentrations of cofactor, coenzyme, oxidizing agents, reducing agents, detergents, metal ion, ligands, or glycerol.

The term "efficacy" refers to the effectiveness of a particular set of biochemical conditions in facilitating the refolding or renaturation of an unfolded or denatured protein.

The term "reference set of conditions" refers to a set of biochemical conditions under which thermal unfolding information for a target molecule is obtained. Thermal unfolding information obtained under conditions different than the reference conditions is compared to the thermal unfolding information obtained for the target molecule under reference conditions.

The term "polarimetric measurement" relates to measurements of changes in the polarization of fluorescence.

The term "collection" refers to a pool or a group of at least two molecules to be tested for binding to a target molecule or receptor in a single container.

A "host" is a bacterial cell that has been transformed with recombinant DNA for the purpose of expressing protein which is heterologous to the host bacterial cell.

The fluorescence thermal shift assay is based on the ligand-dependent change in thermal unfolding information (e.g., the $T_m$) of a target receptor, such as a protein or a nucleic acid. When heated over a range of temperatures, a receptor will unfold. By plotting the degree of unfolding as a function of temperature, one obtains a thermal unfolding curve for the receptor. Naturally, a thermal unfolding curve can be generated digitally, using computer software. The temperature midpoint $T_m$ is the temperature at which one half of the receptor molecules are unfolded, and one half of the molecules remain folded.

Ligand binding stabilizes the receptor (Schellman, J., *Biopolymers* 14:999–1018 (1975)). The extent of binding and the free energy of interaction follow parallel courses as a function of ligand concentration (Schellman, J., *Biophysical Chemistry* 45:273–279 (1993); Barcelo, F. et al., *Chem. Biol. Interactions* 74:315–324 (1990)). As a result of stabilization by ligand, more energy (heat) is required to unfold the receptor. Thus, ligand binding shifts the thermal unfolding information (e.g., the $T_m$). This property can be exploited to determine whether a ligand binds to a receptor: a change, or "shift", in the thermal unfolding information, and thus means that the ligand binds to the receptor.

The thermodynamic basis for the thermal shift assay has been described by Schellman, J. A. (*Biopolymers* 15:999–1000 (1976)), and also by Brandts et al. (Biochemistry 29:6927–6940 (1990)). Differential scanning calorimetry studies by Brandts et al., (Biochemistry 29:6927–6940 (1990)) have shown that for tight binding systems of 1:1 stoichiometry, in which there is one unfolding transition, one can estimate the binding affinity at $T_m$ from the following expression:

$$K_L^{T_m} = \frac{\exp\left\{-\frac{\Delta H_u^{T_0}}{R}\left[\frac{1}{T_m} - \frac{1}{T_0}\right] + \frac{\Delta C_{pu}}{R}\left[\ln\left(\frac{T_m}{T_0}\right) + \frac{T_0}{T_m} - 1\right]\right\}}{[L_{T_m}]} \quad \text{(equation 1)}$$

where $K_L^{T_m}$=the ligand association constant at $T_m$;

$T_m$=the midpoint for the protein unfolding transition in the presence of ligand;

$T_0$=the midpoint for the unfolding transition in the absence of ligand;

$\Delta H_u^{T_0}$=the enthalpy of protein unfolding in the absence of ligand at $T_0$;

$\Delta C_{pu}$=the change in heat capacity upon protein unfolding in the absence of ligand;

$[L_{T_m}]$=the free ligand concentration at $T_m$; and

R=the gas constant.

The parameters $\Delta H_u$ and $\Delta C_{pu}$ are usually observed from differential scanning calorimetry experiments and are specific for each receptor. To calculate the binding constant from equation 1, one should have access to a differential scanning calorimetry instrument to measure $\Delta H_u$ and $\Delta C_{pu}$ for the receptor of interest. One can also locate these parameters for the receptor of interest, or a receptor closely related to it, in the literature. In these situations, equation (1) will allow the accurate measurement of $K_L$ at $T_m$.

It is also possible to calculate the ligand equilibrium association constant at any temperature, $K_L$ at T, using equation 2. To use equation 2, calorimetry data for the binding enthalpy at T, $\Delta H_L$, and the change of heat capacity upon ligand binding, $\Delta C_{pL}$ must be known (Brandts et al., *Biochemistry* 29:6927–6940 (1990)).

$$K_L^T = \qquad \text{(equation 2)}$$
$$K_L^{T_m}\exp\left\{-\frac{\Delta H_L^T}{R}\left[\frac{1}{T} - \frac{1}{T_m}\right] + \frac{\Delta C_{pL}}{R}\left[\ln\left(\frac{T}{T_m}\right) - \frac{T}{T_m} + 1\right]\right\}$$

where $K_L^T$=the ligand association constant at any temperature T;

$K_L^T$=the ligand association constant at $T_m$;

$T_m$=the midpoint for the protein unfolding transition in the presence of ligand;

$\Delta H_L^T$=the enthalpy of ligand binding in the absence of ligand at T;

$\Delta C_{pL}$ the change in heat capacity upon binding of ligand; and

R=the gas constant.

The second exponential term of equation 2 is usually small enough to be ignored so that approximate values of $K_L$ at T can be obtained using just the first exponential term:

$$K_L^T = K_L^{T_m}\exp\left\{-\frac{\Delta H_L^T}{R}\left[\frac{1}{T} - \frac{1}{T_m}\right]\right\} \quad \text{(equation 3)}$$

One need not, however, calculate binding constants according to equations 1–3 in order to rank the affinities of a multiplicity of different ligands for a receptor. The present invention provides a method for ranking affinities of ligands according to differences in thermal unfolding information for the target molecule in the presence and absence of a ligand. Thus, it is possible to obtain estimates of $K_L$ at $T_m$, even in the absence of accurate values of $\Delta H_u$, $\Delta C_{pu}$, and $\Delta H_L$.

The present invention is particularly useful for screening a combinatorial or a compound library, such as a directed diversity chemical library. To achieve high throughput screening, it is best to house samples on a multicontainer carrier or platform. A multicontainer carrier facilitates the heating of a plurality of samples simultaneously. In one embodiment, a multiwell microplate, for example a 96 or a 384 well microplate, which can accommodate 96 or 384 different samples, is used as the carrier.

In one embodiment, one sample is contained in each well of a multi-well microplate. The control well contains receptor, but no molecule to be tested for binding. Each of the other samples contains at least one molecule to be tested for binding. The thermal unfolding information for the receptor in the control well is compared to the thermal unfolding information for each of the other samples.

The rate of screening is accelerated when the sample contains more than one molecule to be tested for binding. For example, the screening rate is increased 20-fold when the sample contains a pool or collection sof 20 molecules. Samples which contain a binding molecule must then be divided into samples containing a smaller collection of molecules to be tested for binding. These divided collections must then be assayed for binding to the target molecule. These steps must be repeated until a single molecule responsible for the original thermal shift is obtained.

The element upon which the sample carrier is heated can be any element capable of heating samples rapidly and in a reproducible fashion. In the present invention, a plurality of samples is heated simultaneously. The plurality of samples can be heated on a single heating element. Alternatively, the plurality of samples can be heated to a given temperature on one heating element, and then moved to another heating element for heating to another temperature. Heating can be accomplished in regular or irregular intervals. To generate a smooth unfolding transition, the samples can be heated evenly, in intervals of 1 or 2° C. The temperature range across which the samples can be heated is from 25 to 110° C. Fluorescence readings are taken after each heating step. Samples can be heated and read by the fluorescence device in a continuous fashion. Alternatively, after each heating step, the samples may be cooled to a lower temperature prior to taking the fluorescence readings. Preferably, the samples are heated continuously and fluorescence readings are taken while the samples are being heated.

Fluorescence readings can be taken on all of the samples in the carrier simultaneously. Alternatively, readings can be taken on samples in groups of at least two at a time. Finally, the readings can be taken one sample at a time.

Figure 29:
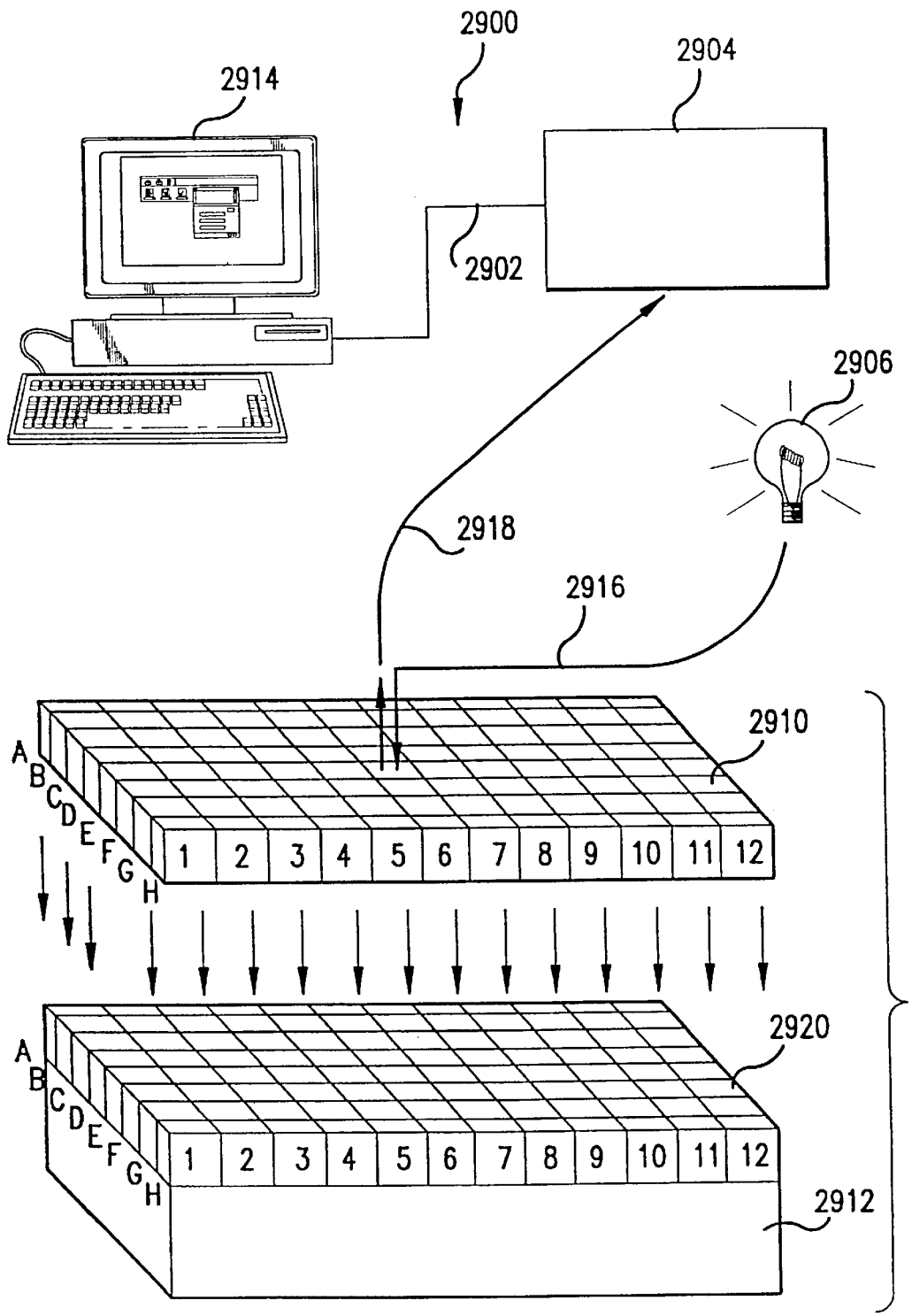
FIG. 29 shows a schematic diagram of an assay apparatus that can be used to practice the methods of present invention.
Figure 33:
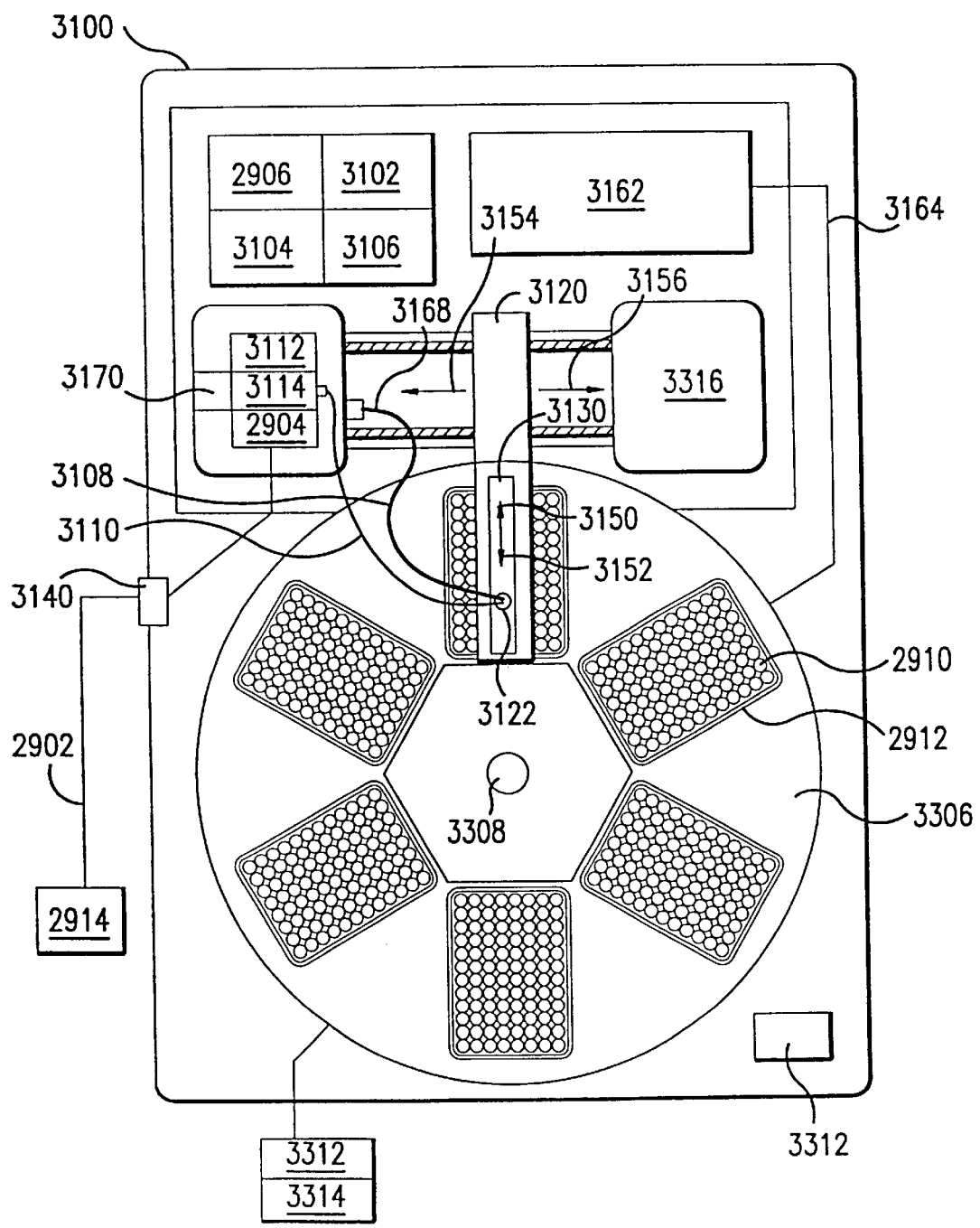
FIG. 33 is a schematic diagram illustrating a top view of another embodiment of the assay apparatus of the present invention.

In one embodiment, thermal unfolding is monitored by fluorescence using an assay apparatus such as the one shown in FIG. 29. The instrument consists of a scanner and a control software system. The system is capable of quantifying soluble and cell-associated fluorescence. Fluorescence is detected by a photomultiplier tube in a light-proof detection chamber. The software runs on a personal computer and the action of the scanner is controlled through the software. A precision X-Y mechanism scans the microplate with a sensitive fiber-optic probe to quantify the fluorescence in each well. The microplate and samples can remain stationary during the scanning of each row of the samples, and the fiber-optic probe is then is moved to the next row. Alternatively, the microplate and samples can be moved to position a new row of samples under the fiber-optic probe. The scanning system is capable of scanning 96 samples in under one minute. The scanner is capable of holding a plurality of excitation filters and a plurality of emission filters to measure the most common fluorophores. Thus, fluorescence readings can be taken one sample at a time, or on a subset of samples simultaneously. An alternate embodiment of the assay apparatus is shown in FIG. 33.

The heat conducting element or block upon which the sample carrier is heated can be any element capable of heating samples rapidly and reproducibly. The plurality of samples can be heated on a single heating element. Alternatively, the plurality of samples can be heated to a given temperature on one heating element, and then moved to another heating element for heating to another temperature. Heating can be accomplished in regular or irregular intervals. To generate a smooth thermal unfolding transition, the samples should be heated evenly, in intervals of 1 or 2° C. The temperature range across which the samples can be heated is from 4 to 110° C.

In the present invention, a plurality of samples can be heated simultaneously. If samples are heated in discrete temperature intervals, in a stairstep fashion, fluorescence readings are taken after each heating step. Alternatively, after each heating step, the samples may be cooled to a lower temperature prior to taking the fluorescence readings. Alternatively, samples can be heated in a continuous fashion and fluorescence readings are taken during heating.

The present invention also provides an improved method for generating lead compounds. After a compound or a combinatorial library of compounds has been screened using the thermal shift assay, compounds which bind to the target receptor are chemically modified to generate a second library of compounds. This second library is then screened using the thermal shift assay. This process of screening and generating a new library continues until compounds that bind to the target receptor with affinities in the $K_d$ range of from $10^{-4}$ to $10^{-15}$ M are obtained.

A fluorescence imaging system can be used to monitor the thermal unfolding of a target molecule or a receptor. Fluorescence imaging systems are well known to those skilled in the art. For example, the AlphaImager™ Gel Documentation and Analysis System (Alpha Innotech, San Leandro, Calif.) employs a high performanced charge coupled device camera with 768×494 pixel resolution. The charge coupled device camera is interfaced with a computer and images are anlayzed with Image analysis software™. The CHEMIIMAGER™ (Alpha Innotech) is a cooled charge coupled device that performs all of the functions of the ALPHAIMAGER™ and in addition captures images of chemiluminescent samples and other low intensity samples. The CHEMIIMAGER™ charge coupled device includes a Pentium processor (1.2 Gb hard drive, 16 Mb RAM), AlphaEase™ analysis software, a light tight cabinet, and a UV and white light trans-illuminator. For example, the MRC-1024 UV/Visible Laser Confocal Imaging System (BioRad, Richmond, Calif.) facilitates the simultaneous imaging of more than one fluorophore across a wide range of illumination wavelengths (350 to 700 nm). The Gel Doc 1000 Fluorescent Gel Documentation System (BioRad, Richmond, Calif.) can clearly display sample areas as large as 20×20 cm, or as small as 5×4 cm. At least two 96 well microplates can fit into a 20×20 cm area. The Gel Doc 1000 system also facilitates the performance of time-based experiments.

A fluorescence thermal imaging system can be used to monitor receptor unfolding in a microplate thermal shift assay. In this embodiment, a plurality of samples is heated simultaneously at temperatures between 25 to 110° C. A fluorescence reading is taken for each of the plurality of samples simultaneously. For example, the fluorescence in each well of a 96 or a 384 well microplate can be monitored simultaneously. Alternatively, fluorescence readings can be taken continuously and simultaneously for each sample. At lower temperatures, all samples display a low level of fluorescence. As the temperature is increased, the fluorescence in each sample increases. Wells which contain ligands which bind to the target molecule with high affinity shift the thermal unfolding $T_m$ to a higher temperature. As a result, wells which contain ligands which bind to the target molecule with high affinity fluoresce less, at a given temperature above the $T_m$ of the target molecule in the absence of any ligands, than wells which do not contain high-affinity ligands. If the samples are heated in incremental steps, the flourescence of all of the plurality of samples is simultaneoulsy imaged at each heating step. If the samples are heated continuously, the fluorescence of all of the plurality of samples is simultaneously imaged during heating.

A fluorescence thermal shift assay can be performed in a volume of 100 μL. For the following reasons, however, it is preferable to perform a thermal shift assay in a volume of 1–10 μL. First, approximately 10- to 100-fold less protein is required for the miniaturized assay. Thus, only ~4 to 40 pmole of protein are required (0.1 μg to 1.0 μg for a 25 kDa protein) for the assay (i.e. 1 to 10 μL working volume with a target molecule concentration of about 1 to about 4 μM). Thus, as little as 1 mg of protein can be used to conduct 1,000 to 10,000 assays in the miniaturized format. This is particularly advantageous when the target molecule is available in minute quantities.

Second, approximately 10- to 100-fold less ligand is required for the miniaturized assay. This advantage is very important to researchers when screening valuable combinatorial libraries for which library compounds are synthesized in minute quantities. In the case of human α-thrombin, the ideal ligand concentration is about 50 μM, which translates into 25–250 pmoles of ligand, or 10–100 ng (assuming a MW of 500 Da) of ligand per assay in the miniaturized format.

Third, the smaller working volume allows the potential of using larger arrays of assays because the miniaturized assay can fit into a much smaller area. For example, a 384 well (16×24 array) or 864 well (24×36 array) plates have the same dimensions as the 96 well plates (8.5×12.5 cm). The 384 well plate and the 864 well plate allows the user to perform 4 and 9 times as many assays, respectively, as can be performed using a 96 well plate.

Alternatively, 1536 well plates (32×48 arrays; Matrix Technologies Corp.) can be used. A 1536 well plate will facilitate sixteen times the throughput afforded by a 96 well plate. Thus, using the 1536 well plate configuration, the assay speed can be increased by about 16 times, relative to the speed at which the assay can be performed using the 96 well format. The 8×12 assay array arrangement (in a 96-well plate) facilitates the performance of 96 assays/hr, or about 2300 assays/24 hours. The 32×48 array assay arrangement facilitates the performance of about 1536 assays hr., or about 37,000 assays/24 hours can be performed using a 32×48 assay array configuration.

Alternatively, microplates containing more than 1536 wells per plate can be used in the methods of the present invention.

The assay volume can be 1–100 μL. Preferably, the assay volume is 1–50 μL. More preferably, the assay volume is 1–25 μL. More preferably still, the assay volume is 1–10 μL. More preferably still, the assay volume is 1–5 μL. More preferably still, the assay volume is 5 μL. Most preferably, the assay volume is 1 μL or 2 μL.

Preferably, the assay is performed in V-bottom polycarbonate plates or polycarbonate dimple plates. A dimple plate is a plate that contains a plurality of round-bottom wells that hold a total volume of 15 μL.

In the methods of the present invention, generation of thermal unfolding information can further comprise determining a thermal unfolding $T_m$, and the comparing step comprises comparing the $T_m$ for the target molecule in each container to (i) the $T_m$ for the target molecule in each of the other containers, and to (ii) the $T_m$ obtained for the target molecule in the absence of any of the different molecules or obtained under a reference set of biochemical conditions, and wherein the ranking step comprises ranking the efficacies of the multiplicity of different molecules or the multiplicity of different biochemical conditions according to differences in the $T_m$.

In the methods of the present invention, the measuring step comprise contacting the protein with the one or more different molecules or different biochemical conditions, in the presence of a fluorescence probe molecule present in each of the multiplicity of containers, and wherein the measuring step comprises exciting the fluorescence probe molecule, in each of the multiplicity of containers with light; and measuring the fluorescence from each of the multiplicity of containers.

In the methods of the present invention, when the target molecule is a double-stranded oligonucleotide, one strand contains a donor fluorophore and the other strand of the oligonucleotide contains an acceptor fluorophore. the contacting step can comprise contacting the oligonucleotide with the multiplicity of different molecules, or with the multiplicity of different biochemical conditions, in each of the multiplicity of containers, and wherein the measuring step exciting the donor fluorophore, in each of the multiplicity of containers, with light; and measuring the fluorescence from the acceptor fluorophore in each of the multiplicity of containers In the methods of the present invention, fluorescence can be measured in all of the containers simultaneously. Alternatively, fluorescence can be measured in a subset of the containers simultaneously. Alternatively, fluorescence can be measured one container at a time.

One alternative to taking fluorescence readings over a temperature range around the $T_m$ of the therapeutic target to obtain a full thermal unfolding curve for the ligand/target complex, in order to identify shifts in $T_m$, is to perform the assay at a single temperature near the $T_m$ of the target molecule. In this embodiment, samples that fluorescence less, relative to a control sample (containing a target molecule, but no candidate ligand) indicate that the candidate ligand binds to the target molecule.

In this embodiment, the fluorescence associated with the thermal unfolding of a target molecule resulting from heating is determined by generating thermal unfolding information for the target molecule as a function of temperature over a range of one or more discrete or fixed temperatures. The fluorescence associated with thermal unfolding, is measured. The fluorescence at the discrete or fixed temperature for the target molecule in the absence of any ligand is noted. The fluorescence in the presence of each of a multiplicity of different molecules, for example, combinatorial compounds, is measured. The fluorescence associated with thermal unfolding of the target molecule in the presence of each of the multiplicity of molecules is compared to fluorescence obtained for the target molecule at the discrete or fixed temperature in the absence of any of the multiplicity of different molecules. The affinities of the multiplicity of different molecules are ranked according to the change in the fluorescence.

The discrete or fixed temperature at which the fluorescence is measured can be any temperature that is useful for discriminating shifts in thermal stability. Preferably, the discrete or fixed temperature is the midpoint temperature $T_m$ for the target molecule in the absence of any of the multiplicity of different molecules tested for binding to the target molecule.

The methods of the present invention are not limited to assaying ligand-protein interactions. The methods of the present invention can be used to rapidly assay any multivariable system related to protein stabilization. For example, the methods of the present invention can be used to simultaneously assay the binding of more than one compound or ligand to a target molecule. Using this approach, the additive effect of multiple-ligand binding can be assessed. Positive and negative cooperativity can be determined. To accomplish this method, fluorescence thermal shift assays are performed for a target molecule, such as a protein, in the absence of any ligands, in the presence of a single ligand, and in the presence of two or more ligands. Thermal unfolding information is generated for the protein alone and for each combination of protein and ligand(s). The midpoint temperature $T_m$ is then determined for the protein alone and for each combination. Each $T_m$ is then compared to each of the other $T_m$'s for the other combinations. Alternatively, an unfolding curve is generated for the protein alone and for each combination, and each thermal unfolding curve is compared to each of the other thermal unfolding curves. In either of these manners, the additive contribution of more than one ligand to binding interaction or to protein stability can be determined.

In a similar fashion, the additive contributions of one or more biochemical conditions to protein stability can be determined. Thus, the present invention can be used to rapidly identify biochemical conditions that optimize protein stabililty, and hence shelf-life of a protein. Further, the methods and the assay apparatus of the present invention can be used to rank the efficacies of various biochemical conditions for refolding or renaturing an unfolded or denatured protein. This embodiment addresses the need in the art for a reliable method for screening for effective refolding or renaturing conditions.

For example, expression of recombinant DNA in a bacterial cell usually results in the sequestration of recombinant protein into bacterial inclusion bodies (Marston, F. A. O., Biochem. J. 240:1–12 (1986)). Although other expression systems can be used instead of bacterial expression systems, expression in bacterial cells remains the method of choice for the high-level production of recombinant proteins (Rudolph, R., Protein Engineering: Principles and Practices, pp. 283–298, John Wiley & Sons (1995)). In many cases, recovery of recombinant protein requires that protein be isolated from inclusion bodies. Protein purification from inclusion bodies process necessitates the denaturation of recombinant protein. As a result, recombinant protein must be renatured or refolded under conditions suitable to generate the protein in its native, fully functional form.

In each of these cases, denatured protein must be renatured or refolded in order to be useful for further study or use. Unfortunately, one cannot easily predict the exact conditions under which a given protein or fragment of the protein should be renatured. Each protein is different. One must always resort to testing a number of different combinations of renaturing conditions before one can know which set of conditions is optimal. Thus, it is desirable to have a reliable and rapid method for ranking the efficacies of various renaturing conditions.

Recombinant DNA technology has allowed the biosynthesis of a wide variety of heterologous polypeptides of interest in relatively large quantities through the recruitment of the bacterial protein expression apparatus. However, the promise of cheap and abundant supplies of correctly folded rare human proteins of high therapeutic value expressed in E. coli has foundered due to the overwhelmingly predominant aggregation of unfolded or partially unfolded target proteins into insoluble protein inclusion bodies. For recent reviews, see Rudolph, R., & Lilie, H., FASEB J. 10:49–56 (1995); Sadana, A., Biotechnology & Bioengineering 48:481–489 (1995); Jaenicke, R., Phil. Trans. Royal Soc. London Ser. B-Biol. Sci. 348:97–105 (1995)). Reasons for the prevailing self aggregation reaction in E. coli have centered on the relatively high concentration of the heterologous protein (as high as 30% of the weight of the cell) found to various degrees in partially unfolded states. Thus, at the elevated protein concentrations of an overexpressing E. coli strain, the exposed hydrophobic residues of unfolded proteins are more likely to encounter other molecules with similarly exposed groups (inter-molecular reaction) than they are to sample self collapsed polypeptide conformations where these hydrophobic residues are packed in a proper orientation (intra-molecular transition state) for proceeding to the fully folded native state (see FIG. 26). From this perspective, the insoluble protein inclusion bodies are seen as kinetically trapped side reaction products that thwart the preferred protein folding process.

Techniques for isolating inclusion bodies, purifying recombinant protein from inclusion bodies, and techniques for refolding or renaturing protein are well known to those skilled in the art. For example, see Sambrook, J. et al., Molecular Cloning: a Laboratory Manual, pp. 17.37–17.41, Cold Spring Harbor Laboratory Press (1989); Rudolph, R. et al., FASEB J. 10:49–56 (1995).

Another impediment to producing large quantities of correctly folded proteins in E. coli is that the reducing redox potential of the E. coli cytosol impedes the formation of disulfide bonds in vivo. The formation of disulfide bonds is an important co- and post-translational event in the biosynthesis of many extracellular proteins that is often coupled to protein folding. In addition, the cistrans proline isomerization reaction has been demonstrated to be a rate determining step for correct folding of certain proteins (Lin, L.-N., & Brandts, J. F., Biochemistry 22:564–573 (1983)). As a result, partially folded intermediates accumulate in sufficient quantity in vivo that they aggregate and precipitate into protein masses.

Cells employ a class of host proteins called molecular chaperonins that assist in vivo protein folding by apparently preventing many of the unproductive side reactions discussed above with regard to inclusion body formation, i.e. aggregation and improper disulfide bond formation. However, the E. coli chaperonin machinery, which is comprised in part by the proteins, GroEL and GroES, presumably becomes overwhelmed by massive overexpression. Despite many attempts to correct this chaperonin deficit by co-expression of molecular chaperonins with the protein of interest (Rudolph, R., & Lilie, H., The FASEB J. 10:49–56 (1995)) positive results have been reported in only one case (Goloubinoff, P., et al., Nature 342:884–889 (1989)).

Two hypotheses have been promoted to explain how GroEL and GroES assist in vivo protein folding. Under the first hypothesis, the Anfinsen cage hypothesis, the function of a molecular chaperonin is to provide a protected environment where folding of the protein to its native state can proceed without interference by pro-aggregation conditions in the cell (Martin, et al., Nature 352:36–42 (1991); Ellis, R. J., Current Biology 4:633–635 (1994)). Under the second hypothesis, the "iterative annealing" hypothesis, the function of the chaperonin is to partly unfold misfolded proteins (that is, kinetically trapped intermediates) with some of the energy of ATP hydrolysis being channeled into the conformational energy of the substrate polypeptide, forcing the polypeptide into a higher energy state from which it could once again attempt to refold correctly after being released into solution (Todd, M. J. et al., Science 265:659–666 (1994); Jackson, et al., Biochemistry 32:2554–2563 (1993); Weissman, J. S., et al., Cell 78:693–702 (1994); Weissman, J. S., & Kim, P. S., Science 253:1386–1393 (1991)).

The in vivo results discussed above are in many ways consistent with the more recent experiences with in vitro refolding of recombinant heterologous proteins expressed in E. coli. That is, while the primary amino acid sequence of a protein may contain sufficient information to determine its native folded conformation (Anfinsen, C. B., Science 181:223–230 (1973)), the biochemical conditions in which the folding reaction takes place can strongly influence the partitioning between unfolded, aggregated, and correctly folded forms.

For example, pH can be understood to influence the folding reaction by its effect on the long range electrostatic interactions summed in the fourth term of the equation (4).

$$\Delta G_{fold} = \Delta G_{conf} + \Sigma \Delta g_{i,int} + \Sigma \Delta g_{i,s} + \Delta W_{el} + (\Delta G_{bind}) \quad \text{Equation (4)}$$

where
- $\Delta G_{conf}$ = conformational free energy (order/disorder term);
- $\Delta g_{i,int}$ = short range interactions (H-bonds, van der Walls interactions, salt bridges, cofactor binding, etc.);
- $\Delta g_{i,s}$ = short range interactions with solvent (hydrophobic effect, hydration of ions, etc.); and
- $\Delta W_{el}$ = long range electrostatic interactions.
- $\Delta G_{bind}$ = ligand binding free energy As the pH of a protein solution is lowered below the pI for the protein, functional groups on the polypeptide become increasingly protonated, to the point where the electrostatic repulsion between functional groups eventually out balances the other terms in the free energy equation (equation (4)), and the protein is no longer able to adopt the native conformation.

Another important biochemical parameter for protein folding is the solvent, water, which repels aliphatic and aromatic side chains (and possibly the main chain to some extent) to minimize their exposed surface area. The influence of solvent over the folding reaction is summed in the third term of the free energy equation (equation (4)). Certain salts are known to increase the hydrophobic interaction among protein side chains in water solutions. The effect depends upon the nature of the ions following the Hofmeister series: Cations: $Mg^{2+} > Li^+ > Na^+ > K^+ > NH_4^+$. Anions: $SO_4^{2-} > HPO_4^{2-} > $ acetate $>$ citrate $>$ tartrate $> Cl^- > NO_3^- > ClO_3^- > I^- > ClO_4^- > SCN^-$. Stabilizing Hofmeister anions, such as $SO_4^{2-}$ and $HPO_4^{2-}$ at 0.4 M have been found to increase the yield of correctly folded proteins (Creighton, T. E., In: *Proteins: Structures and Molecular Properties*, Freeman, New York, (1984)). This favorable outcome for the native conformation of the protein has been attributed to the cations' and anions' "salting out" effect which leads to the preferential hydration of the protein (Creighton, T. E., In: *Proteins: Structures and Molecular Properties*, Freeman, New York, (1 984)).

Glycerol alters the solvation properties of water to favor the native conformation of proteins. The mechanism by which this occurs is the co-solvent exclusion and preferential hydration of the protein, not unlike the effect of salts of the salts of the Hofmeister series (Timasheff & Arakawa, In: *Protein Structure, A Practical Approach*, T. E. Creighton, ed., IRL Press, Oxford, UK (1989), pp. 331–354).

Another example of how the environment influences protein folding is the effect that known ligands and cofactors have on the yield of folded protein. Ligand binding has the effect of shifting the equilibrium from an unfolded state to a native-ligand complex through a coupling of the binding free energy to that of the folding reaction. The role of metal ions in the refolding of bovine carbonic anhydrase II has been described (Bergenhem & Carlsson, *Biochim. Biophys. Acta* 998:277–285 (1989)). Other biochemical parameters that have been shown to affect protein folding are: protein concentration, temperature, glutathione redox buffers (GSH, GSSG), the presence of detergents, and the presence of other additives, such as glycerol, arginine-HCl, polyethylene glycol (PEG), and organic solvents.

During incubation under refolding conditions, recombinant proteins can be immobilized to solid phase support. This configuration resembles the "Anfinsen cage" hypothesis for the function of GroEL and GroES where an unfolded protein becomes temporarily immobilized in a protected environment where folding to the native state can proceed without interference from competing aggregation reactions.

Confirmation of protein folding on solid supports has now come from two recent reports in the literature. A polyhistidine tagged TIMP-2 protein could be refolded by dialysis while still bound to a metal chelate column (Negro, A. et al., *FEBS Lett.* 360:52–56 (1995)). A polyionic fusion peptide attached to the amino or carboxyl terminus of α-glucosidase allowed folding while bound to heparin-Sepharose resin at about 5 mg/mL (Rudolph & Lilie, *FASEB J.* 10:49–56 (1995)). A polyionic arginine tag metholdology for immobilizing and refolding α-glucosidase is disclosed in Stempfer, G. et al., *Nature Biotechnology* 14:329–334 (1996).

In the present invention, the thermal shift assay is used to rank the efficacy of various refolding or renaturing conditions. Each of a multiplicity of aliquots of a protein of interest, which has been incubated under a variety of different biochemical folding conditions, are placed in a container in a multicontainer carrier. An aliquot of the native, fully functional protein of known concentration. is placed in the control container. The samples can be placed in any multicontainer carrier. Preferably, each sample can be placed in a well of a multiwell microplate.

In considering the many biochemical variables that can influence the outcome of the protein folding reaction, optimization of protein folding is a multi-variable optimization problem, not unlike protein crystallization and quantitative structure activity relationships (QSAR) in drug discovery. Multi-variable optimization problems require large numbers of parallel experiments to collect as much data as possible in order to influence a favorable response. In this regard, both protein crystallization and QSAR analyses have greatly benefited from mass screening protocols that employ matrix arrays of incremental changes in biochemical or chemical composition.

The present invention can be used to rank the efficacies of refolding or renaturing conditions. Such conditions include, but are not limited to, the concentration of glycerol, the concentration of protein, the use of agents which catalyze the formation of disulfide bond formation, temperature, pH, ionic strength, type of solvent, the use of thiols such as reduced glutathione (GSH) and oxidized glutathione (GSSG), chaotropes such as urea, guanidinium chlorides, alkyl-urea, organic solvents such as carbonic acid amides, L-arginine HCl, Tris buffer, polyethylene glycol, nonionic detergents, ionic detergents, zwitterionic detergents, mixed micelles, and a detergent in combination with cyclodextrin. The present invention can be used regardless of whether a denaturation agent is removed from the protein using dialysis, column chromatographic techniques, or suction filtration.

Using a fluorescence thermal shift assay, the conditions which facilitate optimal protein refolding can be determined rapidly. In this embodiment, the renatured protein samples and a control protein sample (i.e., a sample of native protein in its fully functional form) are heated over a temperature range. At discrete temperature intervals, a fluorescence reading is taken. Alternatively, fluorescence readings can be taken during a continuous, pre-determined temperature profile. Thermal unfolding information (for example, thermal unfolding $T_m$) is generated for each sample. The $T_m$ for the native, fully functional reference protein is determined. The relative efficacies of the refolding conditions are ranked according to the magnitude of the fluorescence associated with unfolding at the $T_m$ of the native, fully functional reference protein, relative to the magnitude of the fluorescence of a known quantity of the sample proteins in the biochemical conditions at that $T_m$. The magnitude of fluorescence intensity change is used to monitor protein unfolding (reflected on the ordinate, or y-axis, of a thermal unfolding curve) is proportional to the amount of correctly folded protein.

The present invention provides a method for screening biochemical conditions that facilitate and optimize protein folding. To screen conditions for a given protein, it is first necessary to determine the thermal unfolding profile for a protein of interest. This is accomplished by generating thermal unfolding information using the microplate thermal shift assay. Various conditions can be optimized, including pH optimum, ionic strength dependence, concentration of salts of the Hofineister series, glycerol concentration, sucrose concentration, arginine concentration, dithiothreitol concentration, metal ion concentration, etc.

Figure 27:
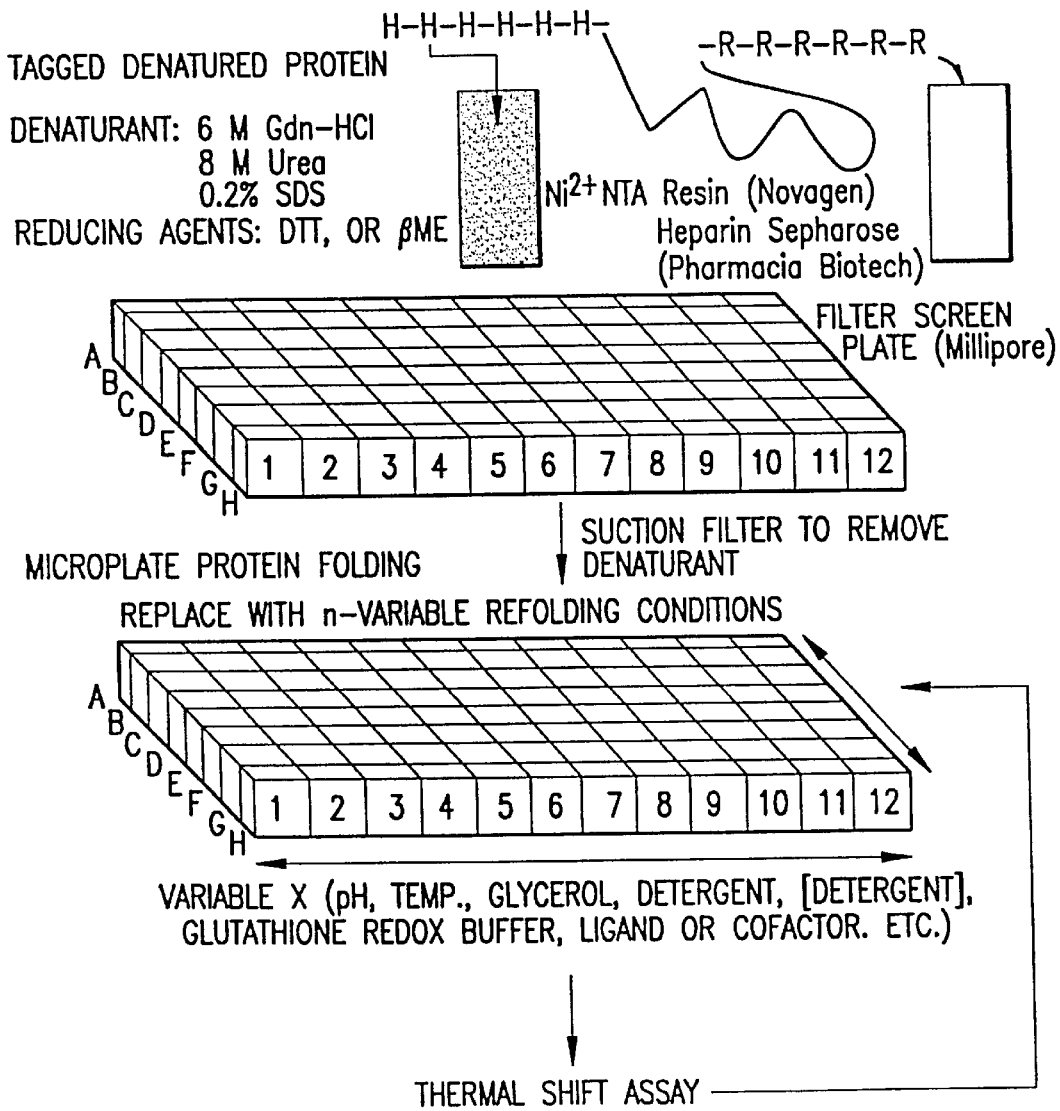
FIG. 27 is a schematic diagram of a method of screening biochemical conditions that optimize protein folding.

Using the microplate thermal shift assay, one can determine one or more biochemical conditions have an additive effect on protein stability. Once a set of biochemical conditions that facilitate an increase in protein stability have been identified using the thermal shift assay, the same set of conditions can be used in protein folding experiments with recombinant protein. See FIG. 27. If the conditions that promote protein stability in the thermal shift assay correlate with conditions that promote folding of recombinant protein, conditions can be further optimized by performing additional thermal shift assays until a combination of stabilizing conditions that result in further increase protein stability are identified. Recombinant protein is then folded under those conditions. This process is repeated until optimal folding conditions are identified. Protein stability is expected to correlate with improved yields of protein folding. Yield of correctly folded protein can be determined using any suitable technique. For example, yield of correctly folded protein can be calculated by passing refolded protein over an affinity column, for example, a column to which a ligand of the protein is attached, and quantifying the amount of protein that is present in the sample. In this way, folding conditions can be assessed for their additive contributions to correct folding. The transition state for the protein folding reaction resembles the native form of the protein more than the denatured form. This has been demonstrated to be the case for may proteins (Fersht, A. R., *Curr. Op. Struct. Biol.* 7:3–9 (1997)).

The methods and the apparatus of the present invention provide a rapid, high throughput approach to screening for combinations of biochemical conditions that favor the protein folding. The method does not require cumbersome and time consuming steps that conventional approaches to protein folding require. For example, using the method of the present invention, it is not necessary to dilute protein to large volumes and low protein concentrations (~10 μg/mL) in order to avoid aggregation problems associated with conventional methods of recombinant protein refolding. Suppression of protein aggregation will allow for screening biochemical parameters that shift the protein folding equilibrium (between the unfolded and the folded forms of proteins) to the correct native conformation.

Like protein stabilization, protein folding, ligand selection, and drug design, selection of conditions that promote protein crystallization is another multi-variable optimization problem that is solved using the methods and the apparatus of the present invention.

The methods of the present invention are also useful for determining conditions that facilitate protein crystallization. The crystallization of molecules from solution is a reversible equilibrium process, and the kinetic and thermodynamic parameters are a function of the chemical and physical properties of the solvent system and solute of interest (McPherson, A., In: *Preparation and Analysis of Protein Crystals*, Wiley Interscience (1982); Weber, P. C., *Adv. Protein Chem.* 41:1–36 (1991)) 1991). Under supersaturating conditions, the system is driven toward equilibrium where the solute is partitioned between the soluble and solid phase instead of the unfolded and native states. The molecules in the crystalline phase pack in ordered and periodic three dimensional arrays that are energetically dominated by many of the same types of cohesive forces that are important for protein folding, i.e. van der Waals interactions, electrostatic interactions, hydrogen bonds, and covalent bonds (Moore, W. J., In: *Physical Chemistry*, 4th Ed., Prentice Hall, (1972), pp. 865–898).

Thus, in many ways protein crystallization can be viewed as a higher level variation of protein folding where whole molecules are packed to maximize cohesive energies instead of individual amino acid residues. Moreover, for both protein crystallization and protein folding, the composition of the solvent can make very important contributions to the extent of partitioning between the soluble (unfolded) and crystalline (native) forms. The cohesive interactions present in protein macromolecules and the role played by solvent in modulating these interactions for both protein folding and protein crystallization are complex and not fully understood at the present time. In this regard, biochemical conditions that promote protein stabililty and protein folding also promote protein crystallization.

For example, biochemical conditions that were found to increase the stability of D(II) FGF receptor 1 (FIGS. 19–24) correlate with the conditions that facilitated the crystallization of x-ray diffraction quality protein crystals. Conditions that were employed to obtain crystals of D(II) FGFR1 protein are shown in Table 1.

Protein crystals were obtained in the pH range 7.4 to 9.2 in the presence of the Hofmeister salt $Li_2SO_4$ (65 to 72%). These crystallization conditions correlated with the pH optimum of about 8.0 in FIG. 23. Other salts of the Hofmeister series such as $Na_2SO_4$, $(NH_4)_2SO_4$ and $Mg_2SO_4$ were also found useful as additives for lowering the amount of $Li_2SO_4$ required as the precipitant. Clearly, these conditions for successful D(II) FGFR1 crystallization correlate closely with the stabilizing conditions that were identified using the microplate thermal shift assay.

Conditions that were identified as facilitating human α-thrombin stabilization also facilitate human α-thrombin protein crystallization. FIGS. 17A–D and 18 show the results of microplate thermal shift assays of conditions that facilitate human α-thrombin stability. Table 2 contains a summary of the conditions identified by three different investigators that facilitate crystallization of x-ray diffraction quality human α-thrombin crystals (Bode, W., et al., *Protein Sci.* 1:426–471 (1992); Vijayalakshmi, J. et al., *Protein Sci.* 3:2254–22271 (1994); and Zdanov, A. et al., *Proteins: Struct. Funct. Genet.* 17:252–265 (1993)).

The conditions summarized in Table 2 correlate closely with the conditions identified in the microplate thermal shift assay as facilitating human α-thrombin stability. Crystals formed near a pH optimum of about 7.0. Furthermore, there is a clear preference for the presence of 0.1 to 0.5 M NaCl (50% of the conditions) or 0.1 to 0.2 M $NaHPO_4$. This is consistent with the recently discovered $Na^+$ binding site (Dang et al., *Nature Biotechnology* 15:146–149 (1997)) and microplate thermal shift assay results in FIGS. 17A–D and 18. All of the human α-thrombin samples described in Table 2 that have yielded good crystals are complexed with a ligand, thereby further stabilizing the native structure of this protein beyond that acquired from the biochemical conditions.

TABLE 1

D(II) FGFR1 Crystallization Conditions

| Buffer | Precipitant | Additive | Protein Concentration |
|---|---|---|---|
| 50 mM Hepes pH 7.4 | 72% Li2SO4 | | 10 mg/ml (10 mM Hepes pH 7.5) |
| 50 mM Hepes pH 7.4 | 72% Li2SO4 | 3.4 mM ZnSO4 | 10 mg/ml (10 mM Hepes pH 7.5) |
| 50 mM Hepes pH 7.4 | 68% Li2SO4 | 1% PEG 8000 | 10 mg/ml (10 mM Hepes pH 7.5) |
| 50 mM Hepes pH 7.4 | 66% Li2SO4 | 3.4 mM Na2SO4 | 10 mg/ml (10 mM Hepes pH 7.5) |
| 50 mM Hepes pH 7.4 | 66% Li2SO4 | 5.3 mM (NH4)2SO4 | 10 mg/ml (10 mM Hepes pH 7.5) |
| 50 mM Hepes pH 7.4 | 66% Li2SO4 | 2.1 mM MgSO4 | 10 mg/ml (10 mM Hepes pH 7.5) |
| 10 mM Tris Hcl, pH 8.0 | 65% Li2SO4 | | 10 mg/ml (10 mM Hepes pH 7.5) |
| 20 mM glycine, pH 5.2 | 68% Li2SO4 | | 10 mg/ml (10 mM Hepes pH 7.5) |

Protein crystallization is a slow and tedious process that has historically been the rate determining step for the x-ray diffraction determination of protein and nucleic acid structures. The method and apparatus of the present invention facilitate the rapid, high-throughput elucidation of conditions that promote the stability of a given protein and thus the formation of X-ray quality protein crystals.

When a protein is more stable, it has fewer thermodynamic motions that inhibit packing into a crystal lattice. With fewer motions, the protein fits better into a crystal lattice. Using conventional crystallization methods, crystallization experiments are set up at room temperature for weeks at a time. Over time, protein unfolding occurs. Using the methods of the present invention, conditions that stabilize a protein are examined over a temperature range.

In a further aspect of the present invention, an assay apparatus is provided that includes a heating means for simultaneously heating a plurality of samples, and a receiving means for receiving fluorescence from the samples while the samples are being heated. In yet a further aspect of the present invention, an assay apparatus is provided that includes a temperature adjusting means for simultaneously adjusting a temperature of a plurality of samples in accordance with a pre-determined temperature profile, and a receiving means for receiving fluorescence from the samples while the temperature of the samples is adjusted in accordance with the temperature profile.

In yet a further aspect, the present invention also provides an assay apparatus that includes a movable platform on which are disposed a plurality of heat conducting blocks. The temperature of the heat conducting blocks, and their samples, are adjusted by a temperature adjusting means. Each of the plurality of heat conducting blocks is adapted to receive a plurality of samples. A light source is provided for emitting an excitatory wavelength of light for the samples. While the temperature of the samples is being adjusted, a sensor detects the fluorescence from the samples in response to the excitatory wavelength of light. The movable platform is moved between heat conducting blocks to sequentially detect fluorescence from the samples in each of the plurality of heat conducting blocks.

The assay apparatus of the present invention is directed to an automated temperature adjusting and fluorescence receiving system that simultaneously adjusts the temperature of a multiplicity of samples over a defined temperature range and receives fluorescence from the samples. The assay apparatus of the present invention is particularly useful for performing microplate thermal shift assays of protein stability. The assay apparatus of the present invention can be used to practice all of the methods of the present invention.

TABLE 2

| Human α-thrombin Complex | Crystallization Conditions | | | | | |
|---|---|---|---|---|---|---|
| | Buffer | Salt | Precipitant | Additive | Protein Conc. | Comment |
| | Vijayalakshmi et al. | | | | | |
| MDL-28050 | 75 mM NaHPO4 pH 7.3 | 0.375 M NaCl | | 1 mM NaN3 | 3 mg/ml | protein (2.2 Å) |
| | 100 mM NaHPO4 pH 7.3 | | 24% PEG 4000 | 1 mM NaN3 | | well |
| Hirugen/Hirulog 1 | 50 mM NaHPO4 pH 7.3 | 0.375 M NaCl | | .5 mM NaN3 | 3–3.7 mg/ml | protein (2.3 Å) |
| | 0.1 M NaHPO4 pH 7.3 | | 28% PEG 8000 | 1 mM NaN3 | | well |
| FPAM + Hirugen | 0.1 M NaHPO4 pH 7.3 | | | | 5 mg/ml | protein (2.5 Å) |
| | 0.1 M NaHPO4 pH 7.3 | | 28% PEG 8000 | | | well |
| Hirulog 3 | 75 mM NaHPO4 pH 7.3 | 0.38 M NaCl | | 1 mM NaN3 | 5 mg/ml | protein (2.3 Å) |
| | 0.1 M NaHPO4 pH 7.3 | | 24% PEG 8000 | 1 mM NaN3 | | well |
| | Bode et al. | | | | | |
| NAPAP | 0.1 M KHPO4 pH 8.0 | | | | 10 mg/ml | protein (2.3 Å) |
| | 0.1 M KHPO4 pH 8.0 | | 1.9 M NH4SO4 | | | |
| PPACK | 2 mM MOPS pH 7 | 0.1 M NaCl | | 0.5% NaN3 | 10 mg/ml | protein (1.9 Å) |
| | 0.2 M PO4 pH 6–7 | 0.5 M NaCl | 20% PEG 6000 | | | well |
| | Zdanov et al. | | | | | |
| Hirutonin-2 | 50 mM NaHPO4 pH 5.5 | 0.1 M NaCl | | | 10 mg/ml | protein (2.1 Å) |
| | 0.1 M Na Citrate pH 5.5 | 0.1 M NaCl | 24% PEG 4000 | | | well |

FIG. 29 shows a schematic diagram of one embodiment of an assay apparatus 2900 of the present invention. Assay apparatus 2900 includes a heat conducting block 2912 that includes a plurality of wells 2920 for a plurality of samples 2910. Heat conducting block 2912 is composed of a material that has a relatively high coefficient of thermal conductivity, such as aluminum, stainless steel, brass, teflon, and ceramic. Thus, heat conducting block 2912 can be heated and cooled to a uniform temperature but will not be thermally conductive enough to require excess heating or cooling to maintain a temperature.

Assay apparatus 2900 also includes a light source 2906 for emitting an excitatory wavelength of light, shown generally at 2916, for the samples. Light source 2906 excites samples 2910 with excitatory light 2916. Any suitable light source can be used. For example a tungsten-halogen lamp can be used. Alternatively, a Xenon-arc lamp, such as the Biolumin 960 (Molecular Dynamics) can used. Alternatively, a high pressure mercury (Hg) Lamp can be used. High pressure mercury lamps emit light of higher intensity than Xenon (Xe) lamps. The intensity of light from a high pressure mercury lamp is concentrated in specific lines, and are only useful if the Hg lines are at suitable wavelengths for excitation of particular fluorophores. Other types of light sources that could be used include, a light-emitting diode, a light-emitting diode array, a laser diode, or a laser diode array.

Some fluorescence plate readers employ lasers for excitation in the visible region of the electromagnetic spectrum. For example, the FluorImager™ (Molecular Dynamics, Palo Alto, Calif.) is such a device. This technology is useful when using fluorescent dyes that absorb energy at around 480 nm and emit energy at around 590 nm. Such a dye could then be excited with the 488 nm illumination of standard argon, argon/krypton lasers. For example, 1,1-dicyano-2-[6-(dimethylamino)naphthalen-2-yl]propene (DDNP) is such a dye. The advantage in using a laser is that a laser is characterized by very high intensity light, which results in an improved signal to noise ratio.

Excitatory light 2916 causes fluorescence 2918 from samples 2910.

Fluorescence 2918 is received by a photomultiplier tube 2904. Photomultiplier tube 2904 is communicatively and operatively coupled to a computer 2914 by an electrical connection 2902. Computer 2914 functions as a data analysis means for analyzing fluorescence as a function of temperature.

As discussed above, the fluorescence receiving means or sensor of the assay apparatus of the present invention can comprise a photomultiplier tube. Alternatively, the fluorescence receiving means or sensor can include a charge coupled device or a charge coupled device camera. In still another alternative, the fluorescence receiving means or sensor can include a diode array.

For measuring fluorescence in the microplate thermal shift assay, one. alternative to a fluorescence plate reader is a charge coupled device (CCD). For example, high resolution CCD cameras can detect very small amounts of electromagnetic energy, whether it originates from distance stars, is diffracted by crystals, or is emitted by fluorophores. A CCD is made of semi-conducting silicon. When photons of light fall on it, free electrons are released. As an electronic imaging device, a CCD camera is particularly suitable for fluorescence imaging because it can detect very faint objects, affords sensitive detection over a broad spectrum range, affords low levels of electromagnetic noise, and detects signals over a wide dynamic range—that is, a charge coupled device can simultaneously detect bright objects and faint objects. Further, the output is linear so that the amount of electrons collected is directly proportional to the number of photons received. This means that the image brightness is a measure of the real brightness of the object, a property not afforded by, for example, photographic emulsions.

Figure 30:
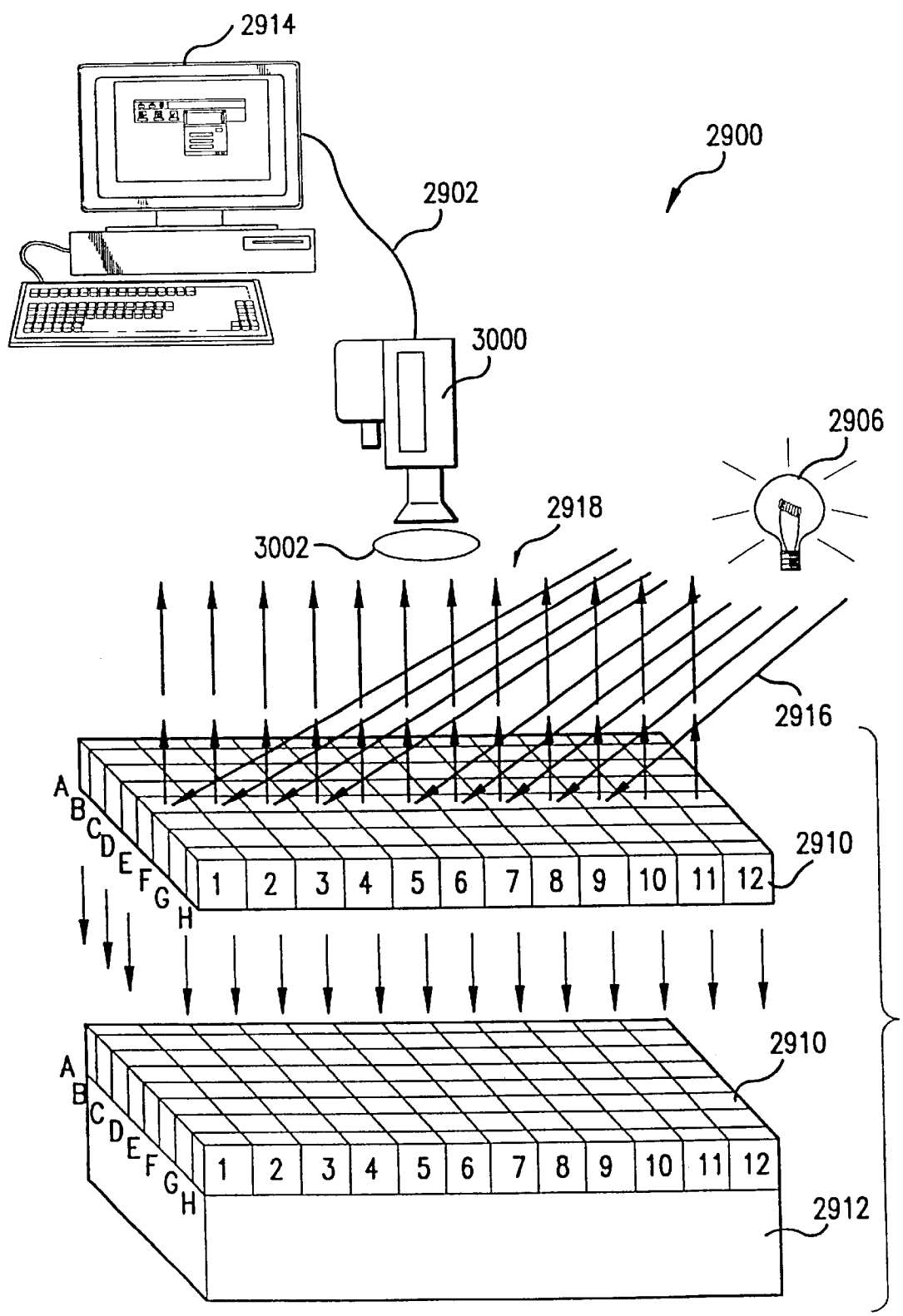
FIG. 30 shows a schematic diagram of another embodiment of the assay apparatus that can be used to practice the methods of present invention.

FIG. 30 depicts a charge coupled device (CCD) camera 3000 for detecting fluorescence 2918 from samples 2910. CCD camera 3000 can be any CCD camera suitable for imaging fluorescence. For example, suitable CCD cameras are available from Alpha-Innotech (San Leandro, Calif.), Stratagene (La Jolla, Calif.), and BioRad (Richmond, Calif.). Particularly preferred is a cooled CCD camera, such as a liquid cooled CCD camera, or a CCD camera cooled by a thermoelectric coolant system.

When a fluorescence imaging camera or a CCD camera is used, excitatory light 2916 can be a suitable lamp that is positioned over the plurality of samples 2910. Alternatively, excitatory light 2916 can be a suitable lamp that is positioned under the plurality of samples 2910. In another alternative embodiment, excitatory light 2916 can be delivered to each sample 2910 by a plurality of fiber optic cables. Each fiber optic cable is disposed through one of a plurality of tunnels in conducting block 2912. Thus, each of samples 2910 receives excitatory light 2916 through a fiber optic cable.

As shown in FIG. 30, source 2906 excites samples 2910 with excitatory light 2916. Excitatory light 2916 causes fluorescence 2918 from samples 2910. fluorescence 2918 is filtered through an emission filter 3002. Emission filter 3002 filters out wavelengths of fluorescence 2918 that are not to be monitored or received by CCD camera 3000. Preferably, the emission filter is an optical filter. CCD camera 3000 receives the filtered fluorescence 2918 from all of samples 2910 simultaneously. For simplicity and ease of understanding, only fluorescence form one row of samples 2910 are shown in FIG. 30. CCD camera 3000 is communicatively and operatively coupled to computer 2914 by electrical connection 2902.

Figure 31:
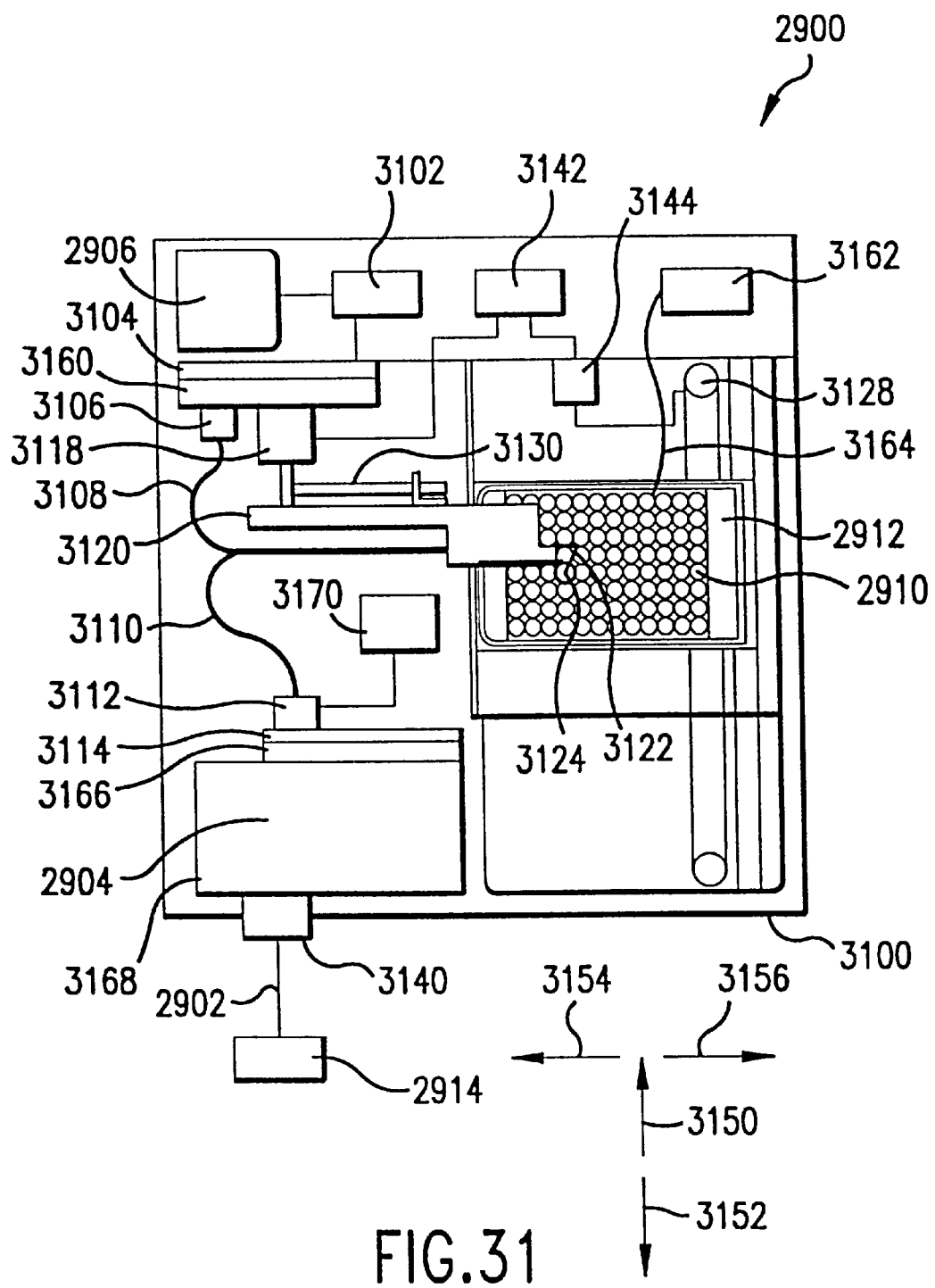
FIG. 31 shows a schematic diagram of another embodiment of the assay apparatus that can be used to practice the methods of present invention.

With reference now to FIG. 31, one embodiment of assay apparatus 2900 is shown in more detail. As shown in FIG. 31, many apparatus components are attached to a base 3100. A heat conducting block relative movement means 3128 is used to move heat conducting block 2912 in directions 3150 and 3152. Heat conducting block relative movement means 3128 is communicatively and operatively connected to a servo controller 3144. Activation of heat conducting block relative movement means 3128 by servo controller 3144 moves heat conducting block 2912 in directions 3150 and 3152. Servo controller 3144 is controlled by a computer controller 3142. Alternatively, computer 2914 could be used to control servo controller 3144.

A sensor is removably attached to a sensor armature 3120. An exemplary sensor is a fiber optic probe 3122. Fiber optic probe 3122 includes a fiber optic cable capable of transmitting excitatory light 2916 to samples 2910, and a fiber optic cable capable of receiving fluorescence 2918 from samples 2910. Electromagnetic radiation is transmitted from excitatory light source 2906 to fiber optic probe 3122 by excitatory light input fiber optic cable 3108. In one embodiment of the present invention, a fluorescence receiving means comprising photomultiplier tube 2904 is used to detect fluorescence from samples 2910. In this embodiment, electromagnetic radiation is transmitted from fiber optic probe 3122 to photomultiplier tube 2904 by fiber optic cable 3110. In an alternative embodiment of the present invention, CCD camera 3002 is used to detect fluorescence from samples 2910. In this embodiment, fiber optic cable 3110 is not required.

A temperature sensor 3124 is removably attached to sensor armature 3120. Temperature sensor 3124 is communicatively and operably linked to a temperature controller 3162. Temperature sensor 3124 monitors the temperature of heat conducting block 2912 and feeds temperature information back to temperature controller 3162. Temperature controller 3162 is connected to heat conducting block 2912 by a thermoelectric connection 3164. Under the action of temperature controller 3162, the temperature of heat conducting block 2912 can be increased, decreased, or held constant. Particularly, the temperature of heat conducting block 2912 can be changed by temperature controller 3162 in accordance with a predetermined temperature profile. Preferably, temperature computer controller 3162 is implemented using a computer system such as that described below with respect to FIG. 37.

As used herein, the term "temperature profile" refers to a change in temperature over time. The term "temperature profile" encompasses continuous upward or downward changes in temperature, both linear and non-linear changes. The term also encompasses any stepwise temperature change protocols, including protocols characterized by incremental increases or decreases in temperature during which temperature increases or decreases are interrupted by periods during which temperature is maintained constant. In the apparatus of the present invention, the temperature profile can be pre-determined by programming temperature computer controller 3162. For example, temperature profiles can be stored in a memory device of temperature controller 3162, or input to temperature controller 3162 by an operator.

A sensor armature relative movement means 3130 is used to move sensor armature 3120 in directions 3154 and 3156. A sensor armature servo controller 3118 is fixedly connected to excitatory light filter housing 3160. Activation of sensor armature servo controller 3118 moves fiber optic probe 3122 in directions 3154 and 3156. It would be readily apparent to one of ordinary skill in the relevant art how to configure servo controllers to move heat conducting block 2912 and sensor armature 3120. It should be understood that the present invention is not limited to the use of servo controllers for movement of heat conducting block 2912 and sensor armature 3120, and other suitable means known to one of skill in the art can also be used, such as a motor.

Servo controllers 3118 and 3144 are both communicatively and operatively connected to computer controller 3142. Computer controller 3142 controls the movement of sensor armature 3120 in directions 3154 and 3156. In addition, computer controller 3142 controls the movement of heat conducting block relative movement means 3128 in directions 3150 and 3152.

In the assay apparatus of the present invention, excitatory light source 2906 is used to excite samples 2910. Excitatory light source 2906 is communicatively and operably connected to excitatory light filter 3104, which is contained within excitatory light filter housing 3160. Preferably, the excitation filter is an optical filter. Excitatory light filter 3104 filters out all wavelengths of light from excitatory light source 2906 except for the wavelength(s) of light that are desired to be delivered by fiber optic probe 3122 to samples 2910. An excitatory light filter servo controller 3106 controls the aperture of excitatory light filter 3104. Excitatory light source 2906 and excitatory light filter servo controller 3106 are communicatively and operatively connected to excitatory light computer controller 3102. Computer controller 3102 controls the wavelength of excitatory light transmitted to samples 2910 by controlling excitatory light filter servo controller 3106. Excitatory light 2916 is transmitted through excitatory light input fiber optic cable 3108 to fiber optic probe 3122 for transmission to samples 2912.

Fluorescence 2918 from samples 2910 is received by fiber optic probe 3122 and is transmitted to fluorescence filter 3114 by output fiber optic cable 3110. fluorescence filter 3114 is contained within a fluorescence filter housing 3166. Fluorescence filter housing 3166 is disposed on photomultiplier tube housing 3168. Photomultiplier tube housing 3168 contains photomultiplier tube 2904. A fluorescence servo controller 3112 controls the aperture of foluorescence filter 3114, thereby controlling the wavelength of fluorescence 2918 that is transmitted to photomultiplier tube 2904. Fluorescence servo controller 3112 is controlled by a computer controller 3170.

Fluorescence 2918 from samples 2910 is transmitted from photomultiplier tube 2904. Electrical output 3140 connects photomultiplier tube 2904 to electric connection 2902. Electric connection 2902 connects electrical output 3140 to computer 2914. Driven by suitable software, computer 2914 processes the fluorescence signal from samples 2910. Exemplary software is a graphical interface that automatically analyzes fluorescence data obtained from samples 2910. Such software is well known to those of ordinary skill in the art. For example, the CytoFluor™II fluorescence multi-well plate reader (PerSeptivé Biosystems, Framingham, Mass.) utilizes the Cytocalc™ Data Analysis System (PerSeptive Biosystems, Framingham, Mass.). Other suitable software includes, MicroSoft Excel or any comparable software.

Figure 32A:
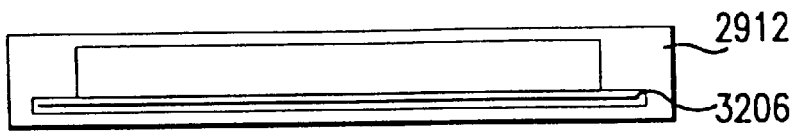
FIGS. 32A–E illustrate one embodiment of a thermal electric stage for the assay apparatus of the present invention.
Figure 32B:
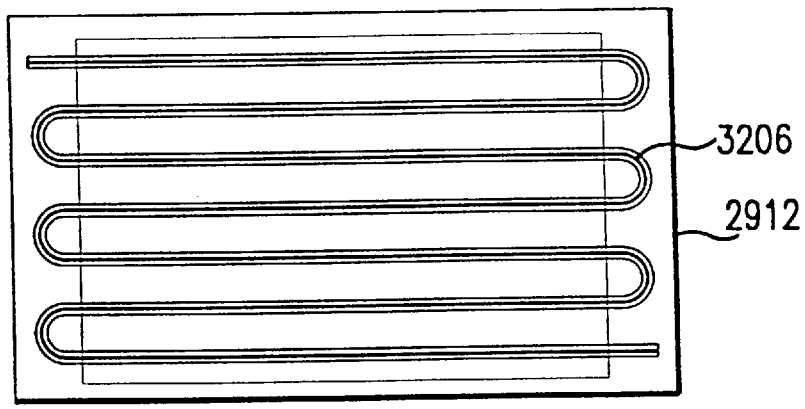
Figure 32C:

FIGS. 32A–C illustrate one embodiment of a thermal electric stage or heat conducting block for the assay apparatus of the present invention. FIG. 32A shows a side view of heat conducting block 2912 and a heat conducting wire 3206. FIG. 32B shows a top view of heat conducting block 2912 and heat conducting wire 3206. Heat conducting wire 3206 is a temperature adjusting element that adjusts the temperature of heat conducting block 2912. By means readily known to one of skill in the art, temperature controller 3162 causes heat conducting wire 3206 to increase or decrease in temperature, thereby changing the temperature of heat conducting block 2912. For example, an exemplary temperature controller is a resistance device that converts electric energy into heat energy. Alternatively, the heating element can be a circulating water system, such as that disclosed in U.S. Pat. No. 5,255,976, the content of which is incorporated herein by reference. In another alternative, the temperature adjusting element can be a heat conducting surface upon which heat conducting block 2912 is disposed. Particularly, the temperature of heat conducting wire 3206 can be changed by temperature controller 3162 in accordance with a pre-determined temperature profile. Temperature controller 3162 is preferably implemented using a computer system such as that described below with respect to FIG. 37. Alternatively, computer 2914 could be used to implement temperature controller 3162. An exemplary set of specifications for temperature controller 3162 and heat conducting block 2912 is as follows:

| resolution | 0.1° C. |
|---|---|
| accuracy | +0.5° C. |
| stability | 0.1° C. |
| repeatability | 0.1° C. |

Temperature controller 3162 changes temperature in accordance with a temperature profile as discussed below with respect to FIGS. 36A and 36B.

The temperature of heat conducting block 2912 can be controlled such that a uniform temperature is maintained across the heat conducting block. Alternatively, the temperature of heat conducting block 2921 can be controlled such that a temperature gradient is established from one end of the heat conducting block to the other. Such a technique is disclosed in U.S. Pat. Nos.5,255,976 and 5,525,300, the entirety of both of which is incorporated by reference.

Heat conducting block 2912 is preferably configured with plurality of wells 2920 for samples 2910 to be assayed. In one embodiment, each of wells 2920 is configured to receive a container containing one of plurality of samples 2910. Alternatively, heat conducting block 2912 is configured to receive a container containing plurality of samples 2910. An exemplary container for containing plurality of samples 2910 is a microtiter plate.

Figure 32D:
Figure 32E:

In yet a further alternate embodiment, heat conducting block 2912 is configured to receive a heat conducting adaptor that is configured to receive a container containing one or more of samples 2910. The heat conducting adaptor is disposed on heat conducting block 2912, and the container containing samples 2910 fits into the heat conducting adaptor. FIGS. 32C-E show three exemplary configurations of a heat conducting adaptor. An adaptor 3200 is configured with round-bottomed wells. An adaptor 3202 is configured with square-bottom wells. An adaptor 3204 is configured with V-shaped wells. For example, adaptor 3200 can receive a plurality of round-bottom containers, each containing one sample. Similarly, adaptor 3202 can receive a plurality of square-bottom containers, and adaptor 3204 can contain a plurality of V-shaped bottom containers. Adaptors 3200, 3202, and 3204 can also receive a carrier for a multiplicity of round-bottom containers. An exemplary carrier is a microtitre plate having a plurality of wells, each well containing a sample. When heat conducting block 2912 is heated, heat conducting adaptors 3200, 3202, or 3204 are also heated. Thus, the samples contained in the containers that fit within adaptors 3200, 3202, or 3204 are also heated. Adaptors 3200, 3202, and 3204 can accept standard microplate geometries.

Another embodiment of the assay apparatus of the present invention is shown in FIG. 33. In this embodiment, a plurality of heat conducting blocks 2912 is mounted on a rotatable platform or carousel 3306. Alternativeley, the platform can be a translatable platform. Platform or carousel 3306 can be composed of a heat conducting material, such as the material that heat conducting block 2912 is composed of. Although six heat conducting blocks are shown in FIG. 33, this number is exemplary and it is to be understood that any number of heat conducting blocks can be used. As shown in FIG. 33, an axle 3308 is rotatably connected to base 3100. Rotatable platform 3306 is axially mounted to rotate about axle 3308. Rotation of axle 3308 is controlled by a servo controller 3312. Servo controller 3312 is controlled by a computer controller 3314 in a manner well known to one of skill in the relevant arts. Computer controller 3314 causes servo controller 3312 to rotate axle 3308 thereby rotating rotatable platform 3306. In this manner, heat conducting blocks 2912 are sequentially placed under fiber optic probe 3122.

Each of the plurality of heat conducting blocks 2912 can be controlled independently by temperature controller 3162. Thus, the temperature of a first heat conducting block 2912 can be higher or lower than the temperature of a second heat conducting block 2912. Similarly, the temperature of a third heat conducting block 2912 can be higher or lower than the temperature of either first or second heat conducting block 2912.

In a manner similar to that described above for FIG. 31, relative movement means 3130 is also used to move sensor armature 3120 in directions 3150 and 3152 so that fiber optic probe 3122 can be moved to detect fluorescence from samples 2910. A second sensor armature relative movement means 3316 is used to move sensor armature 3120 in directions 3154 and 3156.

The temperature of heat conducting blocks 2912 is controlled by temperature controller 3162. Temperature controller 3162 is connected to rotatable platform 3306 by connection 3164 to heat conducting blocks 2912. Under the action of temperature controller 3162, the temperature of heat conducting blocks 2912 can be increased and decreased. Alternatively, temperature controller 3162 can be configured to adjust the temperature of rotatable platform 3306. In such a configuration, when rotatable platform 3306 is heated, heat conducting blocks 2912 are also heated. Alternatively, the temperature of each of heat conducting blocks 2912 can be controlled by a circulating water system such as that noted above.

In a manner similar to that illustrated in FIG. 31, excitatory light source 2906 is used to excite samples 2910. Excitatory light source 2906 is communicatively and operably connected to excitatory light filter 3104, which is contained within excitatory light filter housing 3160. Excitatory light filter 3104 filters out all wavelengths of light from excitatory light source 2906 except for the wavelength (s) of light that are desired to be delivered by fiber optic probe 3122 to samples 2910. An excitatory light filter servo controller 3106 controls the aperture of excitatory light filter 3104. Excitatory light source 2906 and excitatory light filter servo controller 3106 are communicatively and operatively connected to excitatory light computer controller 3102. Computer controller 3102 controls the wavelength of excitatory light transmitted to samples 2910 by controlling excitatory light filter servo controller 3106. Excitatory light 2916 is transmitted through excitatory light input fiber optic cable 3108 to fiber optic probe 3122 for transmission to samples 2912.

Fluorescence 2918 from samples 2910 is received by fiber optic probe 3122 and is transmitted to fluorescence filter 3114 by fiber optic cable 3110. Fluorescence servo controller 3112 controls fluorescence filter 3114 aperture and thus controls the wavelength of fluorescence that is transmitted to photomultiplier tube 2904. In a manner similar to that explained for FIG. 31, fluorescence servo controller 3112 is controlled by computer controller 3170.

The assay apparatus of the present invention can detect fluorescence from samples 2910 one sample at a time or simultaneously from a subset of samples 2910. As used herein, the term "subset of samples" refers to at least two of samples 2910. To detect fluorescence simultaneously from a subset of samples in an embodiment of the assay apparatus of the present invention comprising photomultiplier tube 2904, a plurality of excitatory light filters 3104, excitatory light input fiber optic cables 3108, emission light output fiber optic cables 3110, and emission light filters 3114 must be used.

The fluorescence signal is transmitted from photomultiplier tube 2904 to computer 2914. Photomultiplier tube 2904 is communicatively and operatively coupled to computer 2914 by electrical connection 2902. Connection 2902 is connected to photomultiplier tube 2904 through electrical output 3140. Computer 2914 functions as a data analysis means for analyzing fluorescence as a function of temperature.

Figure 34:
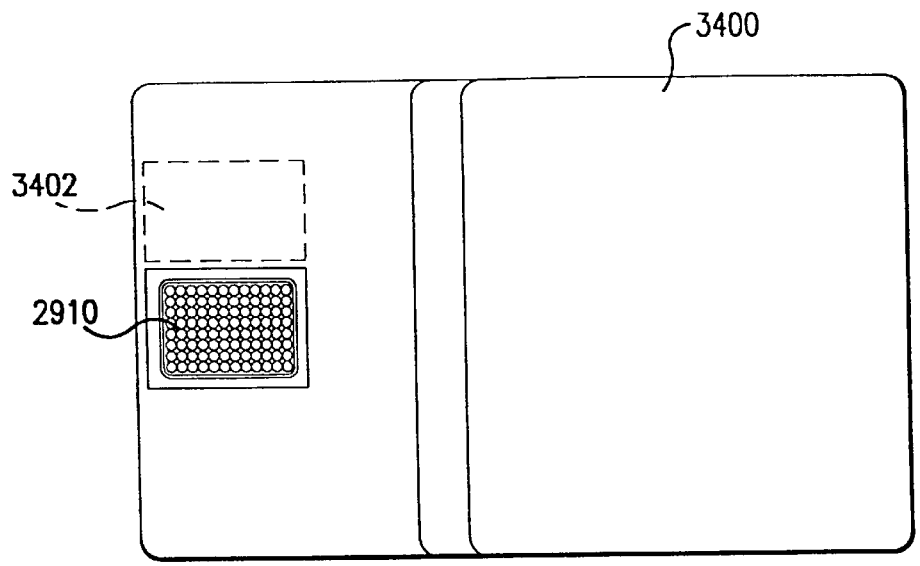
FIG. 34 is a schematic diagram illustrating the top view of the embodiment of the assay apparatus shown in FIG. 33 with a housing installed.
Figure 35:
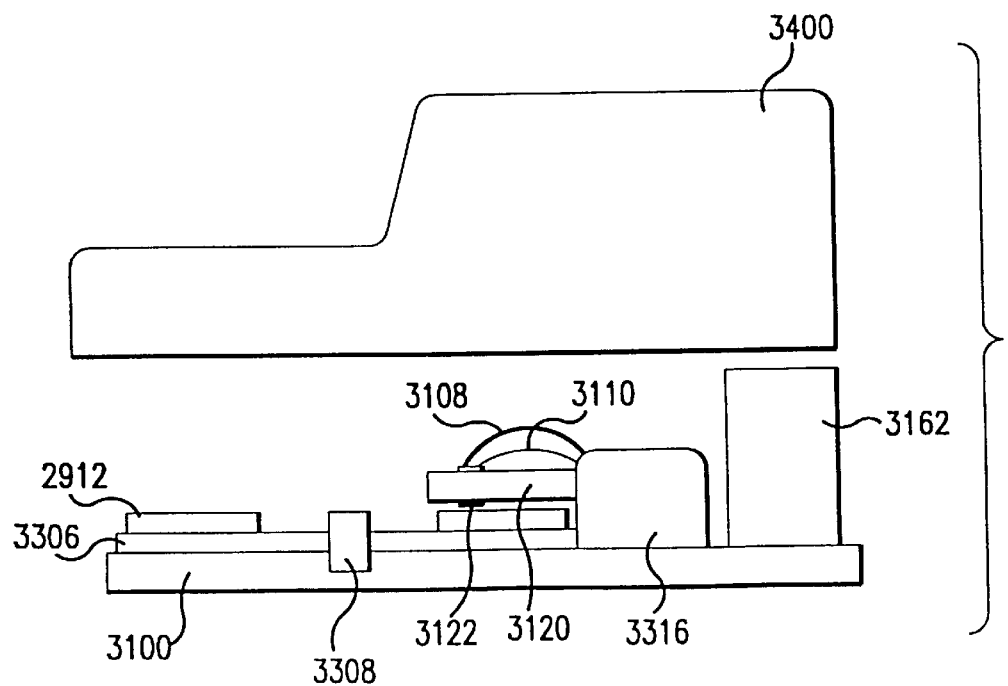
FIG. 35 is a schematic diagram illustrating a side view of the embodiment of the assay apparatus shown in FIGS. 33 and 34.

FIG. 34 illustrates a top view of the assay apparatus shown in FIG. 33 with a housing 3400 that covers the apparatus. A door 3402 opens to reveal samples 2910. Door 3402 can be a hinge door that swings open. Alternatively, door 3402 can be a sliding door that slides open. A side view of the assay apparatus shown in FIGS. 33 and 34 is illustrated in FIG. 35. Cover 3400 is disposed on top of base 3100. Cover 3400 can be made of any suitable material. For example, cover 3400 can be made of plexiglass, fiberglass, or metal.

Figure 36A:
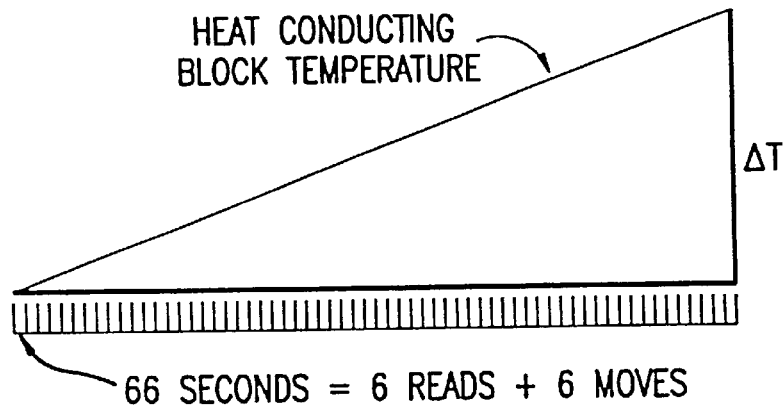
FIGS. 36A and 36B illustrate a temperature profile and how the temperature profile is implemented using the automated assay apparatus of the present invention.
Figure 36B:
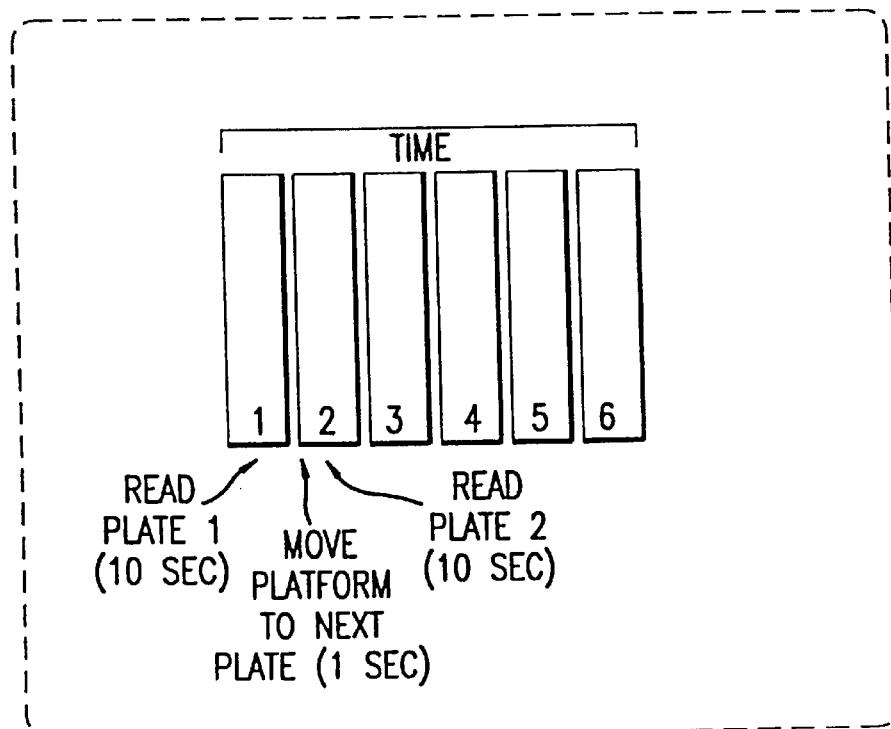

FIGS. 36A and 36B illustrate a temperature profile and how the temperature profile is implemented using the assay apparatus of the present invention. FIG. 36A illustrates a temperature profile 3600 that shows the temperature of heat conducting blocks 2912 as a function of time. Heat conducting blocks 2912 and samples 2910 are heated in a continuous fashion in accordance with temperature profile 3600. Alternatively, rotatable platform 3306 can be heated along with heat conducting blocks 2912. Preferably, temperature profile 3600 is linear, with temperatures ranging from about 4° C. to about 110° C.

Alternatively, temperature profile 3600 can be characterized by incremental, stair step increases in temperature, in which heat conducting blocks 2912 and samples 2910 are heated to a predetermined temperature, maintained at that temperature for a predetermined period of time, and than heated to a higher predetermined temperature. For example, temperature can be increased from 0.5° C. to 20° C. per minute. Although the temperature range from about 4° C. to about 110° C. is disclosed, it is to be understood that the temperature range with which a given target molecule, for example, a protein, is to be heated to generate thermal unfolding information can readily be determined by one of ordinary skill in the art. The length of time over which temperature profile 3600 is accomplished will vary, depending on how many samples are to be assayed and on how rapidly the sensor that receives fluorescence 2918 can detect fluorescence 2918 from samples 2910. For example, an experiment in which each of six heat conducting blocks 2912 holds a total of 96 samples 2910 (for a total of 576 samples), and in which samples are scanned using a fluorescent reader device having a single fiber optic probe, and in which the temperature profile is from 38° C. and 76° C., would take approximately 38 minutes to perform using the apparatus shown in FIG. 33.

While heating in accordance with temperature profile 3600, fluorescence 2918 from each sample 2910 in a first heat conducting block 2912 is received through fiber optic probe 3122. As illustrated in FIG. 36B, after fluorescence from all of samples 2910 in first heat conducting block 2912 have been received, platform 3306 is rotated to move the next heat conducting block 2912 under fiber optic probe 3122 and fluorescence 2918 from samples 2910 is received by fiber optic probe 3122. This process is continued until reception of fluorescences from all samples in all heat conducting blocks 2912 is complete. Fluorescence from samples 2910 on each heat conducting block 2912 can be received one at a time, simultaneously from a subset of samples, simultaneously from one row of samples at a time, or all of the samples at one time.

Figure 38:
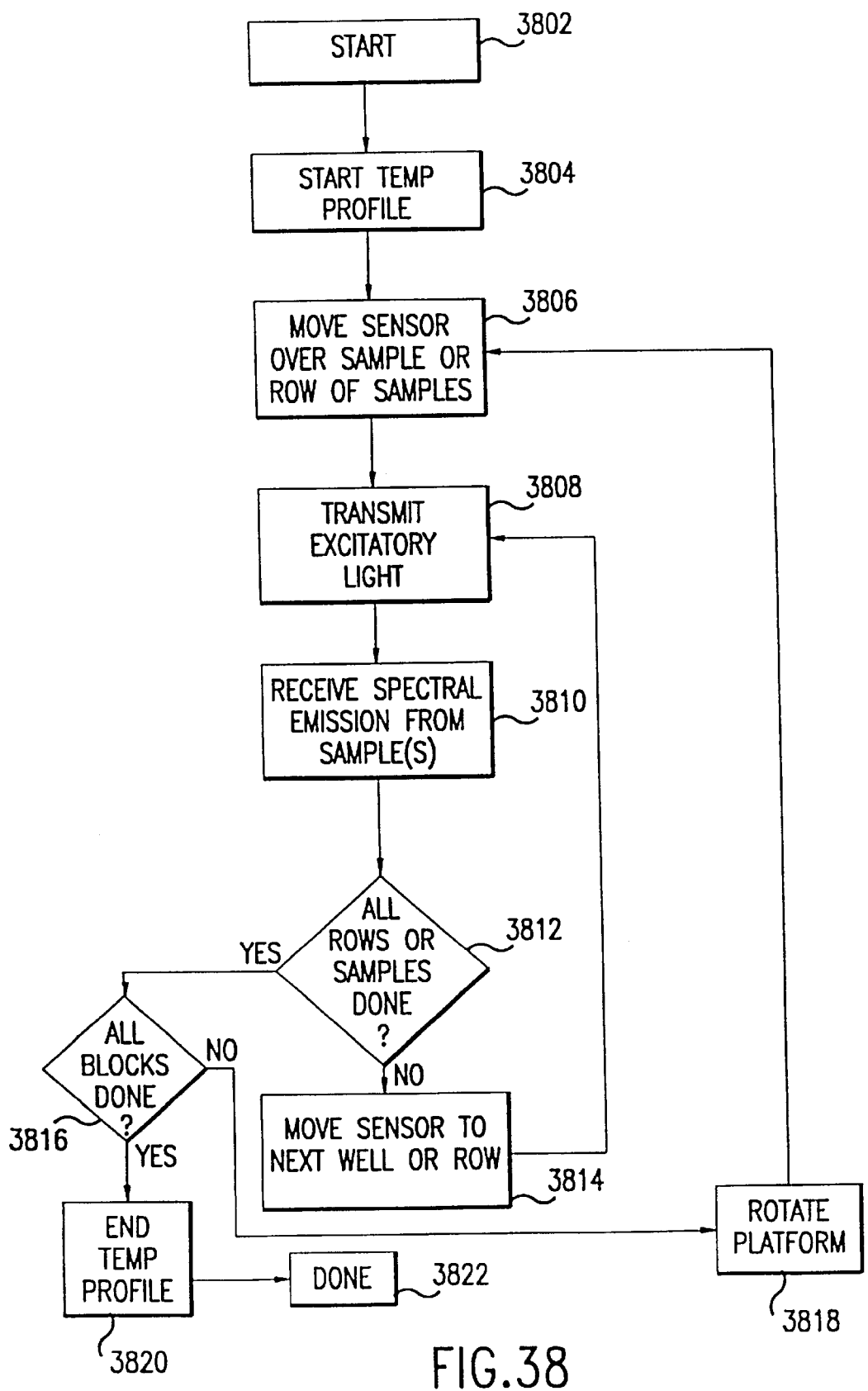
FIG. 38 shows a flow diagram illustrating one embodiment for implementation of the present invention.

The present invention may be implemented using hardware, software, or a combination thereof, and may be implemented in a computer system or other processing system. A flowchart 3800 for implementation of one embodiment of the present invention is shown in FIG. 38. Flowchart 3800 begins with a start step 3802. In a step 3804, temperature profile 3600 is initiated. For example, temperature controller 3162 causes the temperature of heat conducting block 2912 to increase. In a step 3806, a sensor such as fiber optic probe 3122 or CCD camera 3000 is moved over a sample 2910, row of samples 2910, or all of samples 2910. In a step 3808, excitatory light is transmitted to sample(s) 2910 using excitatory light source 2906. In a step 3810, fluorescence is received by the sensor from sample(s) 2910. In a decision step 3812, it is determined whether fluorescence 2918 has been received from all of the samples, rows of samples, in one heat conducting block 2912. If fluorescence 2918 has not been received from all of the samples or rows of samples, the sensor is moved over the next sample or row of samples in a step 3814. Processing then continues at step 3808 to transmit excitatory light 2916. Processing then continues to a step 3810 to receive fluorescence 2918 from sample(s) 2910.

If fluorescence 2918 has been received from all of samples or rows of samples, processing continues to a decision step 3816. In decision step 3816, it is determined whether fluorescence 2918 has been received from samples in all heat conducting blocks. If not, rotatable platform 3306 is rotated in a step 3818 to place the next heat conducting block 2912 and samples 2910 contained therein under the sensor. Steps 3806 through 3818 are followed until fluorescence 2918 has been received from all of the samples in all of heat conducting blocks 2912. Processing then continues to a step 3820, in which temperature profile 3600 is completed and processing ends at a step 3822.

Figure 39:
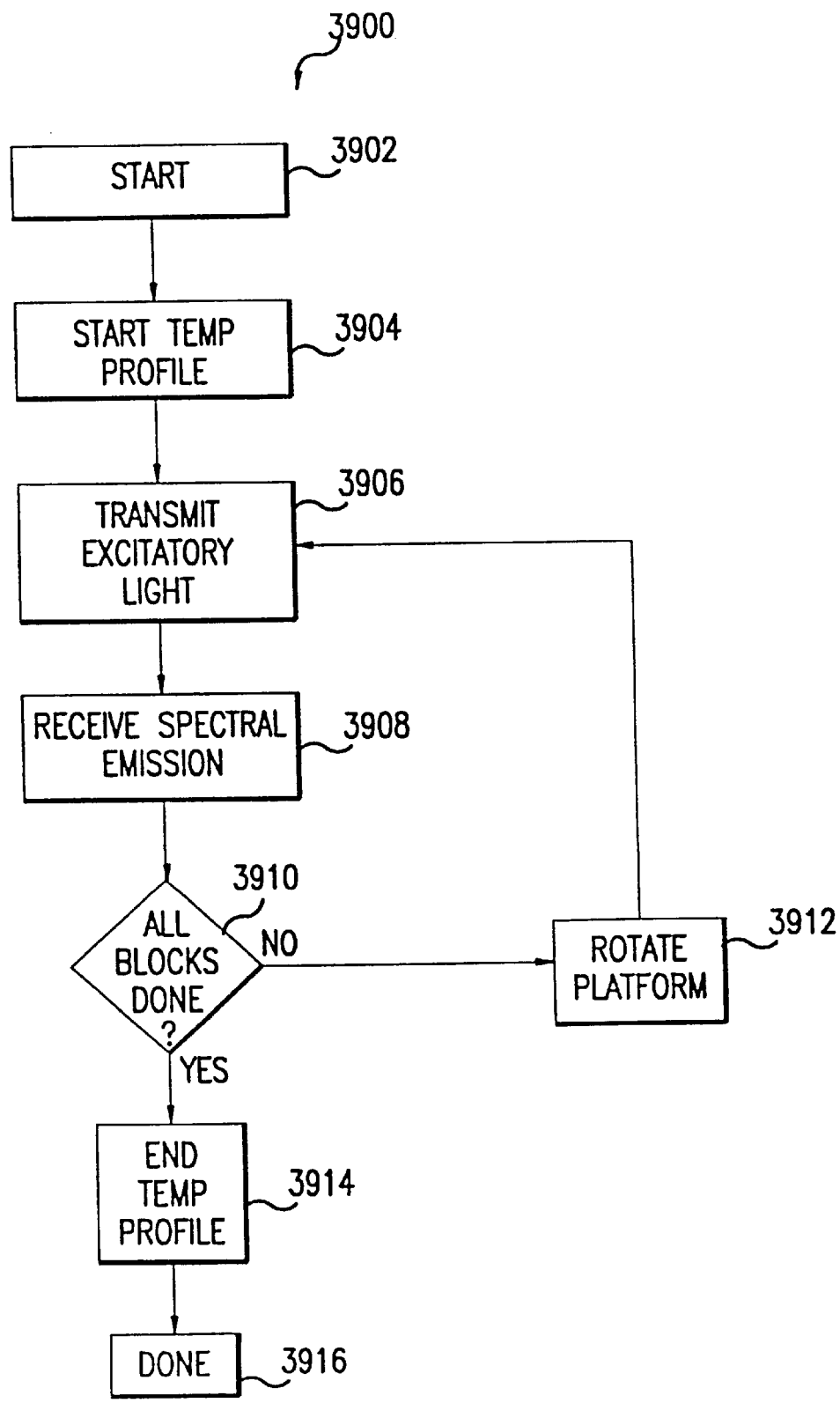
FIG. 39 shows a flow diagram illustrating an alternate embodiment for implementation of the present invention.

A flowchart 3900 for implementation of an alternate embodiment of the present invention is shown in FIG. 39. In this embodiment, a sensor for simultaneously receiving fluorescence 2918 from all of samples 2910 on heat conducting block 2912, such as CCD camera 3000, is positioned over heat conducting block 2912. Flowchart 3900 begins with a start step 3902. In a step 3904, temperature profile 3600 is initiated. For example, temperature controller 3162 causes the temperature of heat conducting block 2912 to increase. In a step 3906, excitatory light is transmitted to sample(s) 2910 using excitatory light source 2906. In a step 3908, fluorescence is received by CCD camera 3000 from sample(s) 2910. In a decision step 3910, it is determined whether fluorescence 2918 has been received from all of heat conducting blocks 2912. If not, rotatable platform 3306 is rotated in a step 3912 to place the next heat conducting block 2912 and samples 2910 contained therein under CCD camera 3000. Steps 3906 through 3912 are followed until fluorescence 2918 has been received from samples 2910 in all of heat conducting blocks 2912. Processing then continues to a step 3914. In step 3914, temperature profile 3600 is completed and processing ends at a step 3916.

Figure 37:
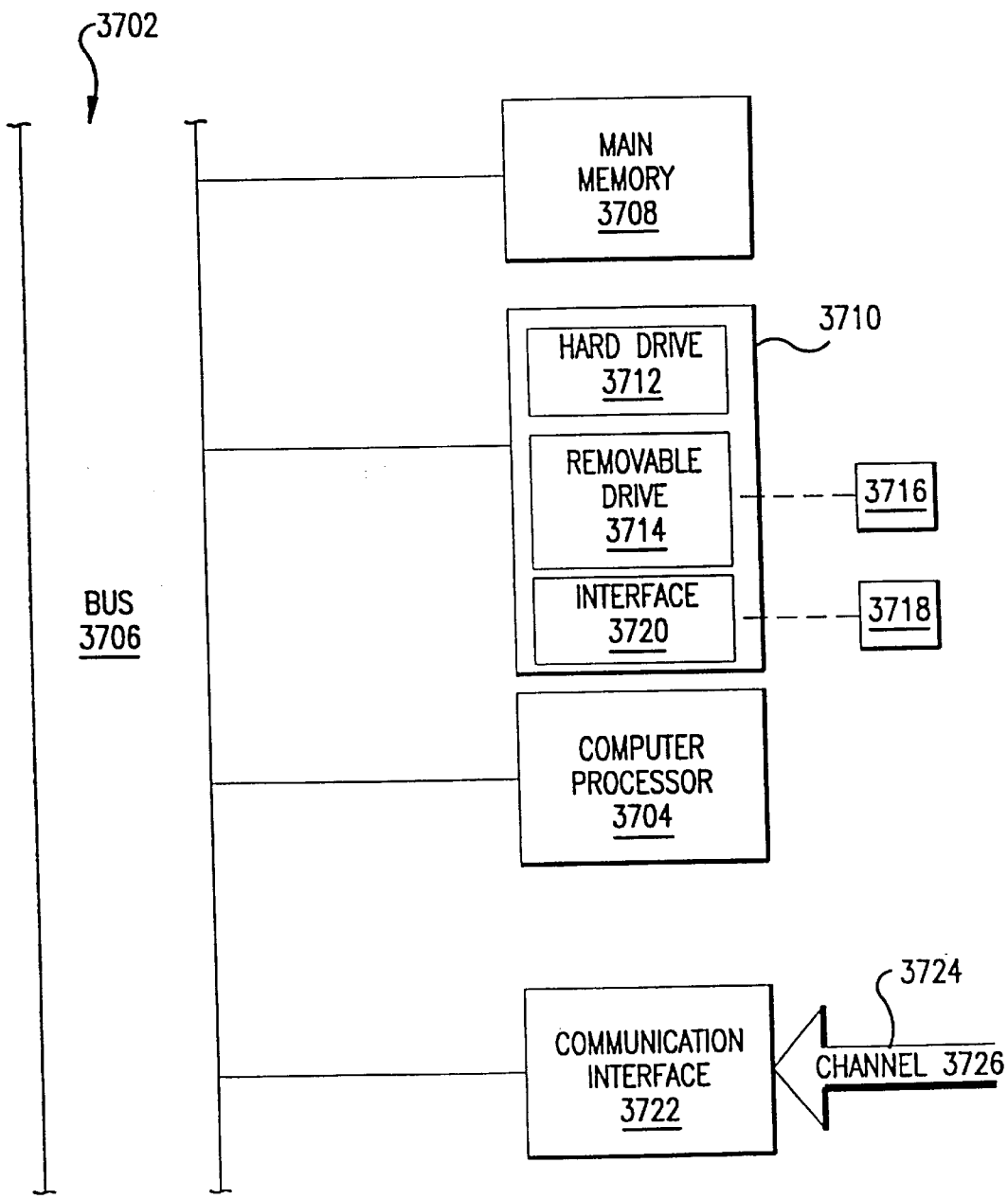
FIG. 37 shows an exemplary computer system suitable for use with an assay apparatus.

As stated above, the present invention may be implemented using hardware, software, or a combination thereof, and may be implemented in a computer system or other processing system. An exemplary computer system 3702 is shown in FIG. 37. Computer controllers 3102, 3142, 3162, 3170, or 3314, can be implemented using one or more computer systems such as computer system 3702.

After reading this description, it will become apparent to a person skilled in the relevant art how to implement the invention using other computer systems and/or computer architectures. Computer system 3702 includes one or more processors, such as processor 3704. Processor 3704 is connected to a communication bus 3706. Computer system 3702 also includes a main memory 3708, preferably random access memory (RAM), and can also include a secondary memory 3710. The secondary memory 3710 can include, for example, a hard disk drive 3712 and/or a removable storage drive 3714, representing a floppy disk drive, a magnetic tape drive, an optical disk drive, etc. The removable storage drive 3714 reads from and/or writes to a removable storage unit 3716 in a well known manner. Removable storage unit 3716 represents a floppy disk, magnetic tape, optical disk, etc. which is read by and written to by removable storage drive 3714. As will be appreciated, the removable storage unit 3716 includes a computer usable storage medium having stored therein computer software and/or data.

In alternative embodiments, secondary memory 3710 may include other similar means for allowing computer programs or other instructions to be loaded into computer system 3702. Such means can include, for example, a removable storage unit 3718 and an interface 3720. Examples of such can include a program cartridge and cartridge interface (such as that found in video game devices), a removable memory chip (such. as an EPROM, or PROM) and associated socket, and other removable storage units 3718 and interfaces 3720 which allow software and data to be transferred from the removable storage unit 3718 to computer system 3702.

Computer system 3702 can also include a communications interface 3722. Communications interface 3722 allows software and data to be transferred between computer system 3702 and external devices. Examples of communications interface 3722 can include a modem, a network interface (such as an Ethernet card), a communications port, a PCMCIA slot and card, etc. Software and data transferred via communications interface 3722 are in the form of signals 3724 which can be electronic, electromagnetic, optical or other signals capable of being received by communications interface 3722. These signals 3724 are provided to communications interface via a channel 3726. This channel 3726 carries signals 3724 and can be implemented using wire or cable, fiber optics, a phone line, a cellular phone link, an RF link and other communications channels. In the assay apparatus of the present invention, one example of channel 3726 is electrical connection 2902 that carries signal 3724 of fluorescence 2918 to computer 2914.

In this document, the terms "computer program medium" and "computer usable medium" are used to generally refer to media such as removable storage device, 3716 and 3718, a hard disk installed in hard disk drive 3712, and signals 3724. These computer program products are means for providing software to computer system 3702.

Computer programs (also called computer control logic) are stored in main memory 3708 and/or secondary memory 3710. Computer programs can also be received via communications interface 3722. Such computer programs, when executed, enable the computer system 3702 to perform the features of the present invention as discussed herein. In particular, the computer programs, when executed, enable the processor 3704 to perform the features of the present invention. Accordingly, such computer programs represent controllers of the computer system 3702.

In an embodiment where the invention is implemented using software, the software may be stored in a computer program product and loaded into computer system 3702 using removable storage drive 3714, hard drive 3712 or communications interface 3722. The control logic (software), when executed by the processor 3704, causes the processor 3704 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Having now generally described the invention, the same will become more readily understood by reference to the following specific examples which are included herein for purposes of illustration only and are not intended to be limiting unless otherwise specified.

EXAMPLE 1

Ranking Ligands that Bind to The Active Site of Human α-thrombin

Using the computer controlled process DirectedDiversity® (see U.S. Pat. No. 5,463,564), scientists at 3-Dimensional Pharmaceuticals, Inc. have generated a combinatorial library of compounds directed at the active site of human α-thrombin. Approximately 400 compounds were synthesized and assayed by a conventional spectrophotometric kinetic assay in which succinyl-Ala-Ala-Pro-Arg-p-nitroanilide (Bachem, King of Prussia, Pa.) served as substrate. Five of these compounds, which are characterized by $K_i$'s that span almost four orders of magnitude in binding affinity, were used to test the range and limits of detection of the thermal shift assay. These five proprietary compounds are listed in Table 3, along with the $K_i$ for each respective compound, as measured by the kinetic assay (last column). $K_i$'s for these compounds ranged from 7.7 nM for 3dp-4026 to 20.0 $\mu$M for 3dp-3811.

A stock human α-thrombin solution (1.56 mg/mL) from Enzyme Research Labs was first diluted to 0.5 mg/mL (11 $\mu$M) with 50 mM Hepes, pH 7.5, 0.1 M NaCl (assay buffer, unless mentioned otherwise), and stored on ice. The five ligands (recrystallized solids characterized by mass spectrometry and NMR) were accurately weighed out to be 1.5 to 2.0 mg and dissolved in 1.0 mL of 100% DMSO so that the concentration was between 1.8 and 3.8 mM. A 96 well V-bottom Costar microplate was then set up such that 100 $\mu$L of the 11 $\mu$M human α-thrombin solution was pipetted into wells A1 through A6. This was followed by the addition of 2 $\mu$L of 3dp-3811 into well A2, 2 $\mu$L of 3dp-3959 into well A3, 2 $\mu$L of 3dp-4077 into well A4, 2 $\mu$L of 3dp-4076 into well A5, 2 $\mu$L of 3dp-4026 into well A6, and 2 $\mu$L of 100% DMSO into control well A1. The contents were mixed by repeated uptake and discharge using a 100 $\mu$L pipette tip. Finally, one drop of mineral oil (Sigma, St. Louis, Mo.) was added on top of the wells to reduce evaporation of samples at elevated temperatures. The microplate was then placed on heating block 4 of a RoboCycler Gradient 96 Temperature Cycler (Stratagene, La Jolla, Calif.), set at 25° C., for 1 minute. The plate was then placed into a SPECTRAmax™ 250 spectrophotometer (set to 30° C.) and the absorbance at 350 nm was measured for each sample. This reading served as the blank or reference from which all the other readings at higher temperatures were compared. The assay was initiated by setting heating block 1 to 38° C., programming the temperature cycler to move the microplate to heating block 1, and keeping the microplate there for 3 minutes. Following the equilibration at 38° C., the plate was moved to the 25° C. block (Block 4) for 30 seconds, inserted in the spectrophotometer, and absorbance was read at 350 nm. The microplate was then put back into the temperature cycler and was moved to heating block 2, which had been pre-equilibrated at 40° C. After 3 minutes at 40° C., the plate was returned to 25° C. (on block 4) for 30 seconds, and was returned to the spectrophotometer for a measurement of absorbance at 3 50 nm. This process was repeated 18 more times until the temperature had been raised to 76° C. in 2° C. increments. After subtraction of the blank absorbance ($A_{350}$ at 25° C.), turbidity, reflected in the absorbance value, was plotted as a function of temperature. The thermal denaturation curves for this experiment are shown in FIG. 1.

The control (in well A1), which contained only 11 μM human α-thrombin in 2% DMSO, was found to undergo a thermal denaturation transition starting at ~50° C., as reflected in the large increase in $A_{350}$. The midpoint in this transition was observed to be ~55° C. This result was consistent with differential scanning calorimetric measurements for bovine prothrombin 1, which revealed a denaturation transition at $T_m$=58° C. (Leniz, B. R. et al., Biochemistry 33:5460–5468 (1994)). The thermal denaturation curves for all of the tested inhibitor compounds displayed a shift in the transition towards higher temperatures. 3dp-4026 showed the largest shift in $T_m$: ~9° C. This result is consistent with the fact that, among the compounds tested, 3 dp-4026 exhibited the greatest binding affinity, as judged by kinetic measurements with succinyl-Ala-Ala-Pro-Arg-p-nitroanilide as substrate. Indeed, the rank order of shifts in $T_m$, shown in FIG. 1, paralleled the order of binding affinity as measured by conventional enzymology. These results indicate that by simply observing the shift in $T_m$ for a series of compounds relative to the control, one can easily and correctly rank a series of compounds in increasing order of binding affinity to the protein of interest.

It was possible to take the microplate thermal shift assay one step further and estimate the binding affinity of each ligand at $T_m$. This was done by substituting $T_0$, $T_m$, $\Delta H_u$ and $\Delta C_{pu}$ into equation (1). If $\Delta H_u$ and $\Delta C_{pu}$ cannot be measured because a calorimetric device is not available, one can make educated guesses at $\Delta H_u$ and $\Delta C_{pu}$ for the therapeutic target. In the case of human α-thrombin, it was possible to use $\Delta H_u$=200.0 kcal/mol, a value measured for the closely related protein bovine prothrombin 1 (Lentz, B. R. et al., Biochemistry 33:5460–5468 (1994)). A value of $\Delta C_{pu}$=2.0 kcal/mol-°K was used to calculate $K_L$ at $T_m$ since similar proteins of this size have been shown to yield similar values. The binding affinities at $T_m$ of the five test ligands closely paralleled the $K_i$'s measured with a spectrophotometric substrate (Table 3).

TABLE 3

Microplate Thermal Shift Assay for Ligands Binding to the Active Site of Human α-thrombin. Turbidity as an Experimental Signal.

| Protein/ Ligand | [Ligand] (μM) | $T_m$ (°K) | $\Delta T_m$ (°K) | $K_d$ at $T_m$[a] (nM) | $K_d$ at 310° K[b] (nM) | $K_i$ (310° K)[c] (nM) |
|---|---|---|---|---|---|---|
| Thrombin (TH) | none | 327.15 | 0.0 | | | |
| TH/3dp-3811 | 37 | 328.15 | 1.0 | 14400 | 5880 | 2000 |
| TH/3dp-3959 | 76 | 332.15 | 5.0 | 660 | 224 | 250 |
| TH/3dp-4077 | 48 | 333.15 | 6.0 | 160 | 51.7 | 46 |
| TH/3dp-4076 | 60 | 334.15 | 7.0 | 76.3 | 23.6 | 26 |
| TH/3dp-4026 | 67 | 336.15 | 9.0 | 12.3 | 3.5 | 7.7 |

[a]Calculations for $K_d$ at $T_m$ were made using equation (1) with $\Delta H^{T0}_u$ = 200.0 kcal/mole, as observed for prothrombin 1 by Lentz, B.R. et al., Biochemistry 33:5460–5468 (1994), and an estimated $\Delta C_{pu}$ – 2.0 kcal/mole – °K; and $K_d$ = 1/$K_a$.
[b]Estimates for $K_d$ at T = 310°K were made using equation (3), where $\Delta H^T_L$ was estimated to be –10.0 kcal/mole.
[c]$K_i$ was measured by classical enzymological methods that look at the [inhibitor] dependence of the enzymatic hydrolysis of the spectrophotometric substrate succinyl-Ala-Ala-Pro-Arg-p-nitroanilide at 310°K (50 mM Hepes, pH 7.5, 0.2 M NaCl, 0.05% β-octylglucoside).

EXAMPLE 2

Ranking Ligands That Bind to the Heparin Binding Site of Human α-thrombin

Assays for ligands that bind to the heparin binding site of human α-thrombin are more difficult to perform than assays for ligands that bind to the active site of human α-thrombin. At the heparin binding site, no substrate is hydrolyzed, so no spectrophotometric signal can be amplified for instrumental detection. Heparin activity is usually estimated in biological clotting time assays. Alternatively, heparin binding affinity for human α-thrombin can be determined by laboriously conducting 15 to 20 single point assays, in which the concentration of low MW heparin is varied over two logs, and monitoring the quenching of the fluorescent probe, p-aminobenzamidine, bound to the active site of human α-thrombin (Olson, S. T. et al., *J. Biol. Chem.* 266:6342–6352 (1991)). Thus, heparin binding to human α-thrombin represents the kind of challenge encountered with the vast majority of non-enzyme receptor/ligand binding events, which are commonly observed for hormone/receptor interactions, repressor/DNA interactions, neurotransmitter/receptor interactions, etc. Several heparin-like sulfated oligosaccharides and sulfated naphthalene compounds were assayed by the microplate thermal shift assay. Using the thermal shift assay, it was possible to use a single compound per well to quickly rank the compounds in order of increasing binding affinity, with $K_d$'s ranging over three orders of magnitude (see Table 4). Like the experiment in Example 1, the thermal shift assay results agreed closely with the results obtained through an alternative method, which required a series of laborious (15 to 20 single determinations) fluorescence quench assays over a wide range of concentrations of low MW heparin (Olson, S. T. et al., J. Biol. Chem. 266:6342–6352 (1991)). These results confirm that by simply observing the shift in $T_m$ for a series of compounds, relative to the control, one can easily and correctly rank a series of compounds in increasing order of binding affinity for the protein of interest.

A search of the literature did not locate alternatively measured binding results for the other ligands, which may attest to the difficulty of these experiments. However, the literature did reveal that pentosan polysulfate (PSO$_4$) (Sigma, St. Louis, Mo.), dextran SO$_4$ (Sigma, St. Louis Mo.), and suramin (CalBiochem, LaJolla, Calif.) have been observed to have anticoagulant properties. Indeed, pentosan polysulfate and suramin were tested previously in clinical trials for antiangiogenic activity, but were discounted due to toxic effects, many of which were described as coagulation anomalies (Pluda, J. M. et al., J. Natl. Cancer Inst. 85:1585–1592 (1993), Stein, C. A., Cancer Res. 53:2239–2249 (1993)). The affinities of pentosan PSO$_4$ and suramin at $T_m$, as measured by the thermal shift assay, were found to be 7-fold and 5700-fold higher, respectively, than the affinity of heparin 5000 (Table 4). These results suggested that these ligands may alter clotting rates by interfering with the heparin mediated binding of human α-thrombin to anti-thrombin III (AT III), a protein co-factor for human α-thrombin activity.

The results in Table 4 revealed another advantage of the microplate thermal shift assay for screening compound libraries: the process is blind and unbiased in the sense that it detects ligand binding regardless of whether it is at the active site, an allosteric cofactor binding site, or at a protein subunit interface. The ability to detect ligands that bind with high affinity to sites outside an enzyme's active site will greatly facilitate discovery of lead molecules.

TABLE 4

Microplate Thermal Shift Assay for Ligands Binding to the Heparin
Binding Site of Human α-thrombin. Turbidity as an Experimental Signal.

| Protein/<br>Ligand | [Ligand]<br>(μM) | $T_m$<br>(°K) | $\Delta T_m$<br>(°K) | $K_d$ at $T_m{}^a$<br>(nM) | $K_d$ at<br>298° K$^b$<br>(nM)<br>Observed | $K_i$<br>(298° K)<br>(nM)<br>Litera-<br>ture |
|---|---|---|---|---|---|---|
| Thrombin (TH) | none | 329.15 | 0.0 | | | |
| TH/Heparan SO$_4$ | 61 | 329.65 | 0.5 | 38,300 | 7,570 | — |
| TH/Heparin 3000 | 50 | 330.15 | 1.0 | 19,700 | 3,810 | — |
| TH/Heparin 5000 | 44 | 330.15 | 1.0 | 17,200 | 3,490 | 5,400$^c$ |
| TH/Pentosan PSO$_4$ | 40 | 332.15 | 3.0 | 2,425 | 427 | — |
| TH/Dextran SO$_4$ | 48 | 336.15 | 7.0 | 68.8 | 10.1 | — |
| TH/Suramin | 102 | 340.15 | 11.0 | 3.02 | 0.37 | — |

$^a$Calculations for $K_d$ at $T_m$ were made using equation (1) with $\Delta H^{T°}{}_u = 200.0$ kcal/mole, as observed for pre-thrombin 1 by Lentz, B.R. et al., Biochemistry 33:5460–5468 (1994), and an estimated $\Delta C_{pu} = 2.0$ kcal/mole-°K; and $K_d = 1/K_a$. The thrombin, human α-thrombin (Factor IIa), from Enzyme Research Labs (South Bend, IN) was diluted to 0.5 mg/mL (11 μM) using 50 mM Hepes, pH 7.5, 0.1 M NaCl (3-fold dilution). All ligands were dissolved in the same buffer.
$^b$Estimates for $K_d$ at T = 298° K were made using equation (3), where $\Delta H^T{}_L$ is estimated to be –10.0 kcal/mole.
$^c$Olson, S.T. et al., J. Biol. Chem. 266:6342–6352 (1991).

EXAMPLE 3

Ranking aFGF Ligands

Figure 2:
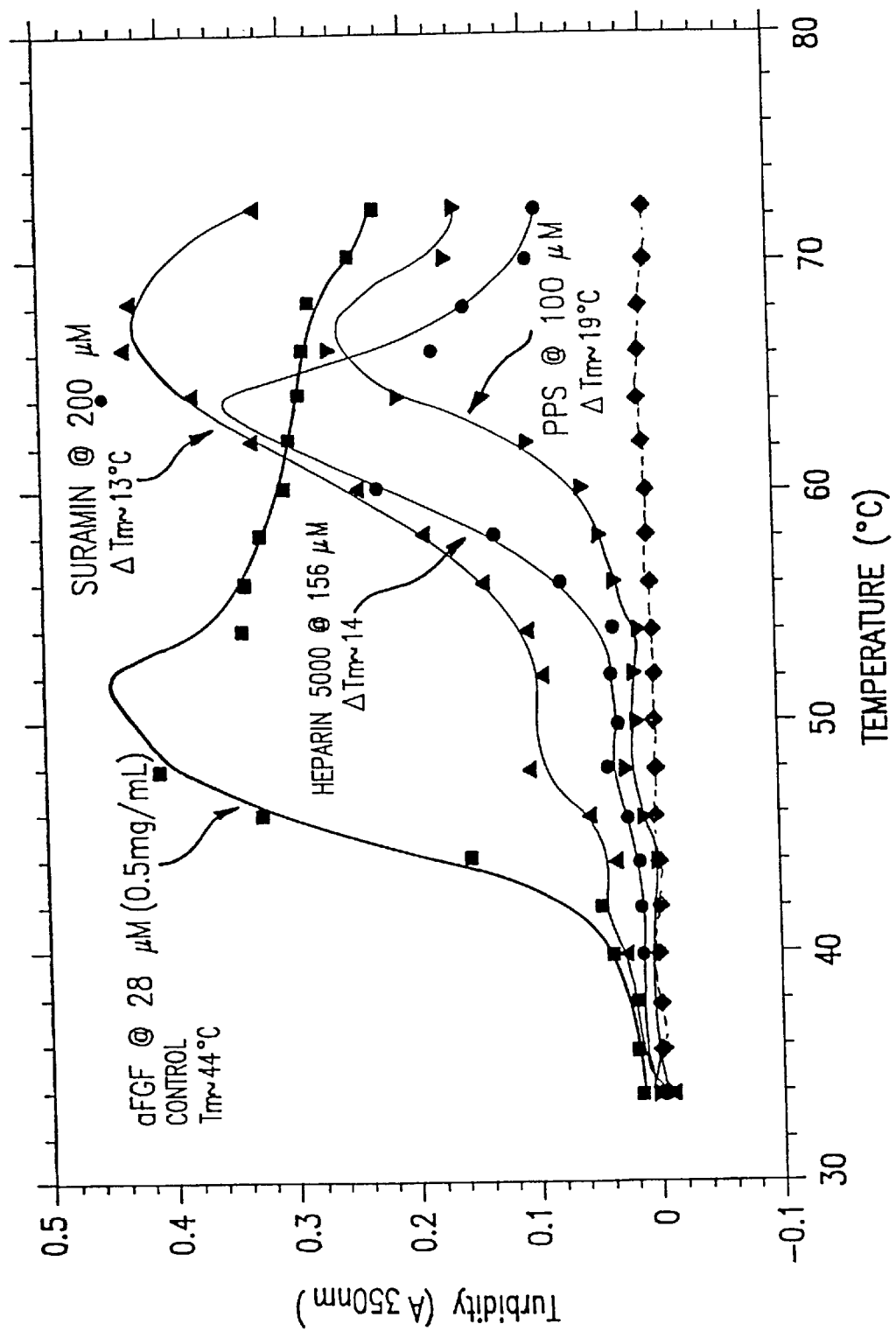
FIG. 2 shows the results of a microplate thermal shift assay for ligands which bind to acidic fibroblast growth factor (aFGF) (with turbidity as the experimental signal).

The second therapeutic receptor tested in the microplate thermal shift assay was acidic fibroblast growth factor (aFGF), a growth factor that plays a key role in angiogenesis (Folkman, J. et al., J. Biol. Chem. 267:1.0931–10934 (1992)). A synthetic gene for this protein was purchased from R&D Systems (Minneapolis, Minn.), and was cloned and expressed in E. coli using methods similar to those described for basic fibroblast growth factor (bFGF) (Thompson, L. D. et al., Biochemistry 33:3831–3840 (1994); Pantoliano, M. W. et al., Biochemistry 33:10229–10248 (1994); Springer, B. A. et al., J. Biol. Chem. 269:26879–26884 (1994)). Recombinant aFGF was then purified by heparin-sepharose affinity chromatography as described (Thompson, L. D. et al., Biochemistry 33:3831–3840 (1994)). aFGF is also known to bind heparin/heparan, which is a cofactor for mitogenic activity. Heparin-like molecules, such as pentosan PSO$_4$ and suramin, inhibit the growth factor's biological activity. A microplate thermal assay of these compounds was set up in a way similar to that described above for human α-thrombin. The change in turbidity, as a function of temperature, for each of the ligands suramin, heparin 5000, and pentosan PSO$_4$, is shown in FIG. 2. The results are summarized in Table 5. The affinity constants covered a fairly broad range of binding affinities, with pentosan PSO$_4$ showing the highest affinity. The order of ligand binding affinity of pentosan PSO$_4$, heparin 5000 and suramin paralleled that found for bFGF, as measured using isothermal titrating calorimetry (Pantoliano, M. W. et al., Biochemistry 33:10229–10248 (1994)). The lack of alternatively measured binding affinities for these compounds probably attests to the difficulty of making these measurements using assays which do not monitor physical, temperature-dependent changes.

The results in Table 5 are consistent with the results in Tables 3 and 4. Simply observing the shift in $T_m$ for a series of compounds relative to the control, one can easily and correctly rank a series of compounds in increasing order of binding affinity to the protein of interest.

TABLE 5

Microplate Thermal Shift Assay for Ligands Binding to aFGF. Turbidity as an Experimental Signal.

| Protein/<br>Ligand | [Ligand]<br>(μM) | $T_m$<br>(°K) | $\Delta T_m$<br>(°K) | $K_d$ at $T_m{}^a$<br>(nM) | $K_d$ at<br>298° K$^b$<br>(nM)<br>Observed | $K_i$<br>(298° K)$^c$<br>(nM)<br>Litera-<br>ture |
|---|---|---|---|---|---|---|
| aFGF | none | 317.15 | 0.0 | | | |
| aFGF/EEEE | 50 | 317.15 | 0.0 | >50,000 | | — |
| aFGF/Dermatan SO$_4$ | 50 | 318.15 | 1.0 | 37,000 | 12,700 | — |
| aFGF/EEEEEEEE | 50 | 322.15 | 5.0 | 10,076 | 3,040 | — |
| aFGF/β-CD 14 SO$_4$ | 47 | 329.15 | 12.0 | 1055 | 213 | 1500 |
| aFGF/suramin | 200 | 330.15 | 13.0 | 3220 | 622 | |
| aFGF/Heparin 5000 | 50 | 331.15 | 14.0 | 576 | 106 | 470 |

TABLE 5-continued

Microplate Thermal Shift Assay for Ligands Binding to aFGF. Turbidity as an Experimental Signal.

| Protein/ Ligand | [Ligand] ($\mu$M) | $T_m$ (°K) | $\Delta T_m$ (°K) | $K_d$ at $T_m{}^a$ (nM) | $K_d$ at 298° K$^b$ (nM) Observed | $K_i$ (298° K)$^c$ (nM) Literature |
|---|---|---|---|---|---|---|
| aFGF/Heparan SO$_4$ | 61 | 333.15 | 16.0 | 357 | 60 | — |
| aFGF/Pentosan PSO$_4$ | 100 | 336.15 | 19.0 | 208 | 31 | 88 |

$^a$Calculations for $K_d$ at $T_m$ were made using equation (1) with an estimated $\Delta H^{T0}{}_u$ = 60.0 kcal/mole, and an estimated $\Delta C_{pu}$ = 0.95 kcal/mole-°K; and $K_d$ = 1/$K_a$. All ligands, except β-CD 14 SO$_4$, were purchased from Sigma and used without further purification. β-CD 14 SO$_4$ was purchased from American Maize Products Co. (Hammond, IN). The aFGF was diluted to 0.25 mg/mL in 50 mM Hepes, pH 7.5, 0.1 M NaCl. All ligands were dissolved in the same buffer.
$^b$Estimates for $K_d$ at T = 298° K were made using equation (3), where $\Delta H_L{}^T$ is estimated to be −10.0 kcal/mole.
$^c$No published binding affinity data for these ligands was found in the literature, but the affinities for these ligands binding to bFGF, as measured by isothermal titrating calorimetry, are shown (Thompson, L.D. et al., Biochemistry 33:3831–3840 (1994); Pantoliano, M.W. et al., Biochemistry 33: 10229–10248 (1994)).

EXAMPLE 4

Ranking bFGF Ligands

The microplate thermal shift assay was used to assess ligands for binding to the heparin binding site of basic fibroblast growth factor (bFGF). The gene for bFGF was purchased from R&D Systems and was cloned and expressed in *E. coli* as previously described (Thompson, L. D. et al., Biochemistry 33:3831–3840 (1994); Pantoliano, M. W. et al., Biochemistry 33:10229–10248 (1994); Springer, B. A. et al., J. Biol. Chem. 269:26879–26884 (1994)). It was found that pentosan PSO$_4$ and suramin bound to bFGF with binding affinities of 55 nM and 3.5 $\mu$M, respectively. This result for PSO$_4$ compared very well with the affinity of 88 nM observed for PSO$_4$ binding to bFGF, as determined by isothermal titrating calorimetry.

EXAMPLE 5

Ranking Human α-thrombin Ligands Using Fluorescence Emission

Because fluorescence measurements are more sensitive than absorbance measurements, a fluorescence thermal shift assay was used to assess ligand binding to human α-thrombin. The fluorescence emission spectra of many fluorophores are sensitive to the polarity of their surrounding environment and therefore are effective probes of phase transitions for proteins (i.e., from the native to the unfolded phase). The most studied example of these environment dependent fluorophores is 8-anilinonaphthalene-1-sulfonate (1,8-ANS), for which it has been observed that the emission spectrum shifts to shorter wavelengths (blue shifts) as the solvent polarity decreases. These blue shifts are usually accompanied by an increase in the fluorescence quantum yield of the fluorophore. In the case of ANS, the quantum yield is 0.002 in water and increases to 0.4 when ANS is bound to serum albumin.

ANS was used as a fluorescence probe molecule to monitor protein denaturation. In the fluorescence assay, the final concentration of human α-thrombin was 0.5 $\mu$M, which is 20-fold more dilute than the concentrations used in the turbidity assays. This concentration of human α-thrombin is in the range used for the kinetic screening assays.

Figure 3:
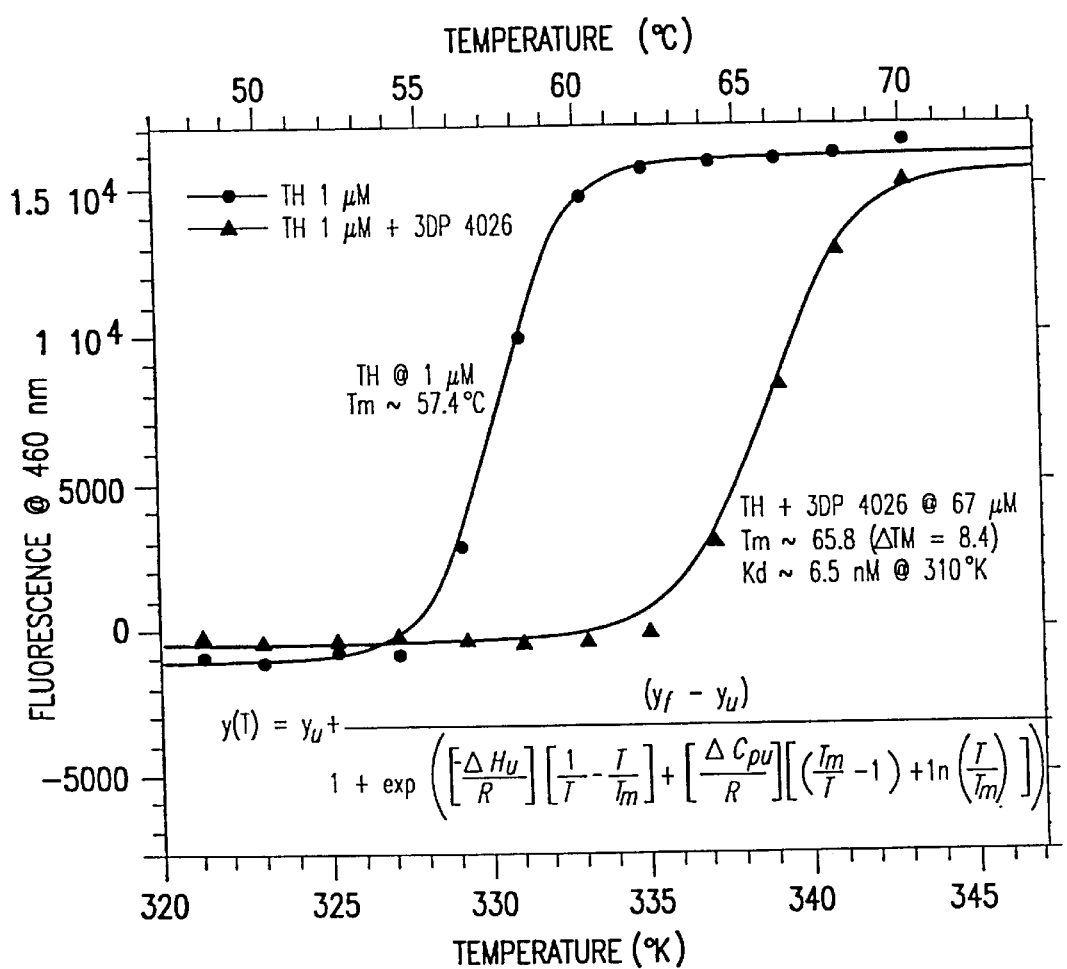
FIG. 3 shows the results of a microplate thermal shift assay for ligand binding to the active site of human α-thrombin (with fluorescence emission as the experimental signal). The lines drawn through the data points represent non-linear least squares curve fits of the data using the equation shown at the bottom of the figure. There are five fitting parameters for this equation of y(T) vs. T: (1) $y_f$, the pre-transitional fluorescence for the native protein; (2) $y_u$, the post-transitional fluorescence for the unfolded protein; (3) $T_m$, the temperature at the midpoint for the unfolding transition; (4) $\Delta H_u$, the van't Hoff unfolding enthalpy change; and (5) $\Delta C_{pu}$, the change in heat capacity upon protein unfolding. The non-linear least squares curve fitting was accomplished using KALEIDAGRAP™ 3.0 software (Synergy Software, Reading Pa.), which allows the five fitting parameters to float while utilizing Marquardt methods for the minimization of the sum of the squared residuals.

ANS was excited with light at a wavelength of 360 nm. The fluorescence emission was measured at 460 nm using a CytoFluor II fluorescence microplate reader (PerSeptive Biosystems, Framingham, Mass.). The temperature was ramped up as described above for the turbidity assays (see Example 1). The plot of fluorescence as a function of temperature is shown in FIG. 3 for human α-thrombin alone, and for the 3dp-4026/human α-thrombin complex. The denaturation transition for human α-thrombin was clearly observed at 57° C., a temperature which is only slightly higher than that observed in the turbidity experiment. The result from the fluorescence assay is, nonetheless, in close agreement with the $T_m$ of 58° C. observed for prothrombin 1 from differential scanning calorimetry experiments. Importantly, 3dp-4026 (at 67 $\mu$M) was found to shift the denaturation transition to ~66° C. to give a shift in $T_m$ of 9° C., which is identical to that found using turbidity as the detection signal (Table 3).

The results in FIG. 3 and Table 4 illustrate several important points. First, at least a 20-fold increase in sensitivity can be gained by switching from an absorbance to a fluorescence emission detection system. This can be critical for those receptor proteins for which supplies are limited.

Second, in the fluorescence assays, the denaturation transition signal is much cleaner than the signal in the turbidity assays. In the turbidity assays, higher concentrations of protein led to precipitation of denatured protein. Precipitated protein contributed to the noisy signal.

Third, shifts in $T_m$ measurements from the microplate thermal shift assays are reproducible from one detection system to another.

EXAMPLE 6

Ranking Ligands to the D(II) Domain of FGFR1

The microplate thermal-shift assay was employed to test the binding of heparin 5000 and pentosan PSO$_4$ to the known heparin binding site in the D(II) domain of fibroblast growth factor receptor 1 (FGFR1). D(II) FGFR1 is a 124 residue domain which is responsible for most of the free energy of binding for bFGF. D(II) FGFR1 was cloned and expressed in *E. coli*. Recombinant D(II) FGFR1 was renatured from inclusion bodies essentially as described (Wetmore, D. R. et al., Proc. Soc. Mtg., San Diego, Calif. (1994)), except that a hexa-histidine tag was included at the N-terminus to facilitate recovery by affinity chromatography on a $Ni^{2+}$ chelate column (Janknecht, R. et al., Natl. Acad. Sci. USA 88:8972–8976 (1991)). D(II) FGFR1 was further purified on a heparin-sepharose column (Kan, M. et al., Science 259:1918–1921 (1993); Pantoliano, M. W. et al., Biochemistry 33:10229–10248 (1994)). Purity was >95%, as judged by SDS-PAGE. The D(II) FGFR1 protein was concentrated to 12 mg/mL (~1 mM) and stored at 4° C.

The D(II) FGFR1 protein was dissolved in an ANS solution to a concentration of 1.0 mg/mL (70 µM). The quantum yield for ANS bound to the denatured form of D(II) FGFR1 was lower than the quantum yield for ANS bound to human α-thrombin. Because ANS fluorescence is very environment dependent (see Lakowicz, I. R., Principles of Fluorescence Spectroscopy, Plenum Press, New York (1983)), the quantum yield observed for the denaturation of different proteins will vary. For D(II) FGFR1, the signal for the turbidity version of the assay, however, was nearly undetectable. Despite the decreased sensitivity for D(II) FGFR1, ANS rescued this system for the microplate assay. A similar result was obtained for Factor Xa, except that the fluorescence quantum yield for ANS bound to denatured Factor Xa was almost as good as it was for human α-thrombin. It was found that the fluorescence quantum yield for ANS bound to denatured bFGF was as high as the quantum yield for ANS binding to human α-thrombin.

Figure 4:
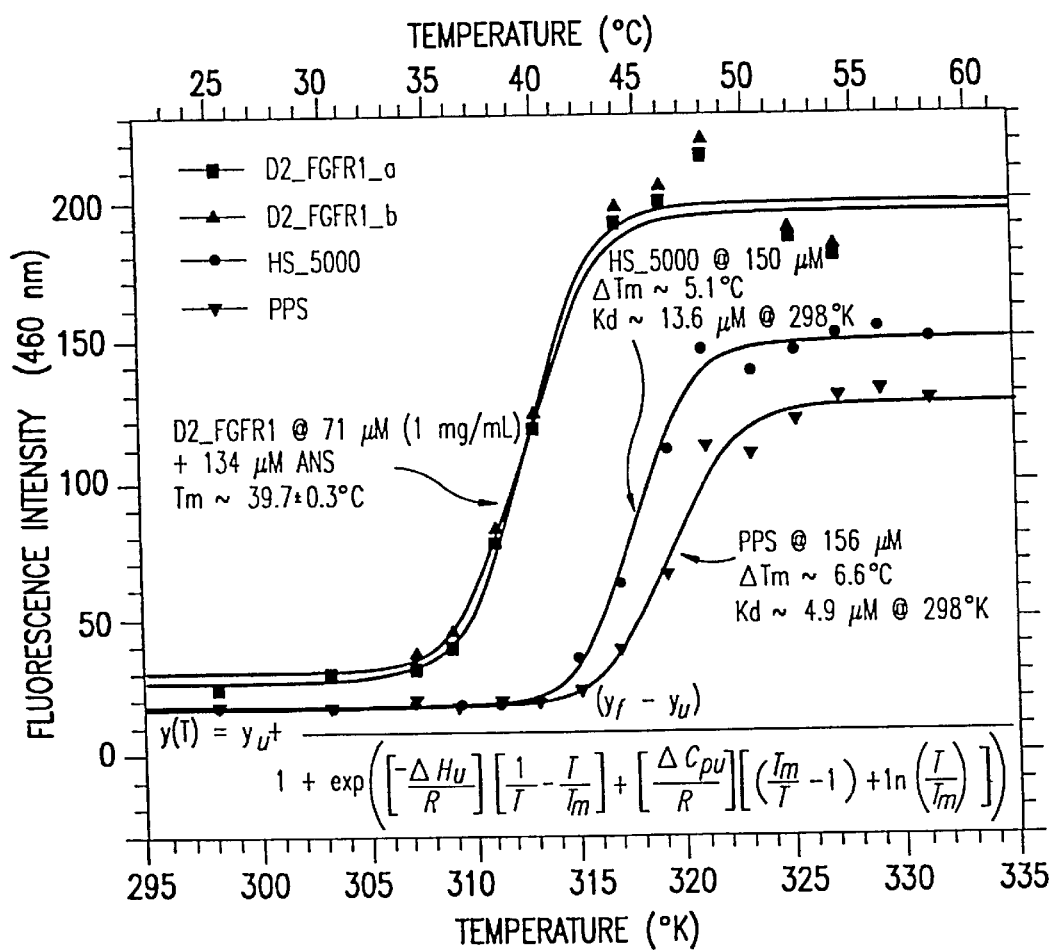
FIG. 4 shows the result of a microplate thermal shift assay of ligands which bind to the D(II) domain of human FGF receptor 1 (D(II) FGFR1) (with fluorescence emission as the experimental signal). The lines drawn through the data points represent non-linear least squares curve fits of the data using the equation shown at the bottom of the figure, as described for FIG. 3.

The results of D(II) FGFR1 binding experiments, as determined by the microplate thermal shift assay, are shown in FIG. 4 and Table 6. As was previously demonstrated for all of the other receptor proteins described above, the microplate thermal shift assay facilitated the ranking of ligand binding affinities for D(II) FGFR1.

TABLE 6

Microplate Thermal Shift Assay for Ligands Binding to D(II) FGFR1. Fluorescence Emission as an Experimental Signal.

| Protein/Ligand | [Ligand] (µM) | $T_m$ (°K) | $\Delta T_m$ (°K) | $K_d$ at $T_m^a$ (µM) | $K_d$ at 298° $K^b$ (µM) Observed | $K_d$ (298° K)$^c$ (µM) Literature |
|---|---|---|---|---|---|---|
| D(II)FGFR1 | none | 312.8 | 0.0 | | | |
| D(II)FGFR1/ Heparin 5000 | 150 | 317.9 | 5.1 | 30.0 | 13.6 | 85.3 |
| D(II)FGFR1/ Pentosan $PSO_4$ | 156 | 319.4 | 6.6 | 19.1 | 4.9 | 10.9 |

$^a$Calculations for $K_d$ at $T_m$ were made using equation (1) with an estimated $\Delta H_u^{T0}$ = 60.0 kcal/mole, and an estimated $\Delta C_{pu}$ = 0.95 kcal/mole-°K; and $K_d = 1/K_a$. The D(II) FGFR1 was diluted to 1.0 mg/mL (70 µM) in 50 mM Hepes, pH 7.5, 0.1 M NaCl with 136 µM ANS present. All ligands were dissolved in the same buffer and diluted 50-fold into the protein solution.
$^b$Estimates for $K_d$ at T = 298° K were made using equation (3), where $\Delta H_L^T$ = -12.1, and -7.48 kcal/mole for the pentosan $PSO_4$ and heparin 5000, respectively, as determined by isothermal titrating calorimetry (Pantoliano, M.W. et al., Biochemistry 33:10229–10248 (1994)).
$^c$Published binding affinity data for these ligands binding to D(II)–D(III) FGFR1 as determined by titrating calorimetry (Pantoliano, M.W. et al., Biochemistry 33: 10229–10248 (1994)).

EXAMPLE 7

Microplate Thermal Shift Assay of Factor D

Figure 5:
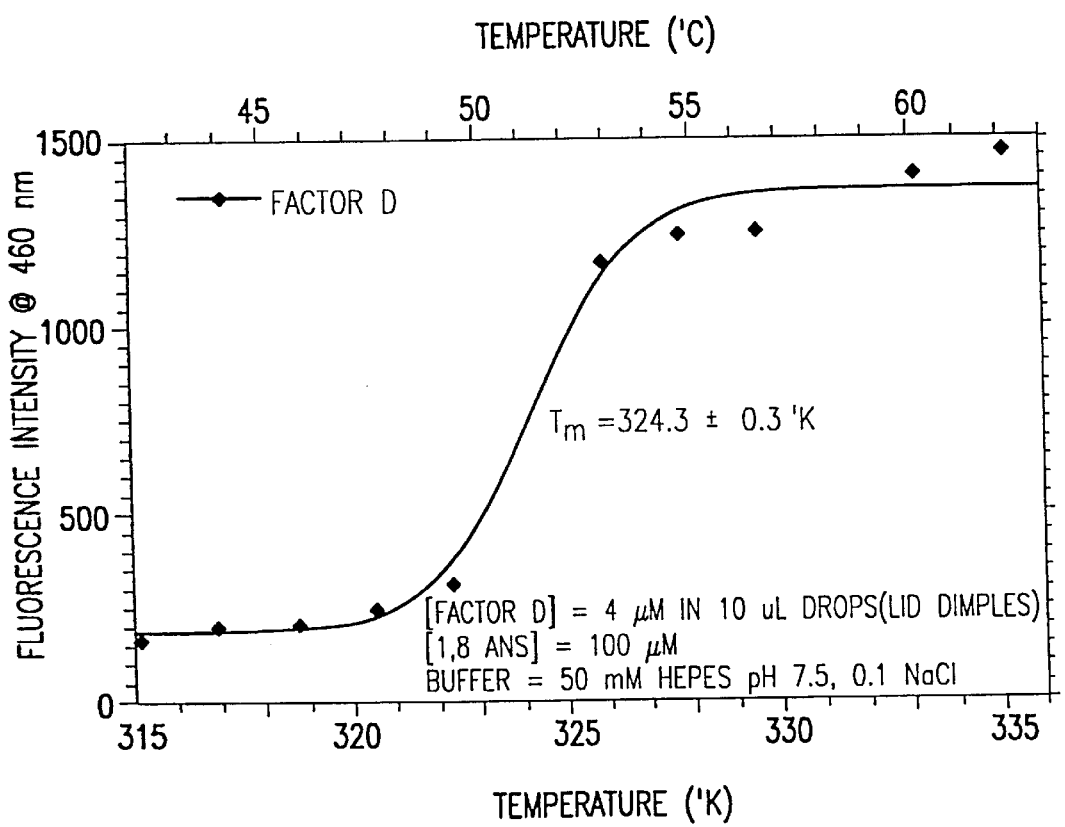
FIG. 5 shows the results of a miniaturized microplate thermal shift assay for Factor D in the absence of any ligands.

In order to further demonstrate the cross target utility of the microplate thermal shift assay, another enzyme, Factor D, was tested for its ability to undergo thermal unfolding transitions. Factor D is an essential serine protease involved in the activation of the alternative pathway of the complement system, the major effector system of the host defense against invading pathogens. Factor D was purified from the urine of a patient with Fanconi's syndrome (Narayana et al., J. Mol. Biol. 235:695–708 (1994)) and diluted to 4 µM in assay buffer (50 mM Hepes, pH 7.5, 0.1 M NaCl). The assay volume was 10 µL and the concentration of 1,8-ANS was 100 µM. The experiment was carried out using 15 µL round bottom dimple plates (an 8×12 well array). The protein was heated in two degree increments between 42° C. to 62° C., using a Robocyclerm temperature cycler. After each heating step, and prior to fluorescence scanning using the CytoFluor II™ fluorescence plate reader the sample was cooled to 25° C. (see Example 1). The non-linear least squares curve fitting and other data analysis were performed as described for FIG. 3. The results of the microplate thermal shift assay of Factor D is shown in FIG. 5 and reveal a thermal unfolding transition that occurs near 324 K (51° C.) for the unliganded form of the protein. No reversible ligands of significant affinity are known for Factor D. The results in FIG. 5 show that the microplate thermal shift assay can be used to screen a library of compounds for Factor D ligands. The results in FIG. 5 also show that the microplate thermal shift assay is generally applicable to any target molecule.

EXAMPLE 8

Microplate Thermal Shift Assay of Factor Xa

Figure 6:
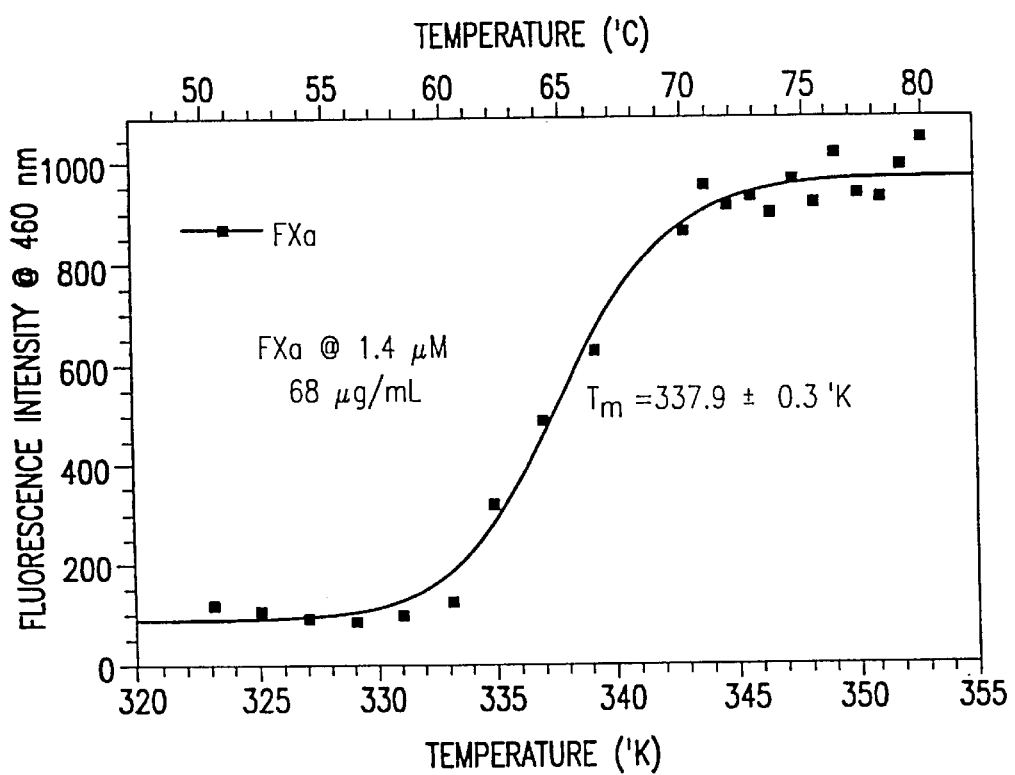
FIG. 6 shows the results of a microplate thermal shift assay for Factor Xa in the absence of any ligands.

Human Factor Xa, a key enzyme in the blood clotting coagulation pathway, was chosen as yet another test of the cross target utility of the microplate thermal shift assay. Factor Xa was purchased from Enzyme research Labs (South Bend, Ind.) and diluted to 1.4 µM in assay buffer (50 mM Hepes, pH 7.5, 0.1 M NaCl). The assay volume was 100 µL and the concentration of 1,8-ANS was 100 µM. The protein was heated in two degree increments between 50° C. to 80° C. using a Robocycler™ temperature cycler. After each heating step, prior to fluorescence scanning using the CytoFluor II™ fluorescence plate reader, the sample was cooled to 25° C. (see Example 1). The results of a microplate thermal shift assay of Factor Xa is shown in FIG. 6. A thermal unfolding transition was observed at 338K (65° C.). Data analysis was described as described for FIG. 3. The results in FIG. 6 show that the microplate thermal shift assay of protein stability is generally applicable to any target molecule.

EXAMPLE 9

Figure 7:
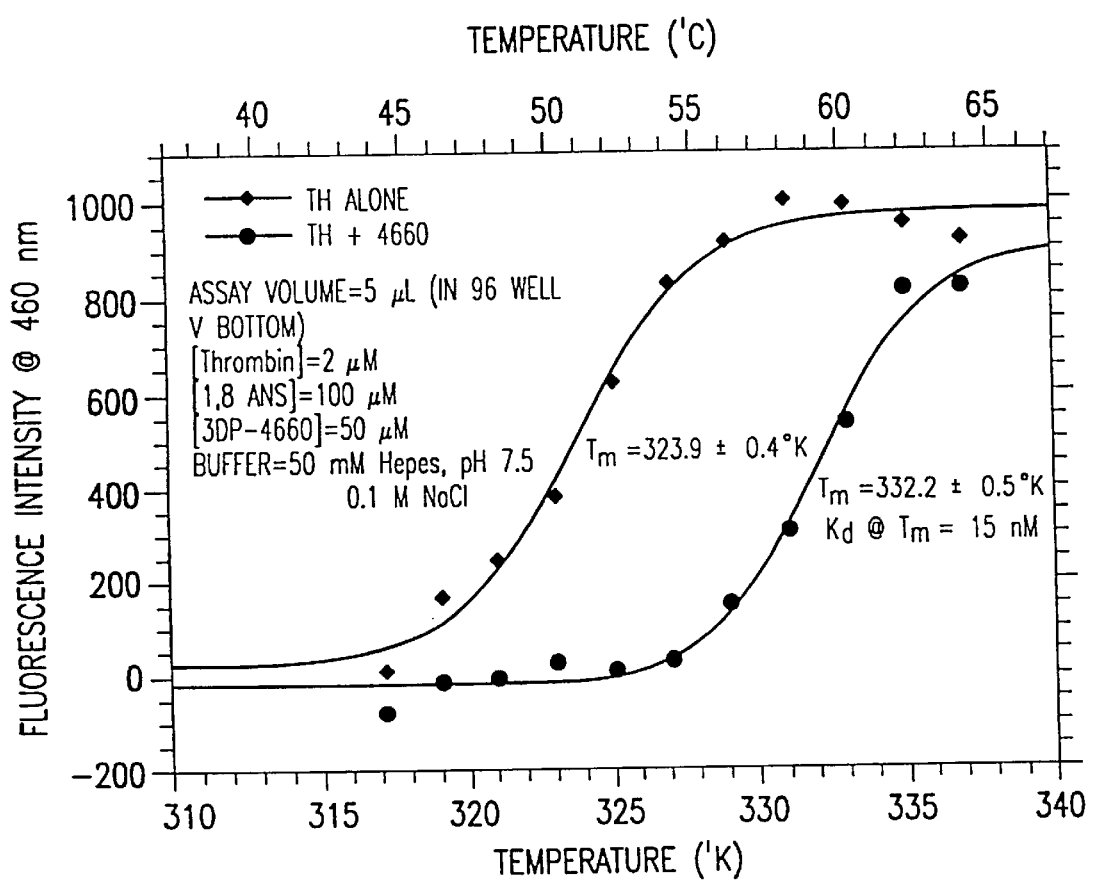
FIG. 7 shows the results of a miniaturized microplate thermal shift assay of a ligand that binds to the catalytic site of human α-thrombin.

Miniaturization of the Microplate Thermal Shift Assay of Ligands Binding to Human α-Thrombin A miniaturized form of the microplate thermal shift assay was developed to minimize the amount of valuable therapeutic protein and ligands required for the assay. In the first attempt at decreasing the assay volume, the assay volume was decreased from 100 µL to 50 µL without adversely affecting the fluorescent signal. When the assay volume was reduced further by a factor of ten, to 5 µL, favorable results were obtained for human α-thrombin. As shown in FIG. 7, the human α-thrombin unfolding transition could be easily observed at its usual $T_m$. More importantly, an active site inhibitor was observed to shift the $T_m$ of the unfolding transition by 8.3°K to yield an estimate of the $K_d$ of 15 nM at the $T_m$. The $K_a$ at $T_m$ was calculated using the relationship:

$$K_L^{T_m} = \frac{\exp\left\{-\frac{\Delta H_u^{T_0}}{R}\left[\frac{1}{T_m} - \frac{1}{T_0}\right] + \frac{\Delta C_{pu}}{R}\left[\ln\left(\frac{T_m}{T_0}\right) + \frac{T_0}{T_m} - 1\right]\right\}}{[L_{T_m}]} \quad \text{(equation 1)}$$

where $K_L^{T_m} = K_a$ at $T_m$ (ligand associate constant at $T_m$)

$T_m = 332.2°K$ (midpoint of the unfolding transition in the absence of a ligand)

$T_0 = 323.9°K$ $H_u = 200.0$ kcal/mol (enthalpy of unfolding for pre thrombin observed by Lentz et al., 1994)

$C = 2.0$ kcal/mol (estimated change in heat capacity of unfolding for human α-thrombin)

$_T = 50.0$ μM

The Kd at temperatures near 25 or 37° C. will be of higher affinity if the enthalpy of binding, $\Delta H_b$, is negative for this ligand. Using a spectrophotometric assay, an apparent $K_i$ of approximately 8 rM was observed at 37° C. (310°K).

The measurements shown. in FIG. 7 were obtained using the CytoFluor II fluorescence plate reader (PerSeptive Biosystems, Framingham, Mass.). In the experiment, the excitation wavelength of light was 360 nm and the emission was measured at 460 nm. The microplates employed for this miniaturized assay were either the conventional polycarbonate V-bottom 96 well plate (Stratagene, or Costar) or polycarbonate plates that contain 15 μL dimples in an 8×12 array (Costar plate lids). In the reaction, the concentration of human α-thrombin was μM in assay buffer (50 mM Hepes, pH 7.5, 0.1 M NaCl). The assay volume was 5 μL and the concentration of 1,8-ANS was 100 μM. The protein was heated in two degree increments between 44° C. to 64° C. using a Robocycler™ temperature cycler. After each heating step, and prior to fluorescence scanning using the CytoFluor II™ fluorescence plate reader the sample was cooled to 25° C. for 30 seconds (see Example 1). The non-linear least squares curve fitting and other data analysis were performed as described for FIG. 3.

EXAMPLE 10

Miniaturization of the Microplate Thermal Shift Assay of Ligands Binding to D(II) FGFR1

Figure 8A:
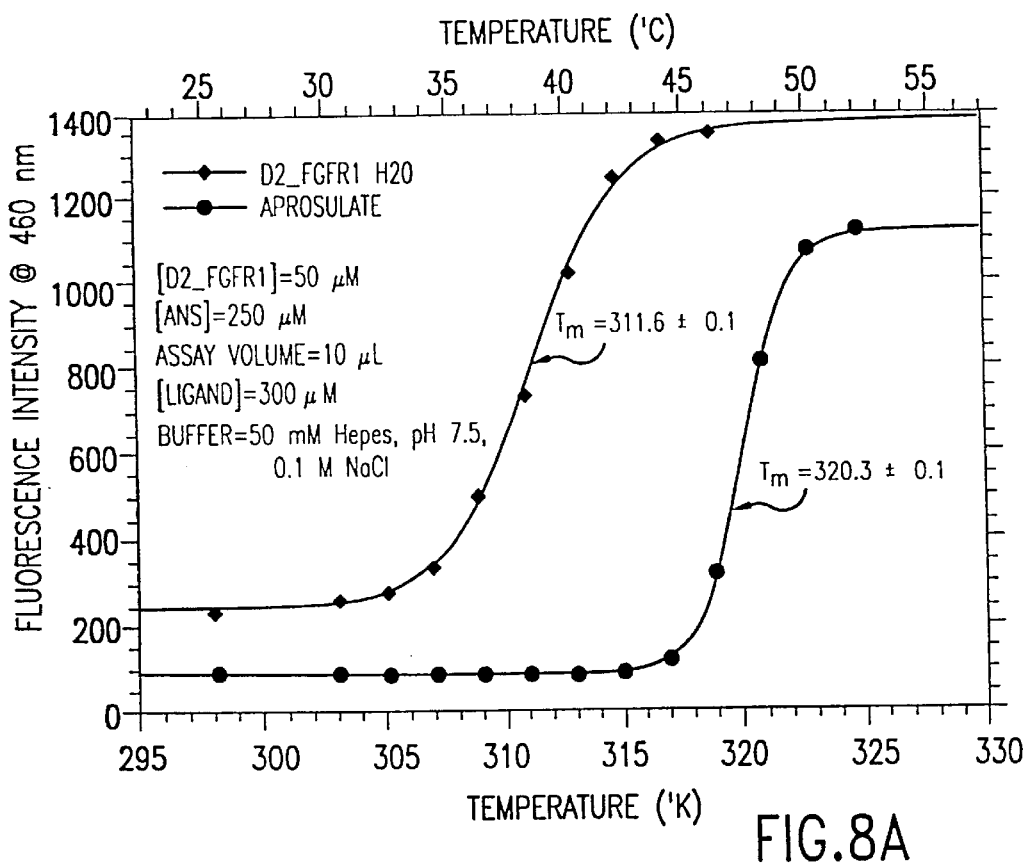
FIGS. 8A and 8B show the results of a miniaturized microplate thermal shift assay of aprosulate binding to the D(II) domain of human FGF receptor 1.
Figure 8B:
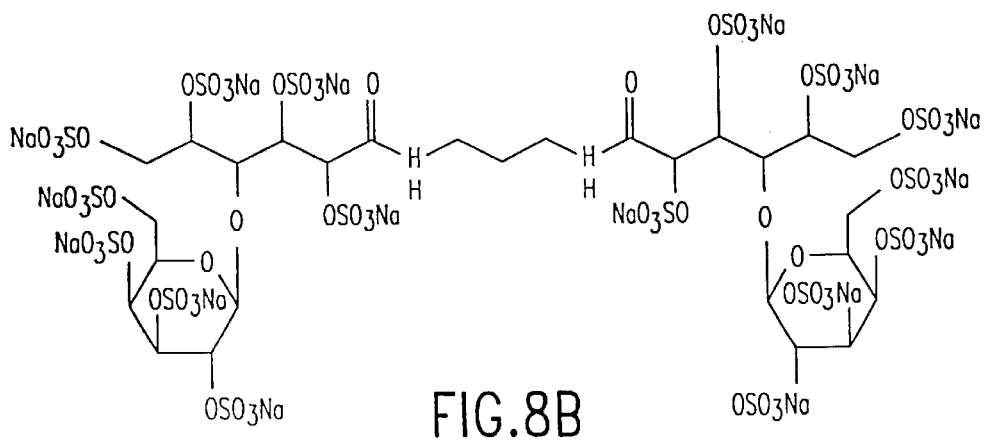
Figure 9:
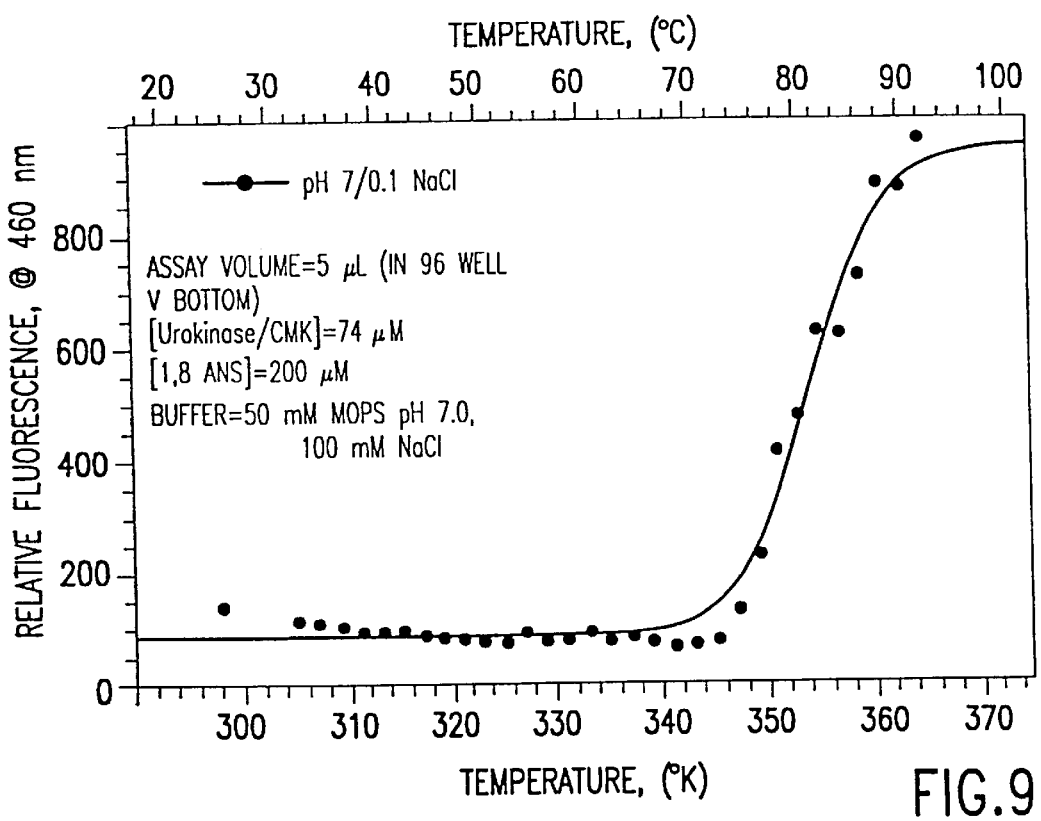
FIG. 9 shows the results of a miniaturized microplate thermal shift assay for urokinase in the presence of glu-gly-arg chloromethylketone.

Recombinant D(II) FGFR1 was purified from inclusion bodies and purified by affinity chromatography on heparin sepharose. A stock solution of D(II) FGFR1 (15 mg/mL; 1.1 mM) was diluted to 50 μM in assay buffer (50 mM Hepes, pH 7.5, 0.1 M NaCl). The assay volume was 10 μL and the concentration of 1,8-ANS was 250 μM. The unfolding transition in the absence of ligands was found to be about 312 K (39° C.) as shown in FIG. 8. In the presence of the heparin mimic aprosulate (300 μM), the unfoding transition was observed to increase by about 8 K to about 320 K. Using this temperature midpoint $T_m$, it is possible to estimate the binding affinity of aprosulate to D(II)FGFR1 to be about 18 μM at the $T_m$ (Table 6). These results demonstrate the ability of the microplate thermal shift assay to estimate ligand binding affinity to a non-enzyme target molecule.

EXAMPLE 11

Miniaturization of the Microplate Thermal Shift Assay of Urokinase

Another target molecule analyzed was human urokinase-type plasminogen activator (u-PA). U-PA enzymatically converts plasminogen into the active protease plasmin. U-PA is involved in tissue remodeling, cellular migration and metastases. The gene for u-PA was obtained from ATCC (Rockville, Md.) and modified to appropriately express active enzyme in E. coli. u-PA was cloned, overexpressed in E. coli, and purified using procedures similar to those described by Winkler et al. (Biochemistry 25:4041–4045 (1986)). The last step of u-PA purification was performed in the presence of the active site inhibitor glu-gly-arg-chloromethylketone (CMK) and hence the u-PA utilized for this experiment was the CMK-u-PA complex. The experiment was performed in the miniaturized format in 5 μL well volume. One μL of concentrated CMK-u-PA (13 g/L, 371.4 μM) was added to 4 μL of 62.5 mM MOPS, pH 7, 125 mM NaCl, and 250 μM 1,8-ANS, in multiple wells of a 96-well polycarbonate V-bottom microtiter plate. A thermal denaturation curve was generated as previously described for thrombin, aFGF, D(II)FGFR1, Factor D, and Factor Xa, by incremental heating of the microplate followed by a fluorescence reading after each temperature increase. Analysis and non-linear least squares fitting of the data for this experiment show that the $T_m$ for CMK-u-PA under these conditions is 81° C., which is considerably higher than that seen for thrombin, aFGF, D(II)FGFR1, Factor D, and Factor Xa (55, 44, 40, 51, 55, and 65° C., respectively). This experiment demonstrates the utility of the current invention in determining the $T_m$ for relatively thermostable proteins or proteins stabilized by the high affinity binding of ligand(s) and further demonstrates the ability to perform such an experiment in a miniaturized format.

EXAMPLE 12

Figure 10:
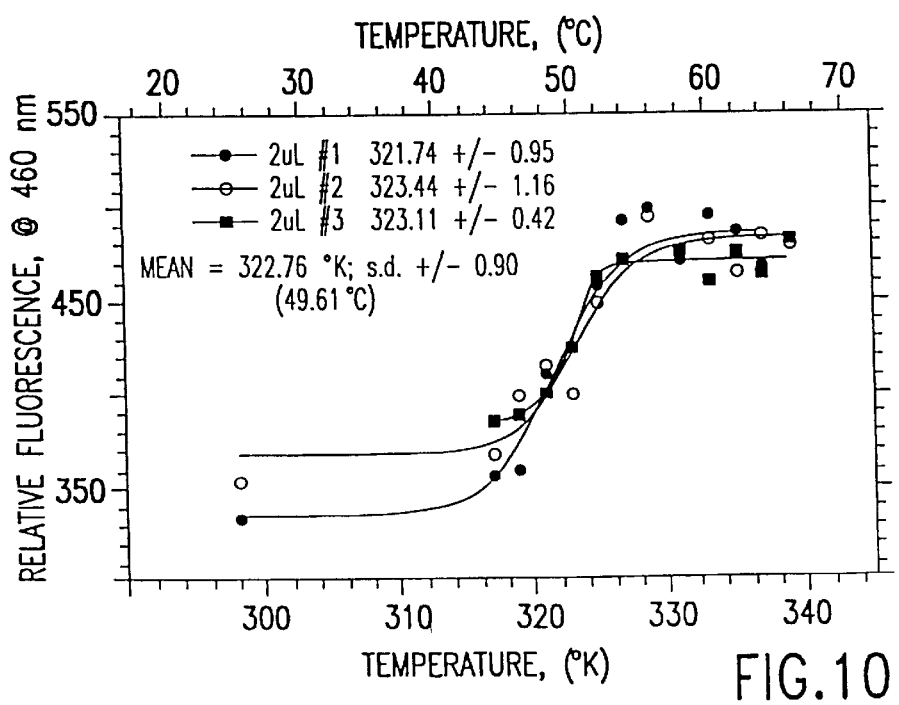
FIG. 10 shows the results of a miniaturized microplate thermal shift assay of human α-thrombin in which the assay volume is 2 μl. Thermal denaturation curves for three experiments are shown.
Figure 11:
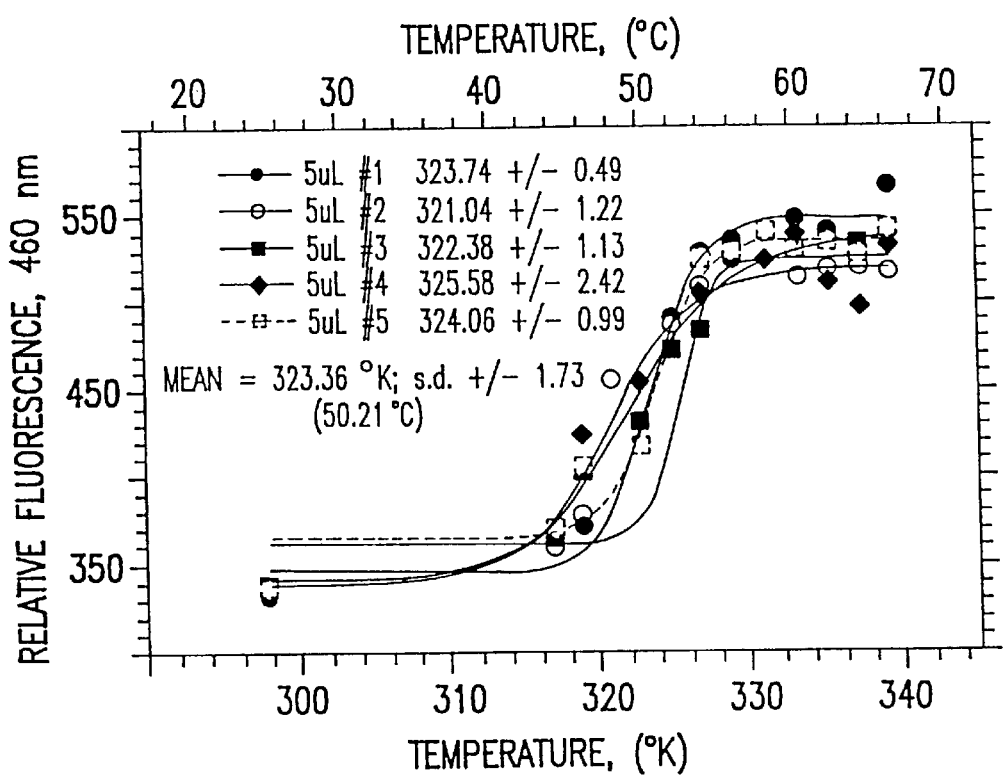
FIG. 11 shows the results of a miniaturized microplate thermal shift assay of human α-thrombin in which the assay volume is 5 μl. Thermal denaturation curves for five experiments are shown.

Further Miniaturization of the Microplate Thermal Shift Assay of Human α-thrombin A stock thrombin solution was diluted to 1 μM in 50 mM Hepes, pH 7.5, 0.1 M NaCl and 100 μM 1,8-ANS. An electronic multi-channel pipettor was used to dispense either 2 μL or 5 μL of diluted thrombin solution into wells of a 96-well polycarbonate microtiter plat. The plate was subjected to 3 minutes of heating in a thermal block capable of establishing a temperature gradient across the microplate, followed by 30 seconds cooling to 25° C., and subsequent reading in the CytoFluor II fluorescence plate reader. Data were analyzed by non-linear least squares fitting and plotted as shown in FIGS. 10 and 11. Each curve represents a replicate experiment. Standard deviations for $T_m$ determinations were very good for experiments utilizing either 5 μL or 2 μL volumes (+/−1.73 and +/−0.90 K, respectively), demonstrating the ability of the current invention to operate at very low volumes. In fact, the volume which one could employ in the current invention seems to be limited only by the technology available to dispense small volumes accurately.

The assay volume was reduced to 2 μL, as shown for human α-thrombin (1.0 μM) in FIG. 11. Reproducible pipetting of 2 μL in a 96 well array requires the employment of specialized pipetting tools such as the multi-channel pipettor available from Matrix Technologies Corp. (Lowell, Mass.) which has ±2.0% or 0.15 μL precision and ±2.5% or 0.15 μL accuracy for volumes 0.5 to 12.5 μL.

EXAMPLE 13

Single Temperature Mode of the Microplate Thermal Shift Assay

Figure 12:
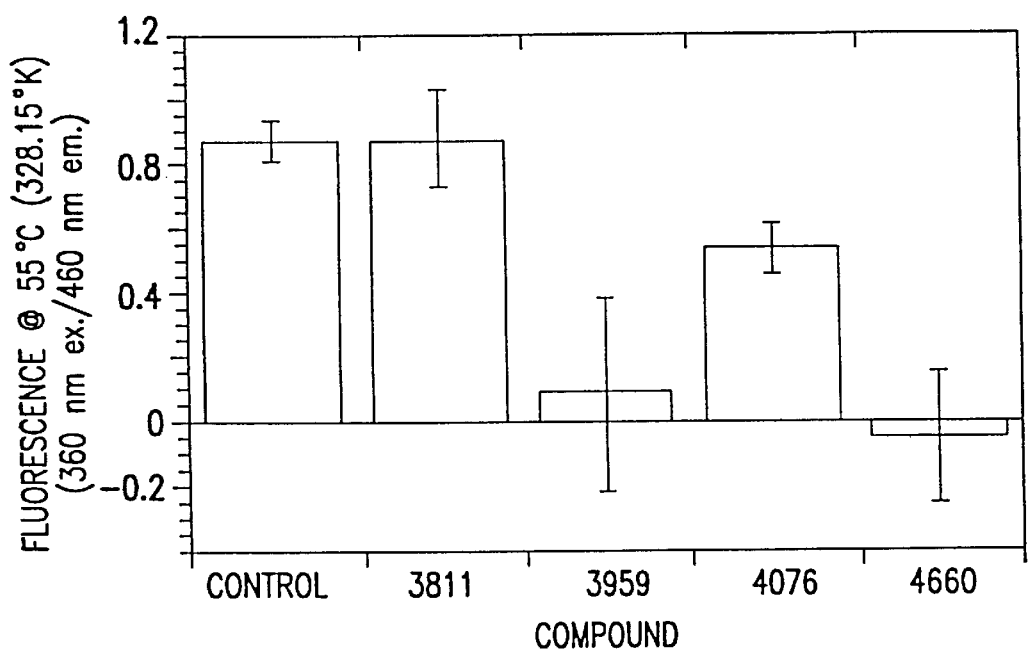
FIG. 12 shows the results of a single temperature microplate thermal shift assay of human α-thrombin in the presence of four different compounds in four separate experiments.

Results of a single temperature assay are shown in FIG. 12. The compounds 3DP-3811, 3DP-3959, 3DP-4076, and 3DP-4660 bind to the active site of human α-thrombin. The $K_i$'s (enzymatically determined) of these four compounds for human α-thrombin are of 20,000 nM, 250 nM, 25nM, and 8 nM, respectively. Each of these four compounds were equilibrated with human α-thrombin in separate 5 µl assay volumes in a 96 well plate. The final ligand concentration was 50 µM.

For the ligands that bind to human α-thrombin with higher affinity, low levels of fluorescence emission were observed, relative to the control reaction (human α-thrombin alone) at 55° C. The result for the sample containing the weakly binding ligand 3DP-3811 was little different from the result obtained for the control sample. The decrease in fluorescence emission for 3DP-4076 was not as large as expected, given its high affinity ($K_i$ of 25 nM) for human α-thrombin. This result could be due in part to the lower solubility of chloride salts of this compound.

The data in FIG. 12 clearly demonstrate the utility of the single temperature embodiment of the microplate thermal shift assay for quickly identifying ligands with binding affinities ($K_d$'s) of 250 nM or better when the ligand concentration is 50 µM.

EXAMPLE 14

Figure 13:
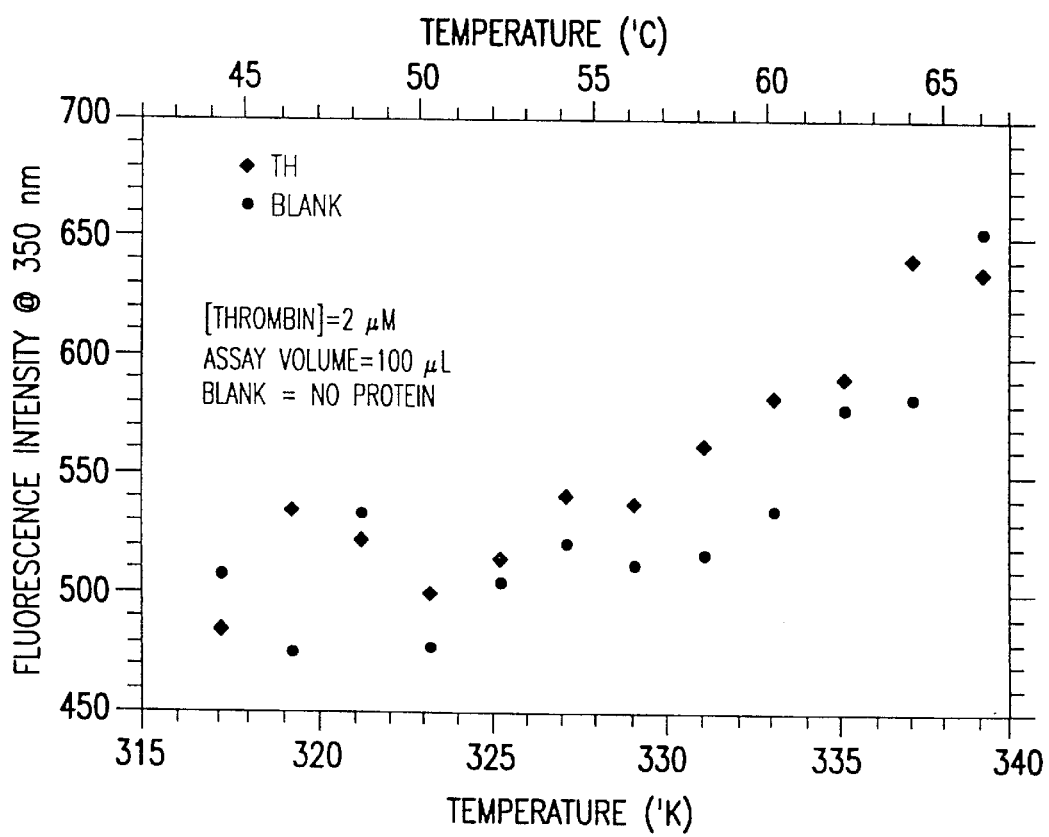
FIG. 13 shows the results of a microplate thermal shift assay of the intrinsic tryptophan fluorescence of human α-thrombin. In this assay, blank well fluorescence was not subtracted from sample fluorescence.
Figure 14:
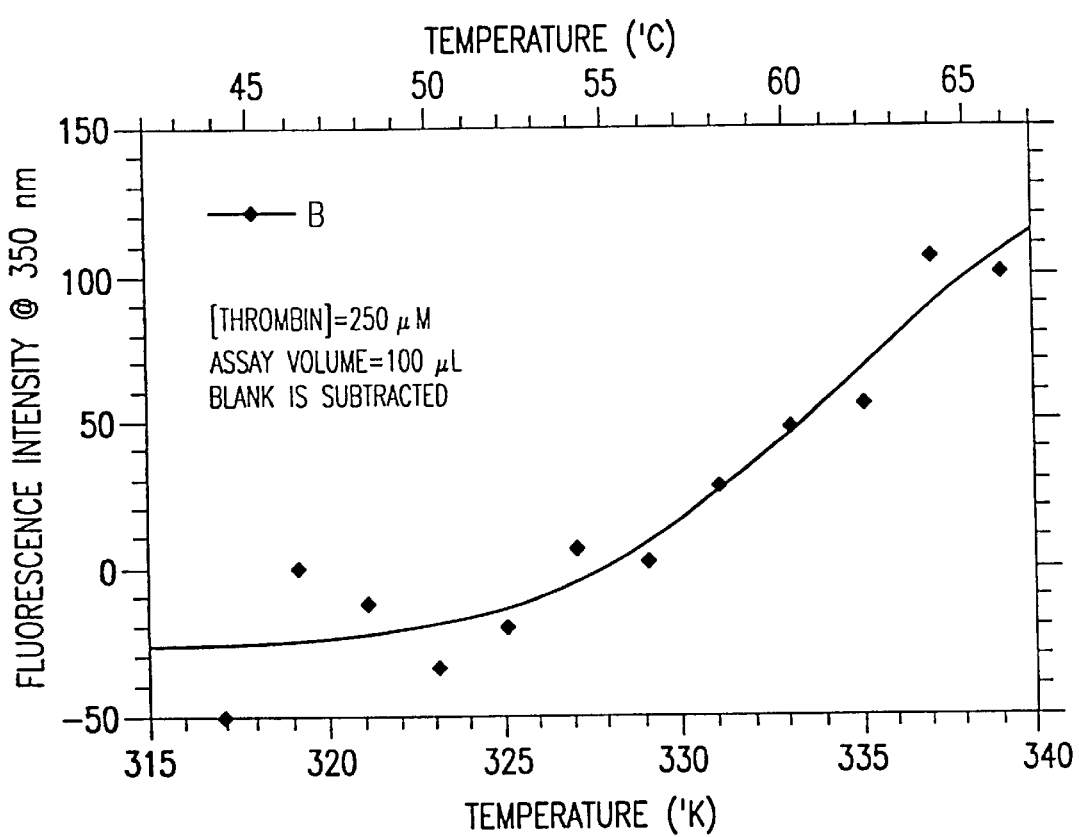
FIG. 14 shows the results of a microplate thermal shift assay of the intrinsic tryptophan fluorescence of human α-thrombin. In this assay, blank well fluorescence was subtracted from sample fluorescence.

Microplate Thermal Shift Assay of Intrinsic Protein Tryptophan Fluorescence Emission The intrinsic Trp fluorescence of human α-thrombin was assayed in a microplate thermal shift assay. 100 µL samples contained 2 µM human α-thrombin. The samples were exposed to light from a Xenon-Arc lamp at 280 nm. Emission was detected at 350 nm using the BioLumin 960 (Molecular Dynamics). Temperature cycling, between 44° C. and 66° C., was performed as described in previous examples. The results of the assay are shown in FIGS. 13 and 14. A small increase in fluorescence emission was observed at 350 nm with increasing temperature. However, this increase in fluorescence emission was barely detectable above the level of fluorescence in the blank wells that contained no protein (FIG. 13). Subtracting an average blank improved the signal to noise ratio (FIG. 14), but the observed unfolding transition was different from that typically observed in assays employing 1,8-ANS. In contrast to the transition observed using 1,8-ANS, the transition in FIG. 14 appears broader and has a midpoint temperature $T_m$ at 334.4±5.1°K, some five degrees higher than the $T_m$ observed for human α-thrombin in assays performed with 1,8-ANS.

EXAMPLE 15

Assay of Multi-Ligand Binding Interactions

As previously demonstrated, the thermal shift assay can be used for the screening of ligands for binding to single sites on target proteins. In light of the underlying physical principles upon which the microplate thermal shift assay is based, the near additivity of the free energy of ligand binding and protein unfolding, it is possible to employ the microplate thermal shift assay for analyzing multi-ligand binding interactions with a target protein. If the free energy of binding of different ligands binding to the same protein are nearly additive, then one can analyze multi-ligand binding systems, whether the ligands bind in a cooperative (positive) fashion or a non-cooperative (negative) fashion.

Multiple ligand binding to human α-thrombin was assayed in a microplate thermal shift assay. Human α-thrombin it has at least four different ligand binding sites: (1) the catalytic binding site; (2) the fibrin binding site (exosite I); (3) the heparin binding site (exosite II); and (4) the Na$^+$ binding site, located ~15Å from the catalytic site. First, independent binding of three individual ligands was assayed: 3DP-4660, Hirugen (hirudin 53–64) (Bachem), and heparin 5000 (CalBiochem). These ligands bind to the catalytic site, the fibrin binding site and the heparin binding site, respectively.

A stock thrombin solution was diluted to 1 µM in 50 mM Hepes, pH 7.5, 0.1 M NaCl, 1 mM CaCl$_2$, and 100 µM 1,8-ANS. Each thrombin ligand was included singly and in various combinations to 1 µM thrombin solutions at final concentrations of 50 µM each, except for heparin 5000, which was 200 µM. 100 µL of thrombin or thrombin/ligand (s) solution was dispensed into wells of a 96-well V-bottom polycarbonate microtiter plate. The plate was subjected to 3 minutes of heating in a thermal block capable of establishing a temperature gradient across the microplate, followed by 30 seconds cooling at 25° C., and subsequent reading in a fluorescence plate reader. Data were analyzed by non-linear least squares fitting.

Figure 15:
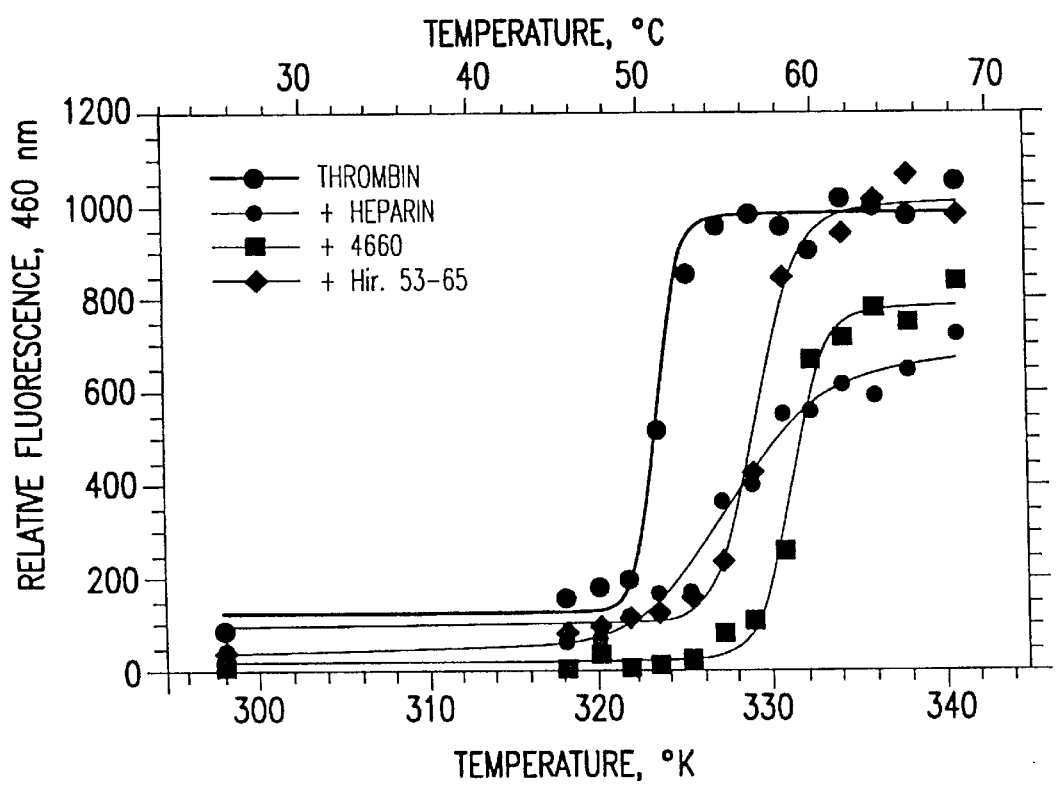
FIG. 15 shows the results of microplate thermal shift assays of single ligand binding interactions to three different classes of binding sites for human α-thrombin.
Figure 16:
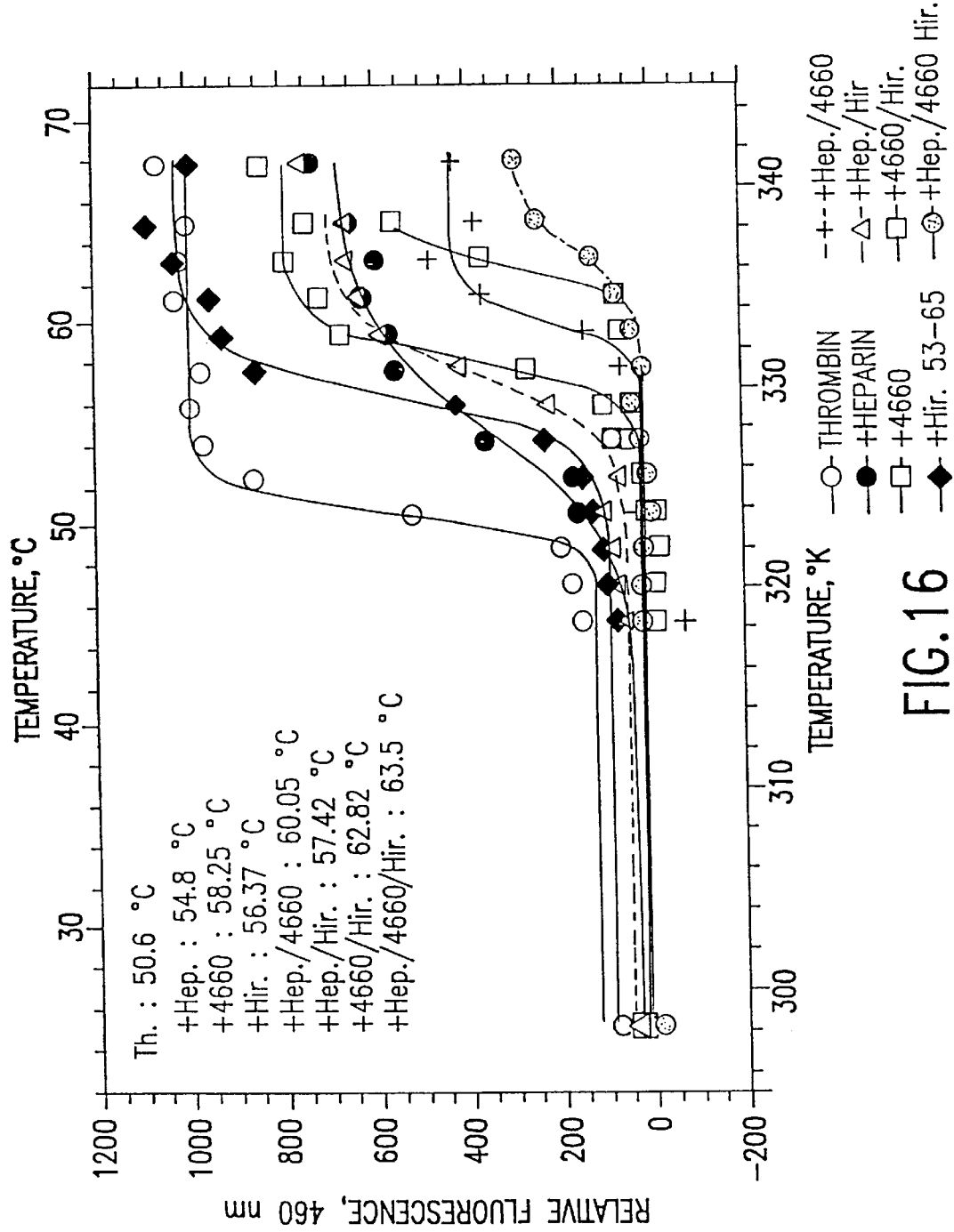
FIG. 16 shows the results of microplate thermal shift assays of multiligand binding interactions for human α-thrombin.

The results of these individual binding reactions are shown in FIGS. 15 and 16. The rank order of binding affinity was 3DP-4660 >Hirugen>heparin 5000, corresponding to $K_d$ values of 15 nM, 185 nM and 3434 nM, respectively, for the ligands binding at each $T_m$ (see Equation (4)).

The results reveal thermal unfolding shifts that are slightly smaller than would be expected if the free energies of binding were fully additive. For example, Hirugen alone displays a $\Delta T_m$ of 5.8° C., and 3DP-4660 alone displays a $\Delta T_m$ of 7.7° C. In combination, however, Hirugen and 3DP-4660 display a $\Delta T_m$ of 12.2° C. This result means that the binding affinity of one or both ligands is diminished when both ligands are bound, and is an example of negative cooperativity in binding between the fibrin and catalytic binding sites. Such a negatively cooperative effect is consistent with the human α-thrombin literature, in which the kinetics of hydrolysis of various chromogenic substrates were found to depend upon ligands binding to exosite I. Indeed, a 60% decrease in $K_m$ for the hydrolysis of D-phenylalanylpipecolyl arginyl-p-nitroanilide was observed when Hirugen was present (Dennis et al., *Eur. J. Biochem.* 188:61–66 (1990)). Moreover, there is also structural evidence for cooperativity between the catalytic site and exosite I. A comparison of the isomorphous structures of human α-thrombin bound to PPACK (a human α-thrombin catalytic site inhibitor) and Hirugen revealed conformational changes that occur at the active site as a result of Hirugen binding at the exosite I (Vijayalakshmi et al., *Protein Science* 3:2254–2271 (1994)). Thus, in the microplate thermal shift assay, the apparent cooperativity observed between the catalytic center and the exosite I is consistent with functional and structural data in the literature.

Similarly, when the binding of all three ligands was assayed, a $\Delta T_m$ of 12.9° C. was observed (FIG. 16). If the free energies of binding were fully additive, one would expect to observe a $\Delta T_m$ of 17.7° C. The observed result means that further negative cooperativity occurs via ligand binding at all three protein binding sites. This result is consistent with the literature. In a ternary complex with heparin and fibrin monomer, human α-thrombin has decreased activity toward tri-peptide chromogenic substrates and pro-thrombin (Hogg & Jackson, *J. Biol. Chem.* 265:248–255 (1990)), and markedly reduced reactivity with anti-thrombin (Hogg & Jackson, *Proc. Natl. Acad. Sci. USA* 86:3619–3623 (1989)). Also, recent observations indicate that ternary complexes also form in plasma and markedly compromise heparin anticoagulant activity (Hotchkiss et al., Blood 84:498–503 (1994)). A summary of these multi-ligand binding results is shown in Table 7.

The results in FIG. 15, FIG. 16, Table 7 illustrate the following advantages of using the microplate thermal shift assay to perform multi-variable analyses. First, the same microplate thermal shift assay can be used to simultaneously detect the binding of multiple ligands at multiple binding sites in a target protein. Second, the microplate thermal shift assay can be used to detect the same ligand binding to two or more sites in a therapeutic target. Third, the microplate thermal shift assay affords the detection of cooperativity in ligand binding. Information about ligand binding cooperativity can be collected and analyzed very quickly. Thus, multi-ligand binding experiments that would take months to perform using alternative technologies take only hours to perform using the microplate thermal shift assay.

TABLE 7

Microplate thermal shift assay for Ligands Binding to the Active Site, Exosite, and Heparin Binding Site of Human α-thrombin

| Protein/Ligand | [Ligand] ($\mu$M) | $T_m$ (° K) | $\Delta T_m$ (° K) | $K_d$ at $T_m$[a] (nM) | $K_d$ at 298[o,b] (nM) |
|---|---|---|---|---|---|
| Thrombin (TH) | none | 323.75 | 0.0 | | |
| TH/Heparin 5000 | 200 | 327.95 | 4.2 | 3434 | 470 |
| TH/Hirudin 53–65 | 50 | 329.52 | 5.8 | 185 | 23 |
| TH/3dp-4660 | 50 | 331.40 | 7.7 | 29 | 3 |
| TH/Heparin 5000 | 200 | 327.95 | | | |
| TH/Hep./Hir. | 50 | 330.57 | 2.6 | 4254 | 478 |
| TH/Heparin 5000 | 200 | 327.95 | | | |
| TH/Hep.3dp 4660 | 50 | 333.20 | 5.3 | 350 | 32 |
| TH/Hinidin 53–65 | 50 | 329.52 | | | |
| TH/Hir./Hep. | 200 | 330.57 | 1.1 | 75422 | 8467 |
| TH/Hinidin 53–65 | 50 | 329.52 | | | |
| Th/Hir.3dp-4660 | 50 | 335.97 | 6.5 | 117 | 9 |
| TH/3dp-4660 | 50 | 331.40 | | | |
| TH/3dp-4660/Hep | 200 | 333.20 | 1.8 | 38205 | 351 |
| TH/3dp-4660 | 50 | 331.40 | | | |
| Th/3dp-4660/Hir. | 50 | 335.97 | 4.6 | 731 | 54 |

[a]Calculations for $K_d$ at $T_m$ were made using equation (1) with $\Delta H_u^{T°}$ = 200.0 kcal/mole, as observed for pre-thrombin 1 by Lentz et al., (1994), and an estimated $\Delta C_{pu}$ = 2.0 kcal/mole-° K; and $K_d$ = 1/$K_a$.
[b]Estimates for $K_d$ at T = 298° K were make using the equation (3), where $\Delta H_L^T$ is estimated to be –10.0 kcal/mole.

EXAMPLE 16

Screening Biochemical Conditions that Increase Human α-thrombin Stability

The microplate thermal shift assay was used, with four different fluorophores, to simultaneously screen the effects of multiple pH values, sodium chloride concentrations, and reduction-oxidation compounds on human α-thrombin stability. Thrombin solution was diluted to 1 $\mu$M in 50 mM Hepes, pH 7.5, NaCl at either 0.1 M or 0.5 M, 10 mM EDTA, 10 mM CaCl$_2$, 10 mM dithiothreitol, 10 1 mM CaCl$_2$, and 100 $\mu$M 1,8-ANS, 10% (v/v) glycerol, or 0.1% (w/v) polyethylene glycol (PEG) 6000. Reaction volume was 100 $\mu$L.

Figure 17A:
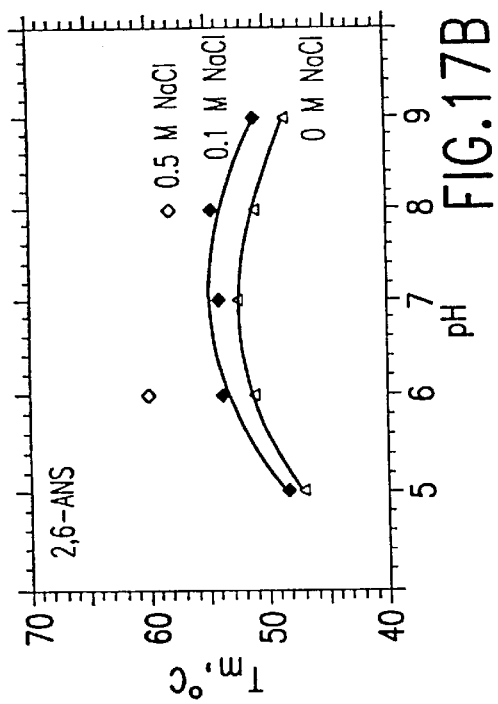
FIGS. 17A–D show the results of microplate thermal shift assays of the effect of pH and various sodium chloride concentrations on the stability of human α-thrombin.
Figure 17B:
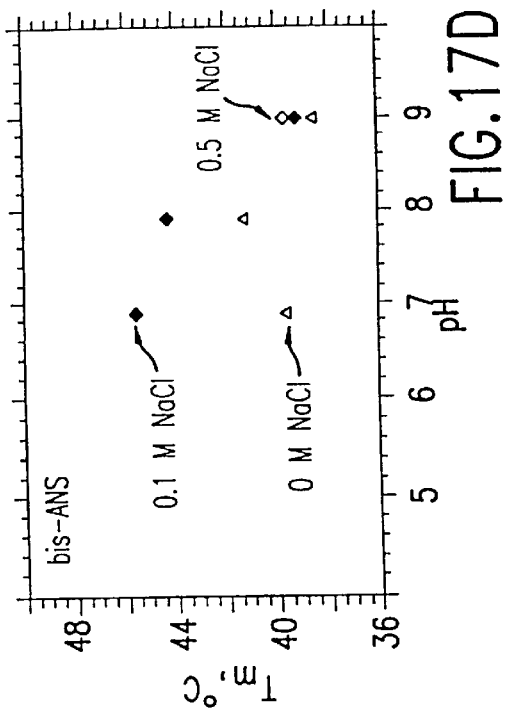
Figure 17C:
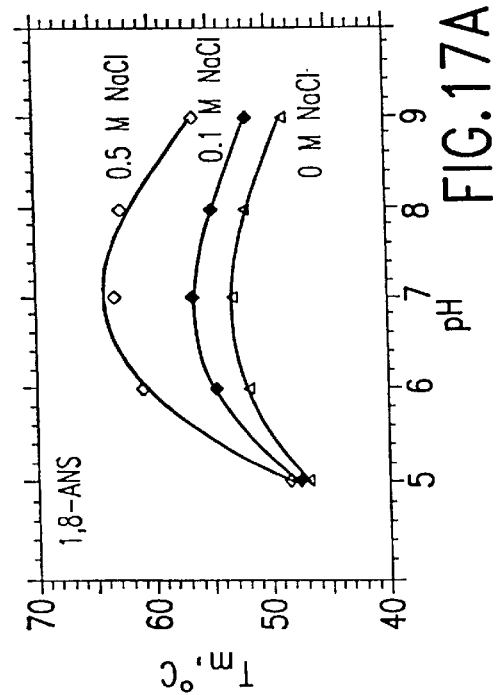
Figure 17D:
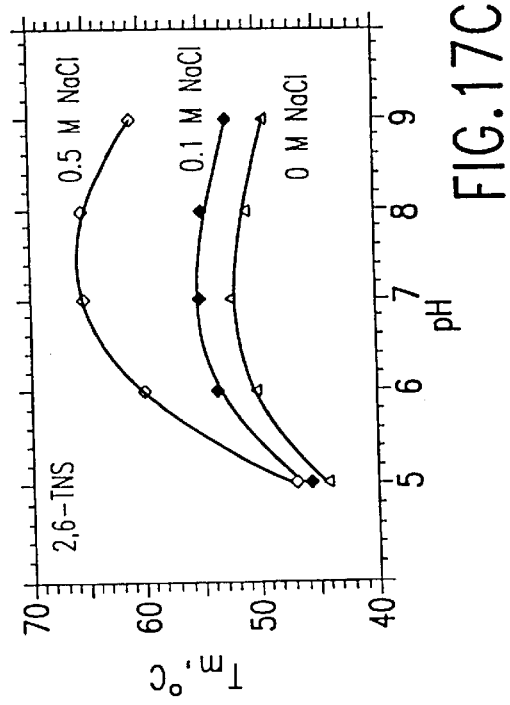
Figure 18:
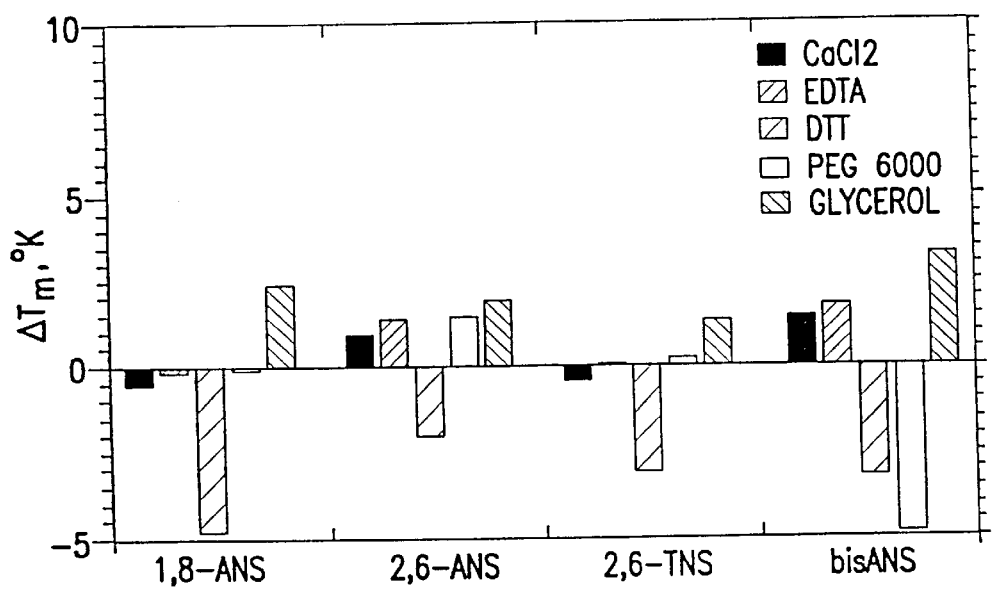
FIG. 18 shows the results of microplate thermal shift assays of the effect of calcium chloride, ethylenediaminetetraacetic acid, dithiothreitol, and glycerol on the stability of human α-thrombin.

The results of these multi-variable experiments are shown in FIGS. 17A–D and FIG. 18. FIGS. 17A–D summarize the stability data collected in a single 96 well plate for human α-thrombin. In FIG. 17A, the fluorophore is 1,8-ANS. In FIG. 17B, the fluorophore is 2,6-ANS. In FIG. 17C, the fluorophore is 2,6-TNS. In FIG. 17D, the fluorophore is bis-ANS. The results in FIGS. 17A–D show a pH optimum of about 7.0 and an increase in stability with increasing NaCl concentration. A $\Delta T_m$ of about 12° C. was observed when the NaCl concentration was increased from 0 to 0.5 M. FIG. 18 shows a stabilizing effect of 10% glycerol and a destabilizing effect of dithiothreitol. From FIGS. 17A–D and 18 is evident that the flourophores 1,8-ANS and 2,6-TNS are most effective in the microplate thermal shift assay.

The stabilizing effect of NaCl is particularly interesting since there are recent reports in the literature of a weak Na$^+$ binding site ($K_d$ of 30±3 mM in 5 mM Tris buffer pH 8.0, 0.1% PEG, 25° C.) approximately 15 Å from the catalytic center of thrombin (Dang et al., Nature Biotechnology 15:146–149 (1997)). Using equation (1), it is possible to estimate the NaCl binding to be ~6 mM near the $T_m$ (53° C.) in 50 mM Hepes pH 8.0 buffer (zero and 0.10 M NaCl).

The additional stabilization that occurs at a NaCl concentration of greater than 0.10 M may come from additional Na$^+$ and/or Cl$^-$ binding events summed over the entire structure of human α-thrombin. Alternatively, the source of this further stabilization may come from less specific salting out effect that is usually observed at 0.5 to 2 M NaCl and is due to the preferential hydration of proteins induced by salts (Timasheff & Arakawa, In: Protein Structure, A Practical Approach, T. E. Creighton, ed., IRL Press, Oxford, UK (1989), pp. 331–354)). The stabilizing effect of glycerol on proteins has been attributed to a balance between the preferential exclusion of glycerol (i.e. preferential hydration of proteins) and the specific binding to polar regions on the surface of proteins (Timasheff & Arakawa, In: Protein Structure, A Practical Approach, T. E. Creighton, ed., IRL Press, Oxford, UK (1989), pp. 331–354)).

EXAMPLE 17

Screening Biochemical Conditions that Increase D (II) FGF Receptor 1 Stability

The microplate thermal shift assay was used to simultaneously screen the effects of multiple biochemical conditions on D(II) FGF receptor 1 stability. The assays were performed by mixing 1 $\mu$L of D(II) FGFR1 (from a 500 $\mu$M concentrated stock in 50 mM HEPES pH 7.5) with 4 $\mu$L of each biochemical condition in wells of a 96-well polycarbonate microtiter plate. Final protein concentration after mixing was 100 $\mu$M and final 1,8-ANS concentration was 200 $\mu$M. Biochemical conditions were tested as follows: The pH's tested were 5 (Na acetate), 6 (MES), 7 (MOPS), 8 (HEPES), and 9 (CHES), with final buffer concentrations of 50 mM.

The salt concentrations tested were 0.1 or 0.5 M NaCl. Additives were tested in 50 mM MOPS, pH 7, 0.1 M NaCl, at final concentrations of 1 mM (EDTA, dithiothreitol), 10 mM (CaCl$_2$, MgCl$_2$, MgSO$_4$, NiSO$_4$),50 mM (arginine), 100 mM ((NH$_4$)$_2$SO$_4$, LiSO$_4$, Na$_2$SO$_4$, ZnSO$_4$), 5% w/v (polyethylene glycol 6000), and 10% v/v glycerol.

Thermal denaturation profiles were generated as previously described for thrombin, aFGF, Factor D, and Factor Xa, by incremental heating of the microplate followed by a fluorescence reading after each temperature increase. Data were analyzed by non-linear least squares fitting as described previously.

Figure 19:
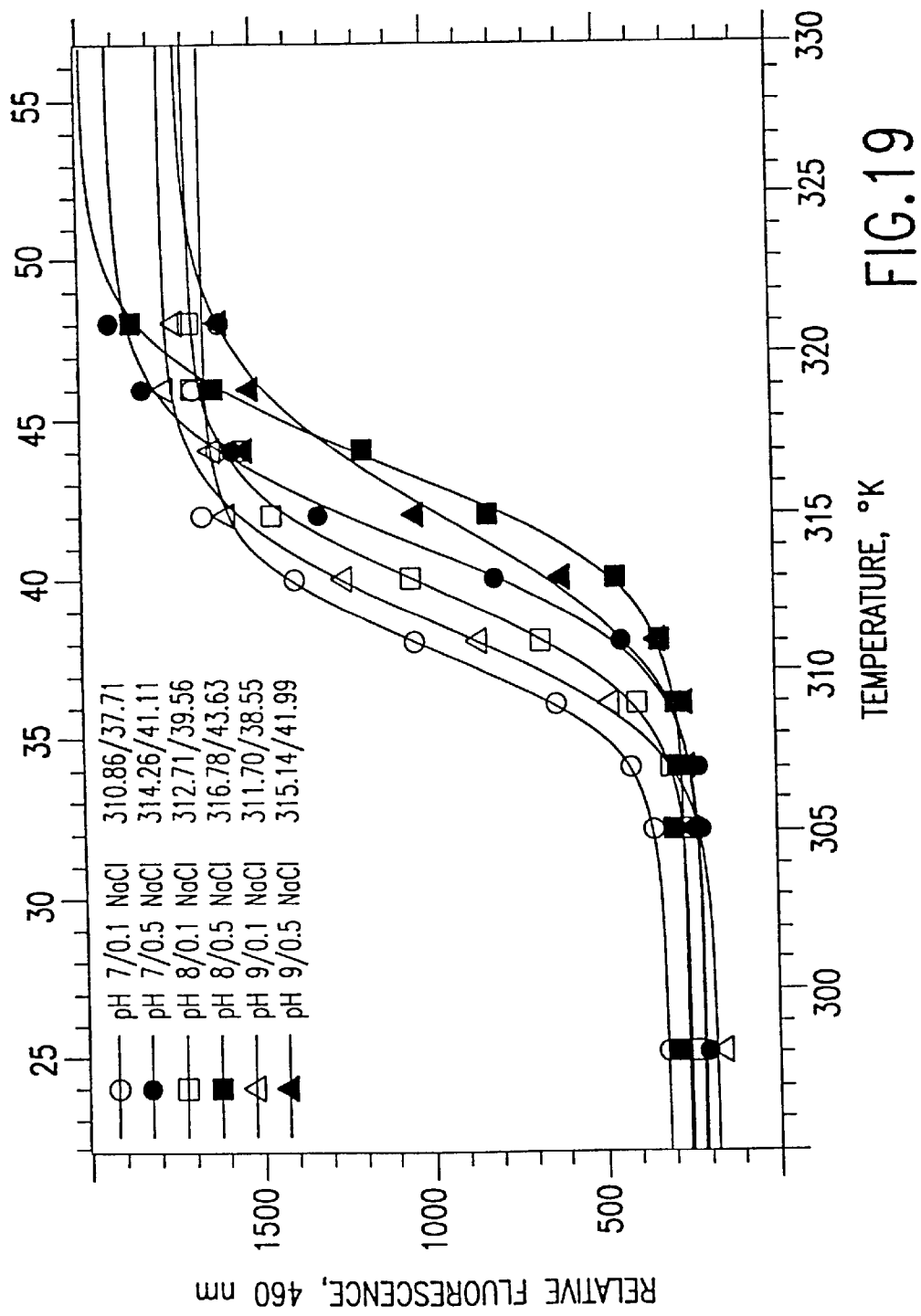
FIG. 19 shows the results of microplate thermal shift assays of the effect of pH and sodium chloride concentration of the stability of human D(II) FGF receptor 1.
Figure 20:
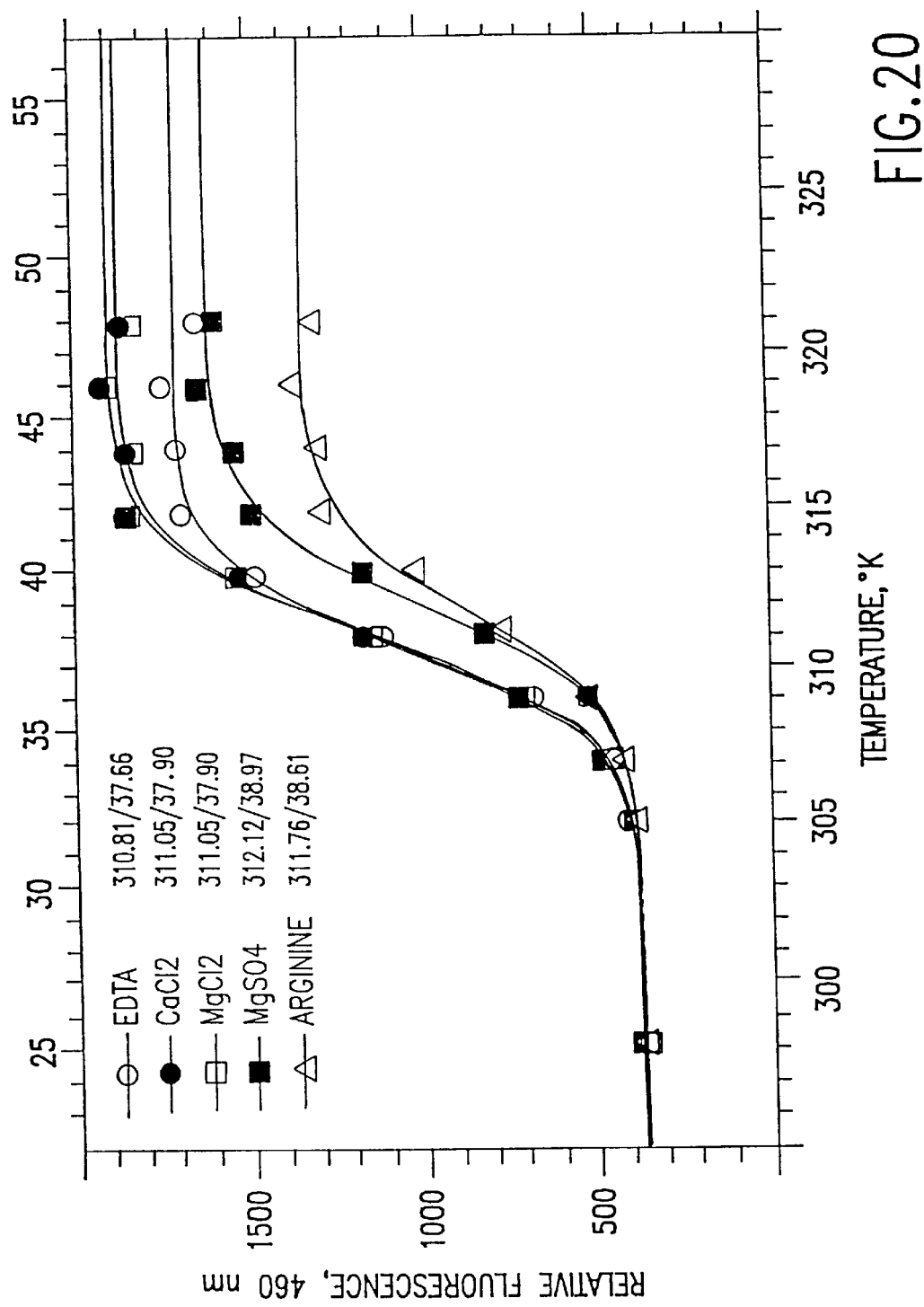
FIG. 20 shows the results of microplate thermal shift assays of the effect of various biochemical conditions on the stability of human D(II) FGF receptor 1.
Figure 21:
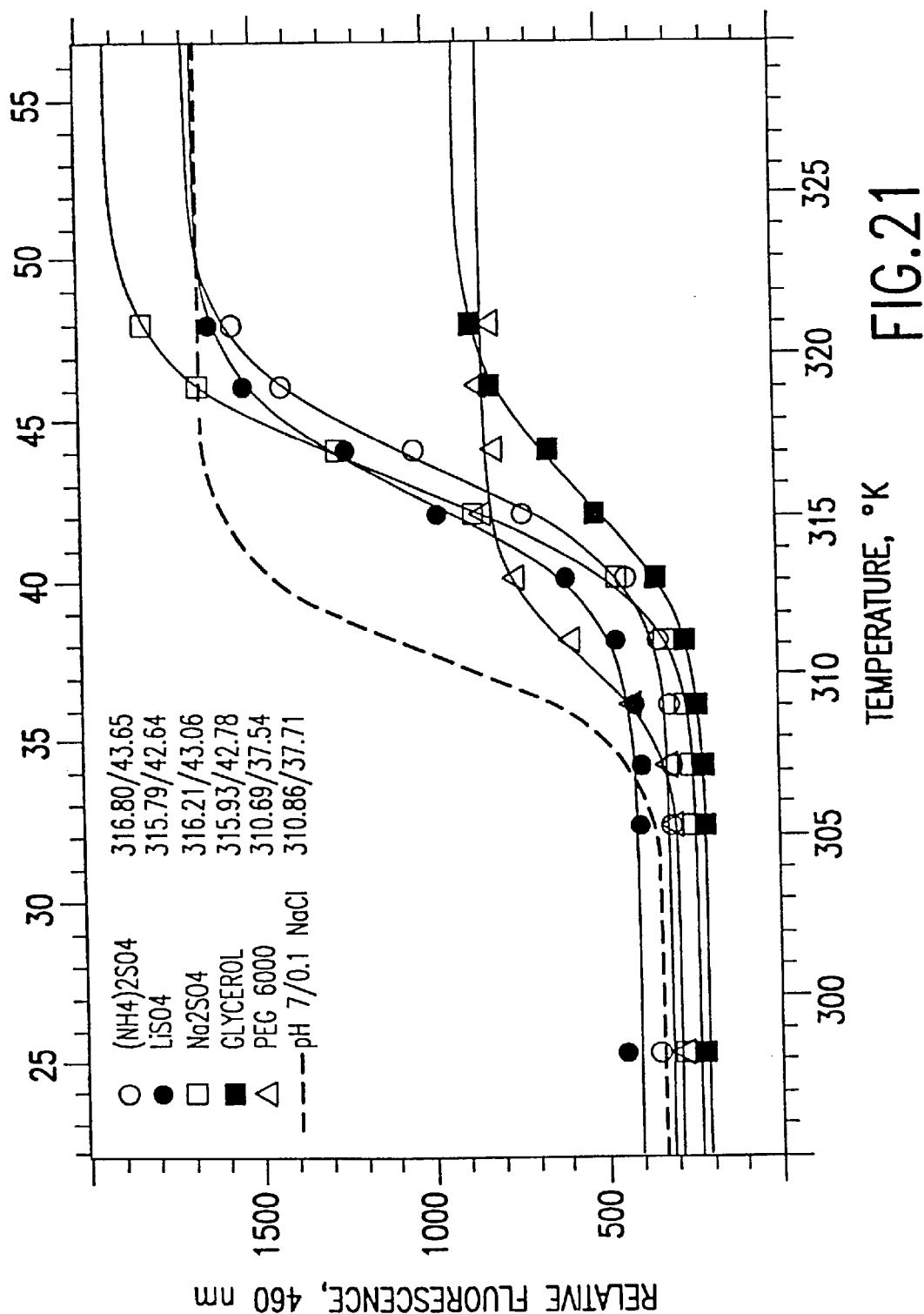
FIG. 21 shows the results of microplate thermal shift assays of the effect of various biochemical conditions on the stability of human D(II) FGF receptor 1.
Figure 22:
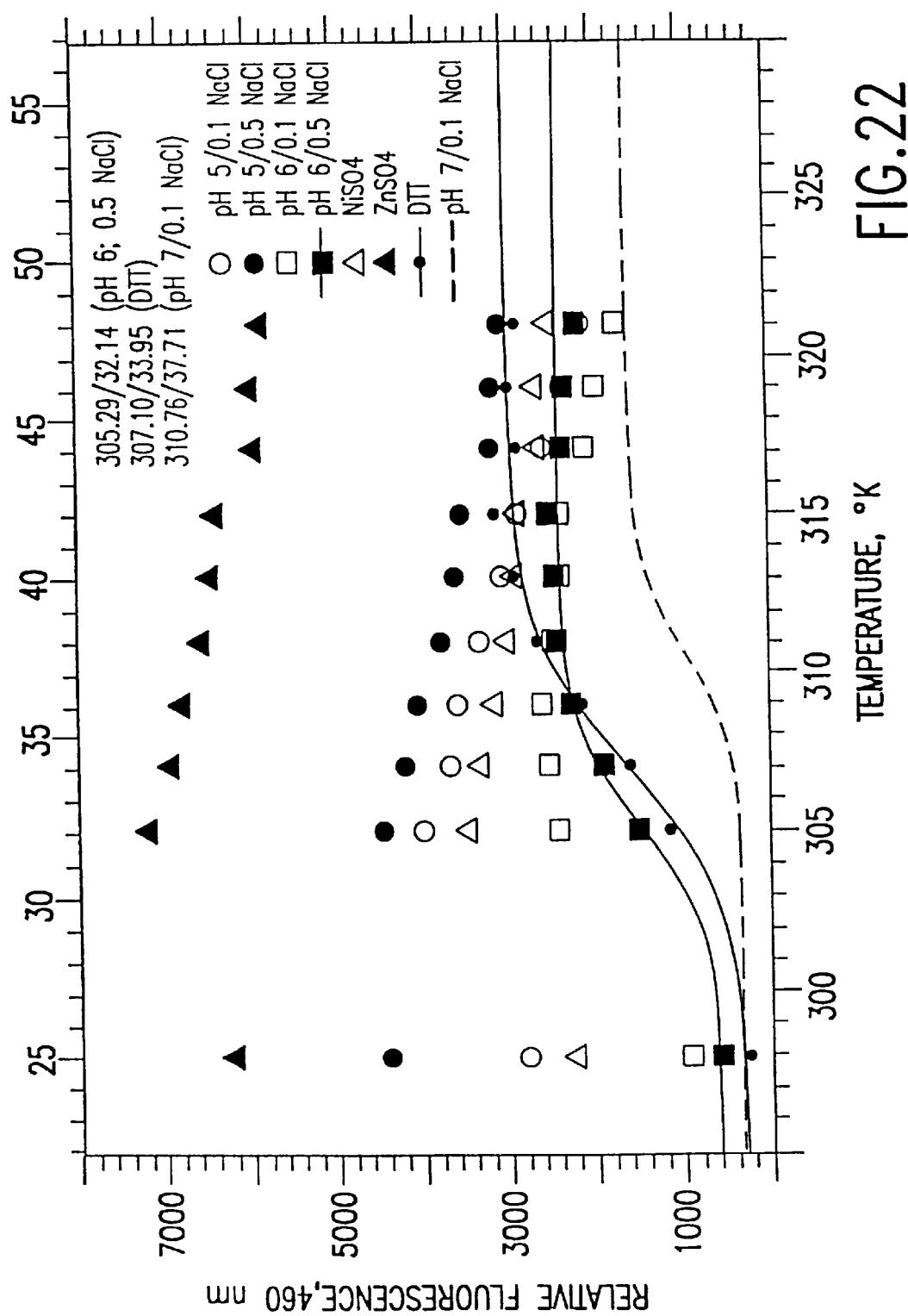
FIG. 22 shows the results of microplate thermal shift assays of the effect of various biochemical conditions on the stability of human D(II) FGF receptor 1.
Figure 23:
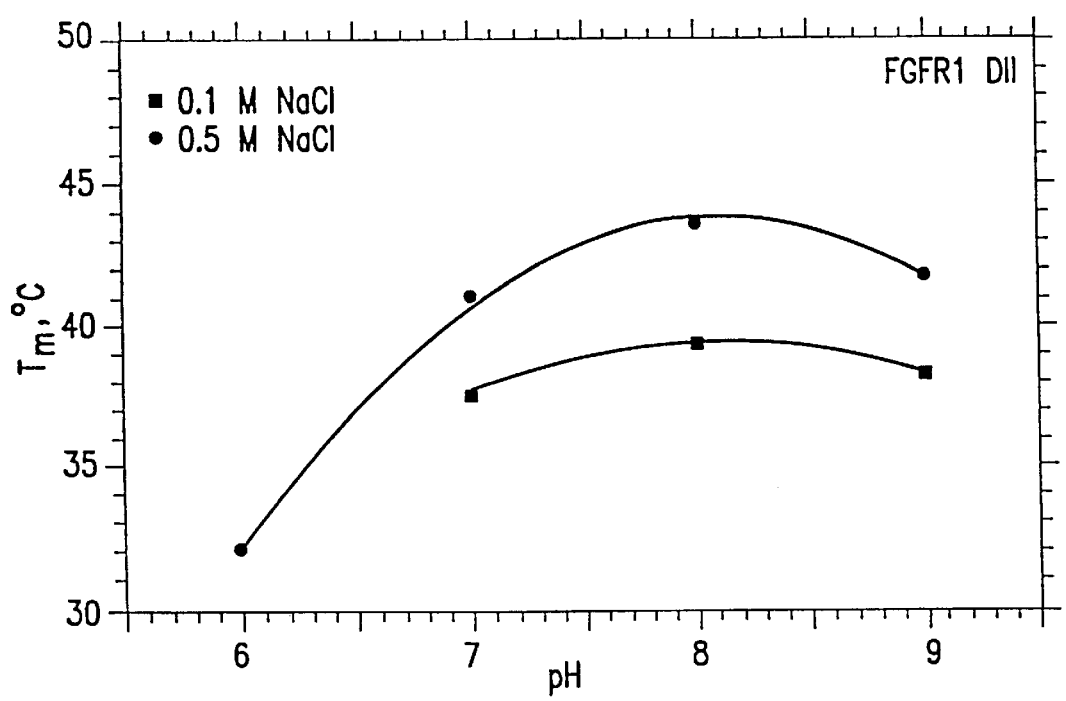
FIG. 23 shows the results of microplate thermal shift assays of the effect of various biochemical conditions on the stability of human D(II) FGF receptor 1.
Figure 24:
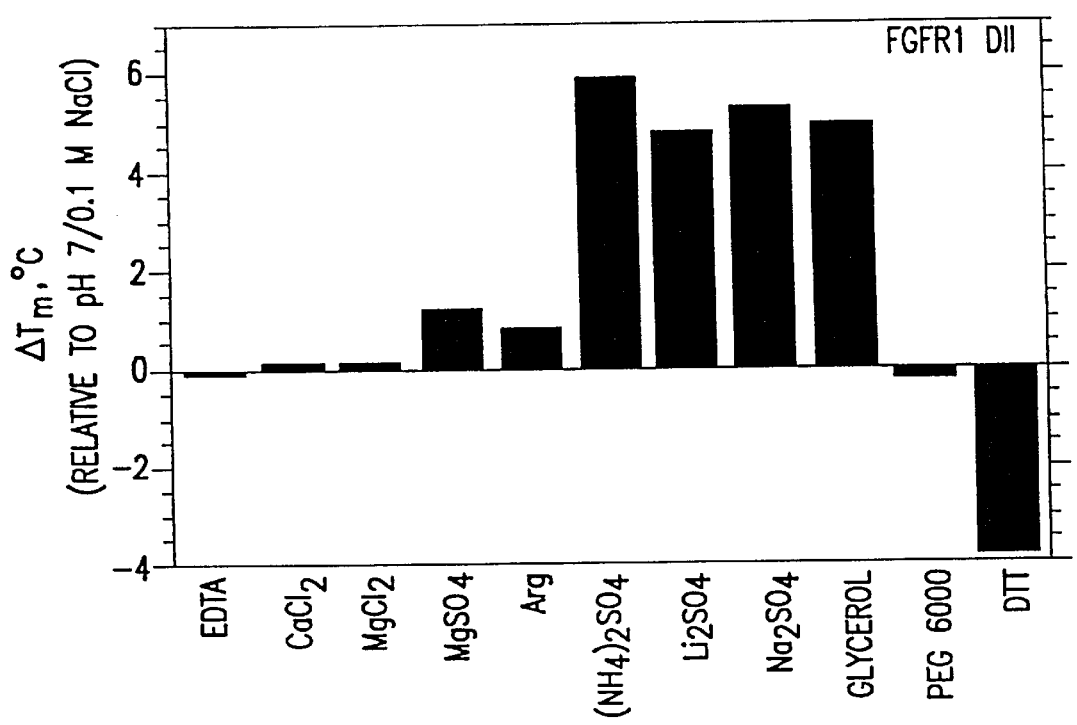
FIG. 24 shows the results of microplate thermal shift assays of the effect of various biochemical conditions on the stability of human D(II) FGF receptor 1.

The results of these multi-variable experiments are shown in FIGS. 19–24. As shown in FIG. 19, stability increased with increasing NaCl concentration. A $\Delta T_m$ of about 5° C. was observed as NaCl concentration was increased from 0.1 to 0.5 M. As shown in FIG. 20, both MgSO$_4$ and arginine stabilized the protein. As shown in FIG. 21, 10% glycerol stabilized the protein. Further, salts of the Hofmeister series such as $Li_2SO_4$, $Na_2SO_4$, $(NH_4)_2SO_4$ and $MgSO_4$ all had stabilizing effects (FIG. 21). As shown in FIG. 22, dithiothreitol destabililzed the protein. These results are not very different form that of human α-thrombin. As shown in FIG. 23, a pH optimum of about 8.0 was observed. The relative stabilizing effects of EDTA, $CaCl_2$, $MgCl_2$, $MgSO_4$, arginine, $(NH_4)_2SO_4$, $Li_2SO_4$, $Na_2SO_4$, glycerol, polyethylene glycol 6000, and dithiothreitol are shown in FIG. 24.

EXAMPLE 18

Screening Biochemical Conditions that Increase Urokinase Stability

The microplate thermal shift assay was used to simultaneously screen the effects of multiple biochemical conditions on human urokinase stability. This experiment was performed by mixing 1 μL of urokinase (from a 371 5M concentrated stock in 20 mM Tris pH 8) with 4 μL of each biochemical condition in wells of a 96-well polycarbonate microtiter plate. Final protein concentration 13.5±0.2% was obtained at pH 8.0 and 0.5 M NaCl. This yield could be increased to 15.5±0.3% if glycerol was present at 7% (v/v). A further increase in $His_6$-D(II)-FGFRI refolding yield to about 18% was observed when the pH was increased to 8.9. In fact, increasing the pH from 8.0 to 8.9 improved the yields in all experiments. These results demonstrate that a pH between 8 and 9, and 7% glycerol, are two important conditions that facilitate D(II)-FGFRI folding. Each of these conditions increased the folded protein yield by about 15 to 20% over the starting conditions at pH 8.0 and 0.5 M NaCl.

Importantly, the effects of pH and glycerol appear to be nearly additive. The increased yield of refolded protein at pH 8.9 and 7% glycerol was found to be 17.8%, 32% higher than the yield obtained at a pH 8.0 and 0.5 M NaCl (13.5±0.2% yield). The near additivity of refolding determinants has important consequences since it suggests that the small individual free energy components that comprise the overall free energy of folding can be incrementally combined to optimize the yield of folded protein.

TABLE 8

Factorial Experiment to Optimize the Protein Folding Yield for Immobilized $His_6$D(II)-FGFRI at a final Gdn-HCl concentration of 0.38 M[a]

|        | 500 nM NaCl | 50 mM NaCl | 7% Glycerol/ 50 mM NaCl |
|--------|-------------|------------|-------------------------|
| pH 8.0 | 13.3%[b]    | 9.3%       | 15.1%                   |
| pH 8.0 | 13.6%       | 9.4%       | 15.8%                   |
| pH 8.9 | 16.1%       | 13.5%      | 17.8%                   |
| pH 8.9 |             | 10.3%      | 17.8%                   |

[a]Refolding was initiated by diluting a 3.2 mL suspension of $Ni^{2+}NTA/6M$ Gdn-HCl to 50 mL in the respective refolding buffers (1:15.6 dilution) so that the final Gdn-HCl concentration was 0.38 M.
[b]Yields are based on measured $A_{280}$ values for fractions eluted off a Heparin Sepharose column. The immobilized protein concentration was 1.2 mg/mL as measured by a Bio-Rad protein assay. Since the column size was 21 mL, 25.2 mg of D(II) FGFR1 was bound to the resin.

Results of a second round of refolding experiments at a final Gdn-HCl concentration of 0.09 M revealed that the Gdn-HCl is an even more important factor affecting the folding of $His_6$-D(II)FGFR1 (Table 9). At pH 8.0 and 0.5 M after mixing was 74 μM and final 1,8-ANS concentration was 200 μM. Biochemical conditions were tested as follows: The pH's tested were 5 (acetate), 6 (MES), 7 (MOPS), 8 (HEPES), and 9 (CHES) with final buffer concentrations of 50 mM. The salt concentrations tested were 0.1 or 0.5 M NaCl. Glycerol was tested at 10% v/v in 50 mM MOPS, pH 7, 0.1 M NaCl.

Thermal denaturation profiles were generated as previously described for thrombin, aFGF, Factor D, D(II) FGFR1, and Factor Xa, by incremental heating of the microplate followed by a fluorescence reading after each temperature increase. Data were analyzed by non-linear least squares fitting as described previously.

Figure 25:
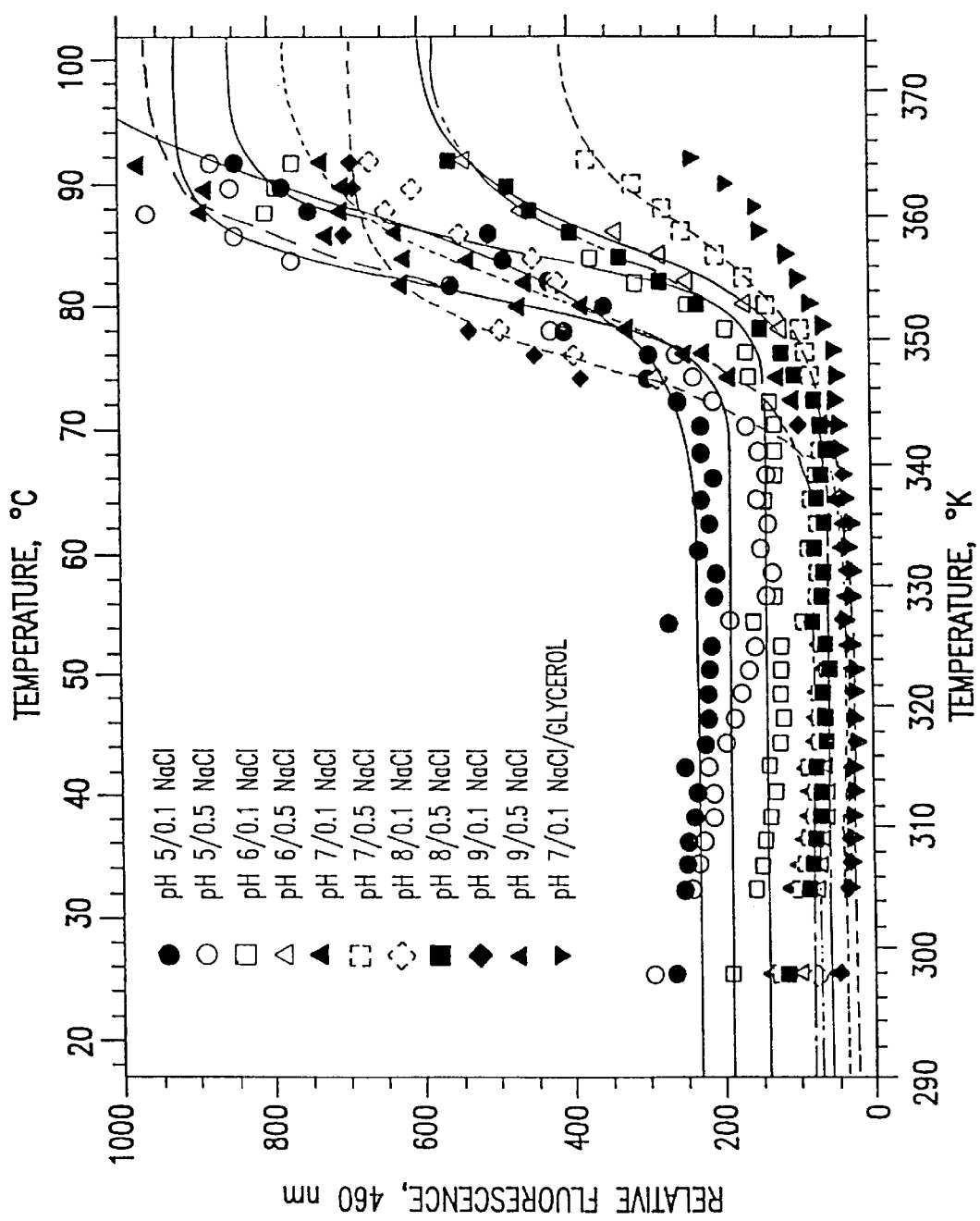
FIG. 25 shows the results of microplate thermal shift assays of the effect of various biochemical conditions on the stability of human urokinase.

The results of these multi-variable experiments are shown in FIG. 25. A pH optimum of about 7.0 was observed. Increasing concentrations of sodium chloride stabilized the protein. 10% glycerol also stabilized the protein. These results are consistent with the results reported in the literature (Timasheff & Arakawa, In: *Protein Structure, A Practical Approach*, T. E. Creighton, ed., IRL Press, Oxford, UK (1989), pp. 331–354).

FIGS. 17–25 illustrate the advantage of using the microplate thermal shift assay to simultaneously screen for multi-variable biochemical conditions that optimize protein stability. Using the methods and apparatus of the present invention, one can rapidly screen large arrays of biochemical conditions for conditions that influence the stability of proteins. Thus, the present invention can be used to rapidly identify biochemical conditions that optimize protein shelf-life.

EXAMPLE 19

Screening Biochemical Conditions that Facilitate Protein Folding

Factorial experiments were performed to identify biochemical conditions that increased the yield of correctly folded $His_6$-D(II)-FGFR1. $His_6$-D(II)-FGFR1 is recombinant D(II) FGF receptor 1 protein, to which a polyhistidine tag is attached to the N-terminus. The results are summarized in Table 8. When the final guanidinium hydrochloride concentration was 0.38 M, a refolded protein yield of NaCl, decreasing the Gdn-HCl concentration to 0.09 M doubled the refolded protein yield, relative to the yield obtained at pH 8.0, 0.5 M NaCl, and 0.38 M Gdn-HCl (Table 9). In accordance with the results obtained at a Gdn-HCl concentration of 0.38 M, the yield of refolded $His_6$-D(II)-FGFR1 in 0.09 M Gdn-HCl was also increased in the presence of glycerol. These results suggest that the improved yield of refolded $His_6$D(II)-FGFR1 in glycerol (5 to 10%) and lower Gdn-HCl concentration are additive. Further, the results in Table 9 reveal that the Hofmeister salt $Na_2SO_4$ increases the yield of refolded protein almost as well as 5 to 10% glycerol.

TABLE 9

Factorial Experiment to Optimize the Protein Folding Yield for Immobilized $His_6$_D(II)-FGFR1. Final Gdn-HCl of 0.09 M[a]

|        | 500 mM NaCl | 50 mM NaCl | 5% Glycerol 50 mM NaCl | 10% Glycerol 50 mM NaCl | 100 mM $Na_2SO_4$ | 300 mM $Na_2SO_4$ |
|--------|-------------|------------|------------------------|-------------------------|-------------------|-------------------|
| pH 8.0 | 25.6%[b]    | 29.7%      | 36.5%                  | 35.6%                   | 32.2%             | 33.4%             |

[a]Refolding was initiated by diluting a 7.5 mL suspension of $Ni^{2+}NTA/6M$ Gdn-HCl to 50 mL in the respective refolding buffers (1:6.7 dilution) so that the final Gdn-HCl concentration was 0.09 M.
[b]Yields are based on measured $A_{280}$ values for fractions eluted off a Heparin Sepharose column. The immobilized protein concentration was 1.6 mg/mL, as measured by Bio-Rad protein assay. Since the column size was 20 mL, 32 mg of D(II) FGFR1 was bound to the resin.

Upon comparison of ihe biochemical conditions that increase the yield of refolded $Ni^{2+}NTA$ bound $His_6$-D(II)-FGFR1 (Tables 8 and 9) and those conditions that increase the overall protein stability of $His_6$-D(II)-FGFR1 (FIGS. 19–24), it is clear that there is a strong correlation between the protein folding results and the protein stability results. Glycerol, salts of the Hofmeister series, and pH 8.5 to 8.9 improve protein folding yield and overall protein stability of $His_6$-D(II)-FGFR1.

Figure 26:
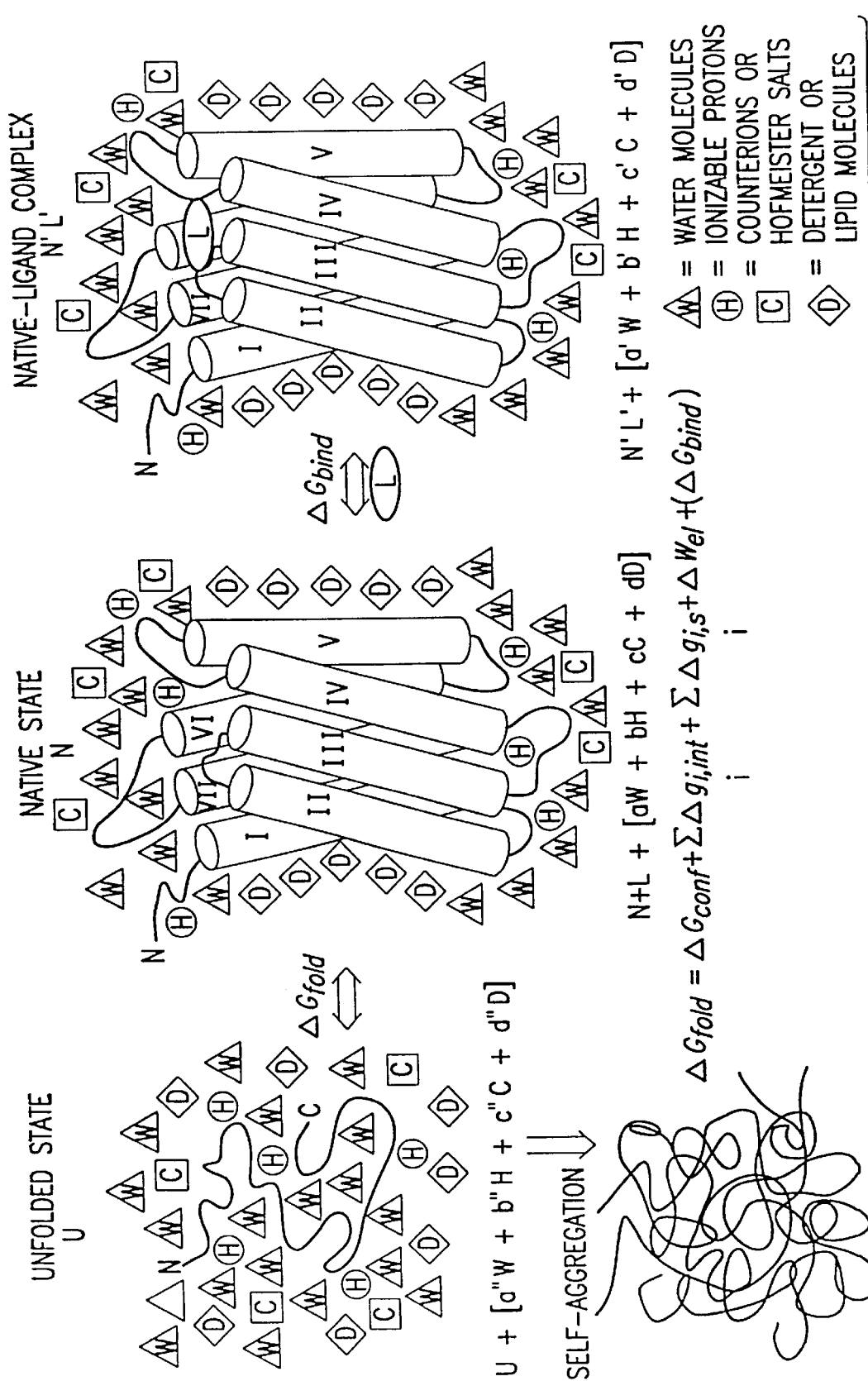
FIG. 26 is a schematic diagram of a thermodynamic model for the linkage of the free energies of protein folding and ligand binding.

These results are consistent with the model of protein folding in FIG. 26. If the aggregation of unfolded $His_6$-D (II)-FGFR1 is suppressed when immobilized to $Ni^{2+}NTA$, and a simple two state equilibrium exists between U and N, then the factors that influence the relative position of the equilibrium between U and N should be the same whether one starts from U (in the refolding experiment) or start from N (in the microplate thermal shift assay protein stability screen). Since thermodynamics are path independent, only the initial and final states of this reaction should be important. Since similar biochemical conditions facilitate protein stability and folded protein yield, the simple model for protein folding depicted in FIG. 26 is accurate for this protein. Thus, the microplate thermal shift assay can serve as a rapid and general method for screening biochemical conditions that optimize protein folding.

EXAMPLE 20

Figure 28:
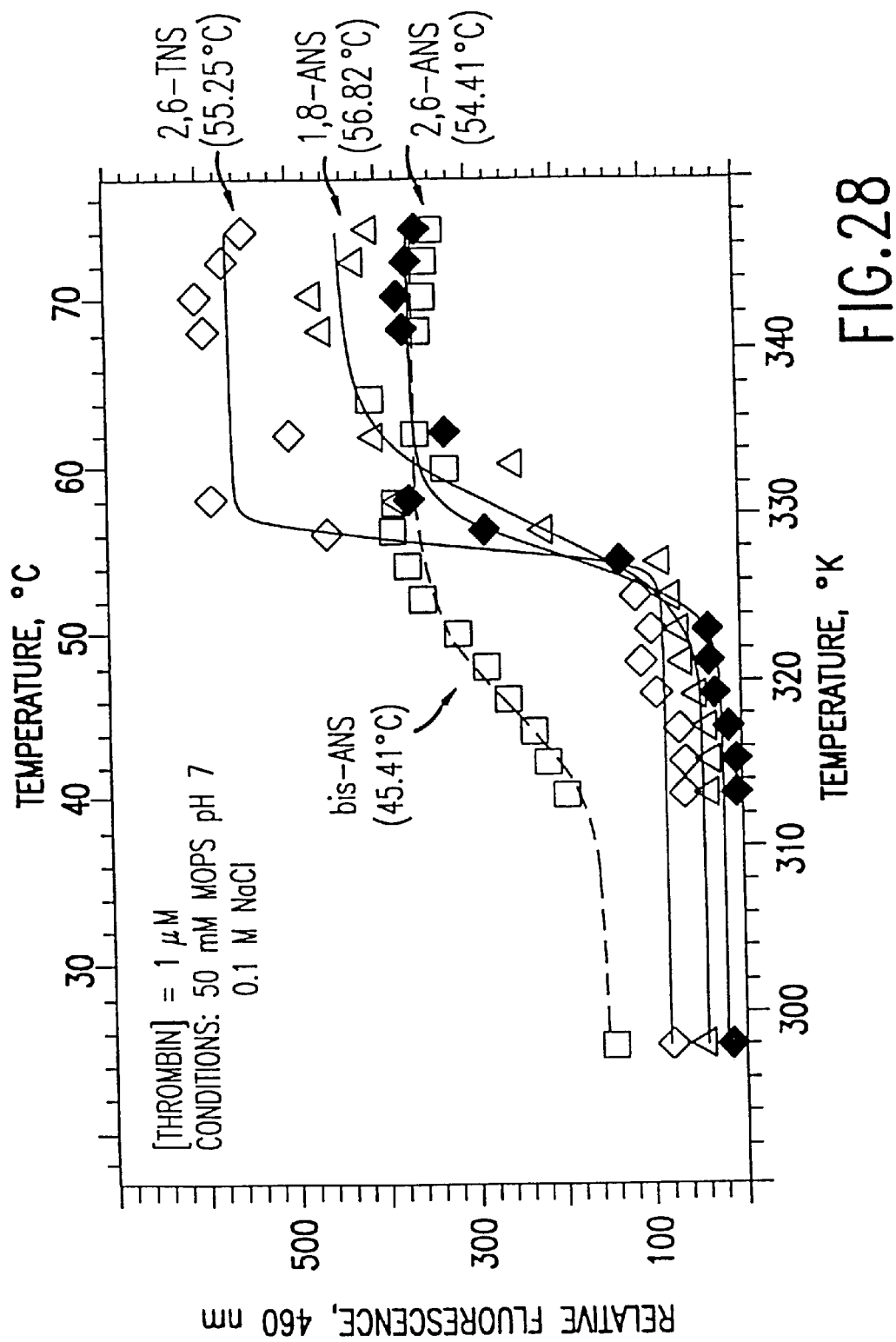
FIG. 28 shows the results of microplate thermal shift assays of human α-thrombin stability using various fluorophores.

FIG. 28 shows the results of microplate thermal shift assays of using each of four fluorescence probe molecules: bis-ANS, 2,6-TNS, 1,8-TNS, and 2,6-ANS. Thrombin solution was diluted to 1 $\mu$M in 50 mM Hepes, pH 7.5, and 0.1 M NaCl.

EXAMPLE 21

Comparison of Assay Results for a Fluorescence Scanner and a Charge Coupled Device Camera A Gel Documentation and Analysis System (Alpha Innotech Corp., San Leandro, Calif.) was used to perform a microplate thermal shift assay. This system uses a CCD camera to detect fluorescence emission from stained gels, dot blot assays, and 96 well plates. The excitatory light source was a long wavelength UV trans-illumination box located directly below the CCD camera. The 96 well plate to be assayed was placed on the trans-illumination box within the focal viewing area of the CCD camera (21×26 cm).

A 2 $\mu$M solution of human $\alpha$-thrombin was prepared in 50 niM Hepes, pH 7.5, 0.1 M NaCl by diluting a 34 $\mu$M stock solution (1:17) of purified human $\alpha$-thrombin (Enzyme Research Labs, Madison, Wis.). The human $\alpha$-thrombin solution also contained 100 $\mu$M 1,8-ANS. 100 $\mu$L of the human $\alpha$-thrombin-1,8-ANS solution was aliquoted into each of twelve wells of a single row (row A) of a V-bottom polycarbonate microplate (Costar). A gradient block (RoboCycler™, Stratagene) was used to heat the twelve samples, from 44 to 66° C., across the rows of the microplate. i.e. a temperature gradient of 2° C. per well was established. Thus, well A1 was at 66° C. and well A12 was at 44° C. The control solution that contained 100 $\mu$M 1,8 ANS in the same buffer (no protein) was placed in each of wells B1 to B12. After adding a drop of mineral oil to each well to prevent evaporation, the plate was heated on the gradient block for 3 min. The contents of each well were then allowed to reach room temperature and transferred to a flat bottom microplate.

Figure 40:
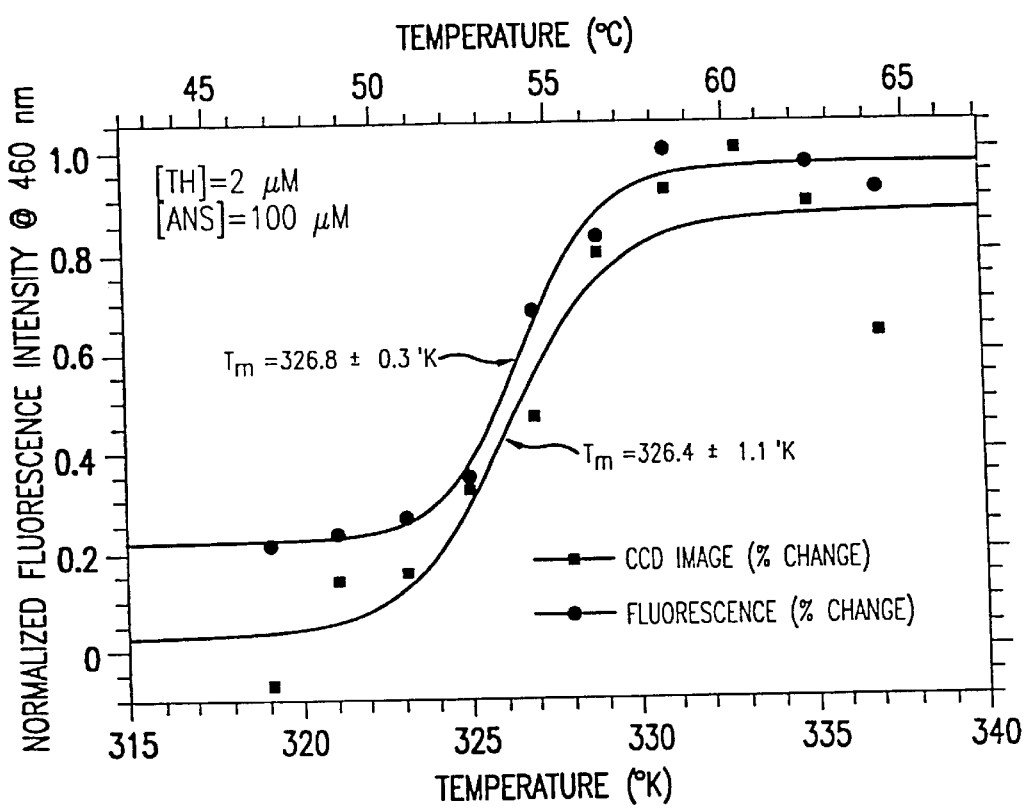
FIG. 40 shows a comparison of the results of microplate thermal shift assays of human α-thrombin denaturation performed using a fluorescence scanner and a CCD camera.

In this experiment, no filters were employed to narrow the excitatory wavelength to ~360 nm and the emission wavelength to ~460 nm, which are optimal wavelengths for the 1,8 ANS fluorophore. The flat bottom plate was then placed on the near UV transillumination box and the CCD camera was used to measure the amount of emitted light. The plate was also read using a conventional fluorescence plate reader (CytoFluor II), in order to compare the results obtained by the two different detection methods. The results for the two detection methods are plotted in FIG. 40. The results in FIG. 40 show that the CCD camera is useful as a fluorescence emission detector for monitoring the unfolding of a protein in the microplate thermal shift assay.

EXAMPLE 22

Microplate Thermal Shift Assay Using a Charge Coupled Device Camera

Figure 41A:
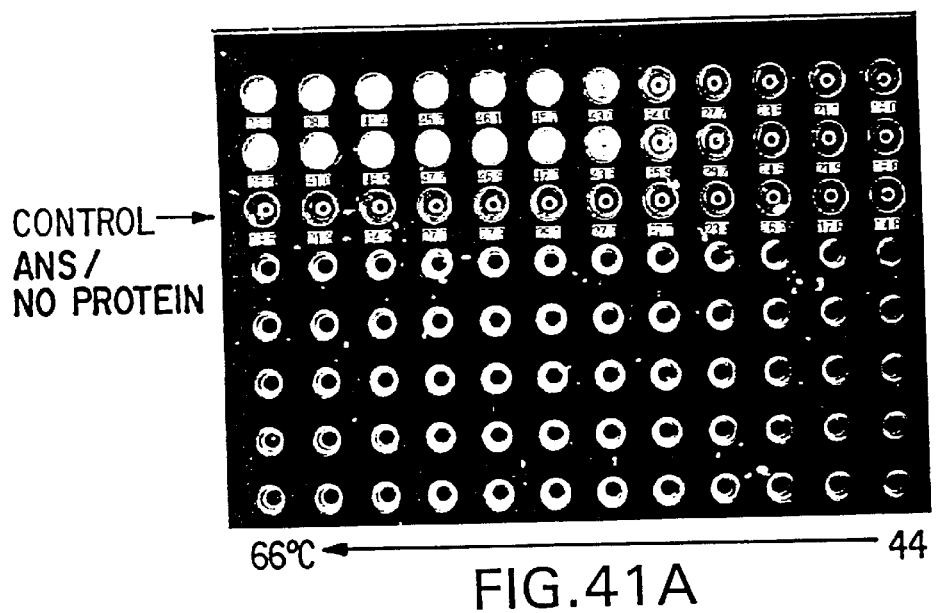
FIGS. 41A and 41B show photographs of microplate thermal shift assay of human α-thrombin denaturation performed using a CCD camera.
Figure 41B:
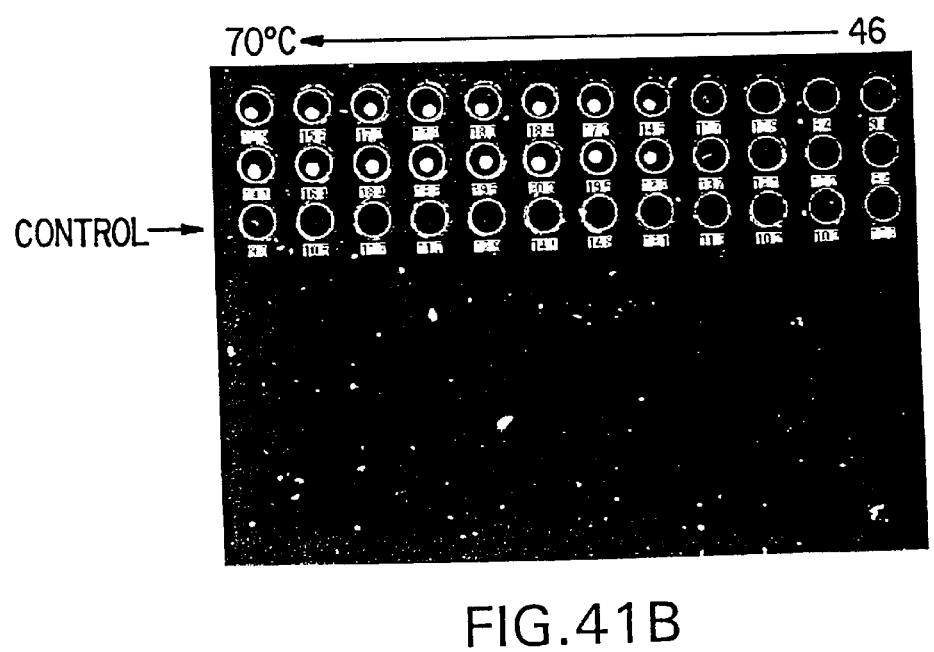
Figure 42:
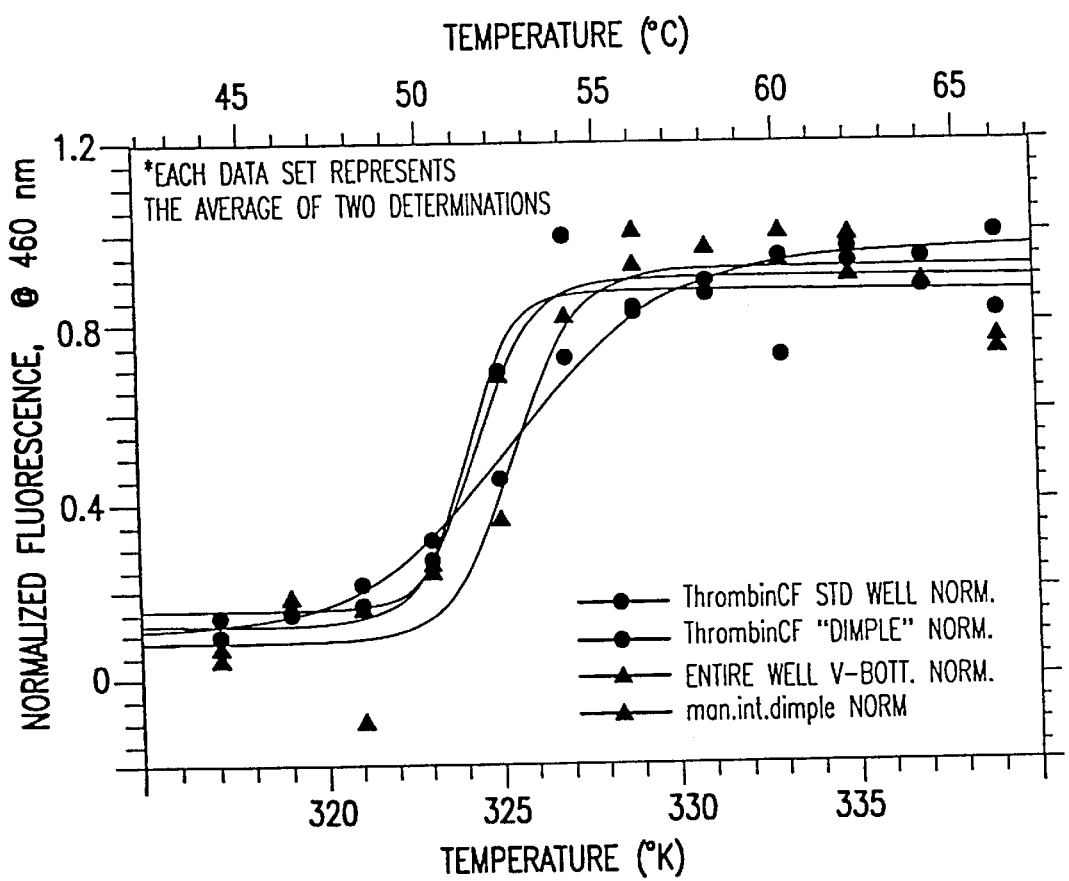
FIG. 42 shows a comparison of the results of microplate thermal shift assays of human α-thrombin denaturation performed using a fluorescence scanner and a CCD camera.

An emission filter was used to block out all stray light outside the region of the emission region for 1,8-ANS (~460 nm). In addition, the 5 $\mu$L miniaturized form of the microplate thermal shift assay was employed to test the CCD camera detection method in this configuration. Both the polycarbonate V-bottom and dimple plates were tested. The experiment was essentially the same as described in Example 21, except that the volume of the assay was 5 $\mu$L in either the V-bottom or dimple 96 well plates. The temperature range was 44 to 66° C. (right to left) for the V-bottom plate, and 46 to 70° C. (right to left) for the dimple plate. Photographs of the CCD images are shown in FIG. 41. The V-bottom well microplate image is shown in FIG. 41A. The dimple plate image is shown in FIG. 41B. The results obtained from the plate in FIG. 41A is shown in FIG. 42. The results in FIG. 42 show that data obtained using a CCD camera compare very well with data obtained using a fluorescence plate reader that employs a photo-multiplier tube (PMT) for fluorescence detection.

EXAMPLE 23

Figure 43A:
FIGS. 43A and 43B show a comparison of fluorescence background collected using a 435/550 nm bandpass (FIG. 43A), and a 475/550 nm bandpass.
Figure 43B:

Comparison of Fluorescence Background Due to Contaminants Collected Using Different Bandpass Filters An empty 384-well black polypropylene thermocycler plate (Matrix, Inc.) was imaged in an enclosed, black-walled metal box using two ultraviolet lamps (365 nm peak emission). The images were recorded using a charge-coupled device (CCD) camera (Cohu) equipped with optical filters. In FIG. 43A, data were collected using a long pass filter (435 cut-on wavelength) was combined with a short pass filter (550 nm cut-off-wavelength) to allow transmittance of light from 435 nm to 550 nm into the CCD camera. In FIG. 43B, data were collected using a long pass filter (475 cut-on wavelength) was combined with a short pass filter (550 nm cut-off wavelength) to allow transmittance of light from 475 nm to 550 nm into the CCD camera.

The images shown in FIGS. 43A and 43B were recorded using an empty, black plate. Therefore, anything present in the image other than the black background is due to unwanted background fluorescence or light scattering coming from contaminants on the surface of the plate (e.g. dust particles). FIG. 43A shows that the amount of background interference is much greater for the 435 longpass filter than for the 475 nm longpass filter (FIG. 43B). This illustrates the importance of imaging at longer wavelengths (greater than 475 nm), and the value of using a reporter dye molecule that emits as much light as possible at wavelengths greater than 475 nm.

EXAMPLE 24

Figure 44:
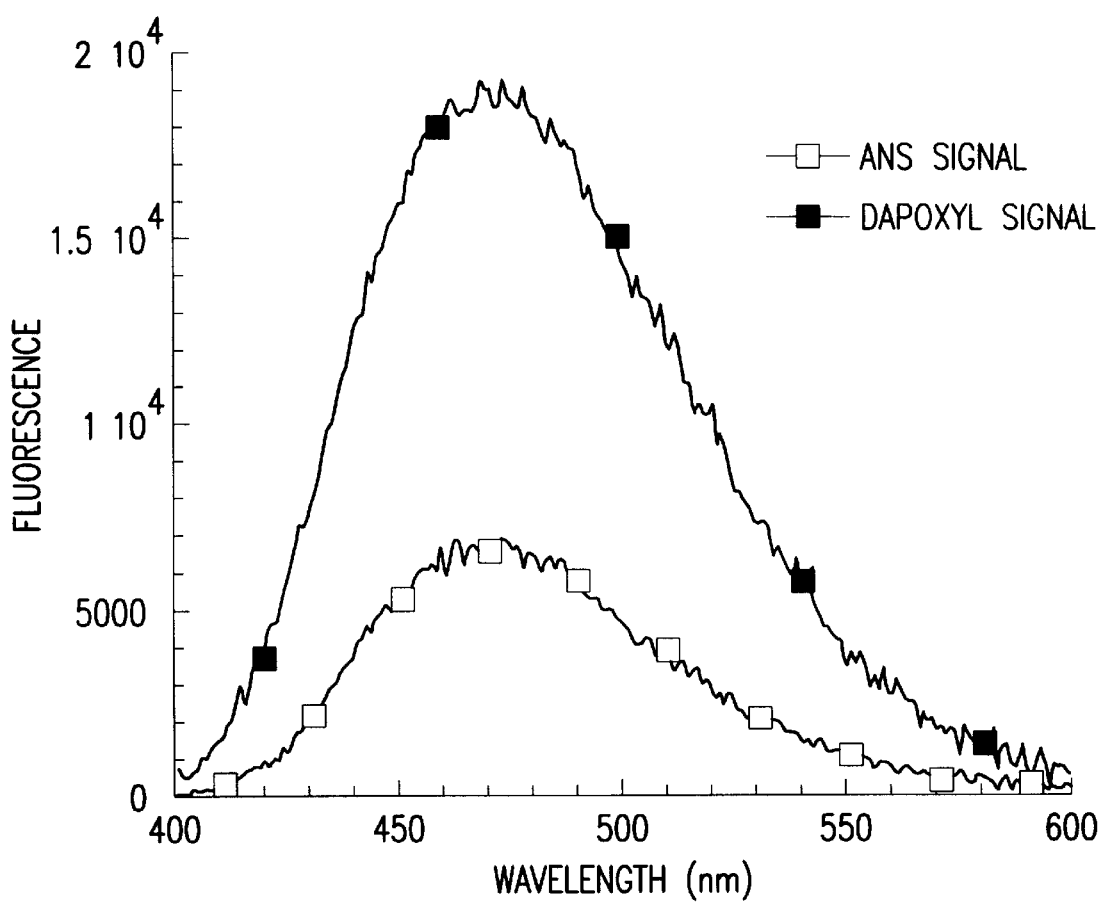
FIG. 44 shows the comparison of fluorescence signals for 1,8-ANS and 5-(4"-dimethylaminophenyl)-2-(4'-phenyl) oxazole sulfonate. The protein is chicken muscle pyruvate kinase.

Comparison of the Fluorescence Signals of 1-Anilinonaphthalene-8-Sulfonate and 5-(4'-dimethylaminophenyl)-2-(4'-phenyl)oxazole Sulfonate When Interacting to Unfolded Pyruvate Kinase A 0.2 mg/mL solution of chicken muscle pyruvate kinase (Sigma Chemical Co., catalog # P6406) was incubated with either 10 mM 1-anilinonaph-thalene-8-sulfonate (1,8-ANS) (FIG. 44, open squares) or 10 mM 5-(4"-dimethylaminophenyl)-2-(4'-phenyl)oxazole sulfonate (Molecular Probes catalogue no. D-12800) (FIG. 44, closed squares) in a 500 μL four-sided quartz cuvette. Fluorescence spectra were recorded using a spectrofluorimeter (Florolog, SPEX/ISA), with the excitation monochromator set to 370 nm, and the excitation and emission bandpass slit widths set at 1 nm, The instrument was operated in front-face collection mode, so that fluorescence was collected from the same face of the cuvette that was illuminated by the exciting light source. Emission spectra of native protein+dye were recorded after mixing the protein and dye solutions at room temperature. Emission spectra of denatured protein and fluorescence dye were recorded after the protein/dye solutions were heated to 75° C. for 2 minutes, and then cooled to room temperature immediately prior to data collection. The spectra shown in FIG. 44 are difference spectra that were calculated by subtracting the native protein fluorescence from the denatured protein fluorescence for each dye at 25° C. These difference spectra represent the dependence of the fluorescence signal at the emission wavelength for each reporter dye, and show the increase in fluorescence signal upon the thermal unfolding of pyruvate kinase.

This example illustrates that at wavelengths above 480 nm, 5-(4"-dimethylaminophenyl)-2-(4'-phenyl)oxazole sulfonate emits an approximately 3.2-fold higher fluorescence signal than 1,8-ANS, when pyruvate kinase is converted from the folded form to the unfolded form.

EXAMPLE 25

Figure 45A:
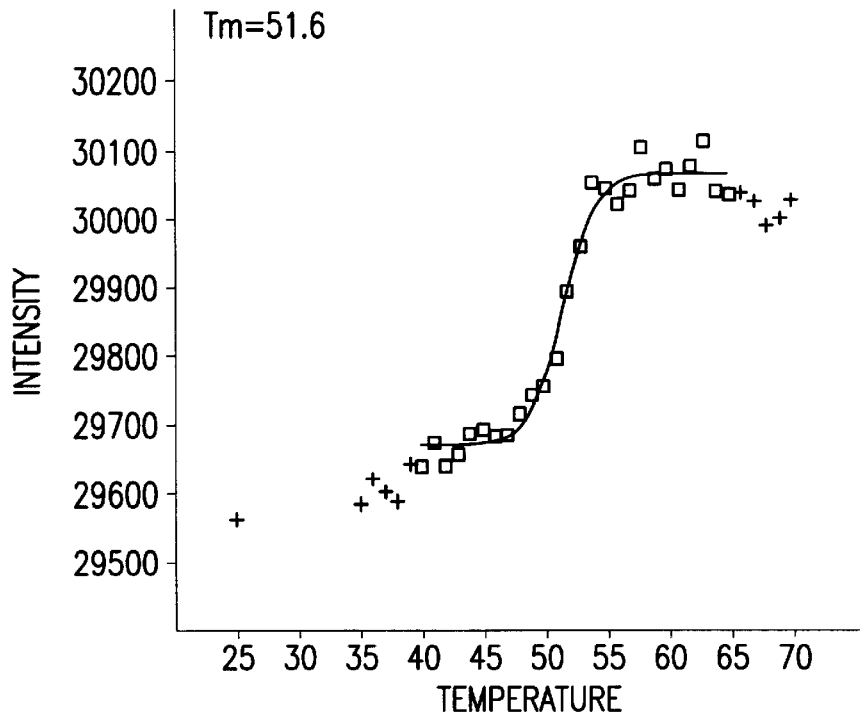
FIGS. 45A and 45B show the results of a bandpass study using 1,8-ANS (FIG. 45A) and 5-(4"-dimethylaminophenyl)-2-(4'-phenyl)oxazole sulfonate (FIG. 45B).
Figure 45B:
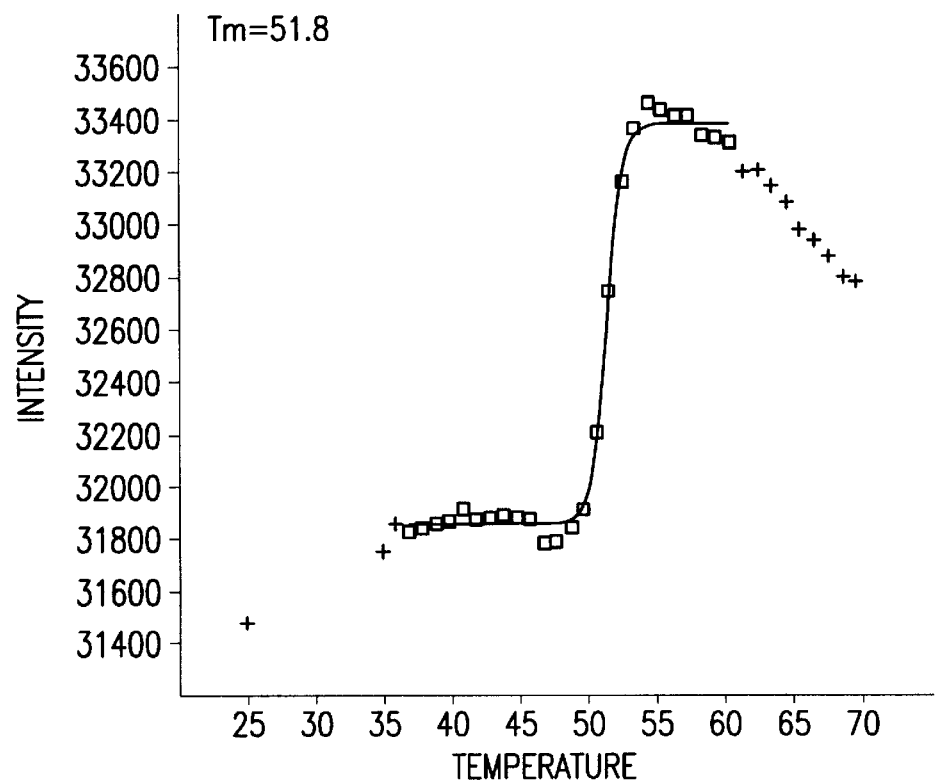

Comparison of Fluorescence Signals Generated Using 1,8-ANS and 5-(4"-dimethylaminophenyl)-2-(4'-phenyl)oxazole Sulfonate for Human Thrombin Protein in a Multi- Well Thermal Unfolding Study A 1 μM thrombin solution was mixed with 5-(4"-dimethylaminophenyl)-2-(4'-phenyl)oxazole sulfonate dye to yield a final concentration of 100 μM 5-(4"-dimethylaminophenyl)-2-(4'-phenyl)oxazole sulfonate. This solution was pipetted into all the wells of a 384-well black thermocycler plate with a final volume of 4 μL per well, and 3 μL of mineral oil was then added to each well. The fluorescence signal from each well was recorded in a closed, black-walld metal box using a cooled CCD camera (SenSys, Photometrix, Inc.) equipped with a 500+/−25 nm bandpass filter. An identical experiment was performed separately, using the same instrument, camera, and filters, except that a final concentration of 100 μM 1,8-ANS was used in place of 5-(4"-dimethylaminophenyl)-2-(4'-phenyl)oxazole sulfonate as the reporter dye. As shown in FIGS. 45A and 45B, the fluorescence signal deflection obtained using 5-(4"-dimethylaminophenyl)-2-(4'-phenyl)oxazole sulfonate (FIG. 45B) was significantly larger than the signal obtained using 1,8 ANS as the reporter dye molecule (FIG. 45A).

The ratio of signals from 5-(4"-dimethylaminophenyl)-2-(4'-phenyl)oxazole sulfonate and 1,8-ANS was calculated by averaging the signals of all 384 wells on each plate, and dividing the average signal from 1,8-ANS into that for 5-(4"-dimethylaminophenyl)-2-(4'-phenyl)oxazole sulfonate. 5-(4"-dimethylaminophenyl)-2-(4'-phenyl)oxazole sulfonate was found to generate 4.25 times more signal than 1,8-ANS. Thus, 5-(4"-dimethylaminophenyl)-2-(4'-phenyl) oxazole sulfonate yields substantially more signal than 1,8-ANS, under the conditions employed, showing that 5-(4"-dimethylaminophenyl)-2-(4'-phenyl)oxazole sulfonate is superior to 1,8-ANS for practicing the thermal unfolding screening assays in the optimal wavelength range.

EXAMPLE 26

Utility of 5-(4"-dimethylaminophenyl)-2-(4'-phenyl) oxazole Dyes In Measuring Thermal Midpoint Transition Ttemperatures For Many Different Classes of Proteins It has been found that the fluorescence emission of 5-(4"-dimethylaminophenyl)-2-(4'-phenyl)oxazole sulfonate can be used to collect thermal unfolding data for many different types of proteins, proteins that encompass a wide range of biological functions. Shown in Table 10 are the midpoint transition temperatures from fluorescence thermal shift assays performed using nine different proteins that vary widely in their sizes, stabilities, and biological activities. Thermal shift assays were performed as follows: 10 μL of each reaction mixture was dispensed into a single well of a 384-well polypropylene thermocycler plate, and either 5 μL or 10 μL of mineral oil was added to the top of the mixture (overlaid). Data were recorded at multiple temperatures separated by 1 degree intervals over different temperature ranges.

For each unfolding study, thermal transitions were measured by heating the samples at each temperature for 3 minutes, followed by incubation at 25° C. for 1 minute, followed by illumination using a UV light source with peak output at 365 mm. During illumination, fluorescence from the 5-(4"-dimethylaminophenyl)-2-(4'-phenyl)oxazole sulfonate was recorded using a CCD camera equipped with a 500 nm bandpass filter. In all experiments, the concentration of 5-(4"-dimethylaminophenyl)-2-(4'-phenyl) oxazole sulfonate was 100 μM.

In the order:they are presented in Table 10, the assay conditions were as follows: human mdm2, 12 kDa fragment (residues 17–127):0.084 mg/mL protein, 50 mM HEPES, 150 mM NaCl, pH 7.5, 3 mM glutathione (reduced form), temperature range: 30–50° C., measured in 1.5 degree increments; human plasminogen activator inhibitor 1:0.05 mg/mL protein, 50 mM sodium phosphate pH 7.0, 150 mM NaCl, pH 7.5, temperature range: 30–60° C., measured in 1.0 degree increments; bovine liver dihydrofolate reductase: 0.2 mg/mL protein, 50 mM HEPES, 100 mM NaCl, pH 7.5, temperature range: 30–90° C., measured in 1.0 degree increments; human basic fibroblast growth factor: 4 μM protein, 45 mM HEPES pH 7.5, 88 mM NaCl, temperature range: 35–99° C., measured in 1.0 degree increments; the D2/D3 fragment of human basic fibroblast growth factor receptor 1:24 μM protein, 1× phosphate buffered saline (Gibco), 40 mM sodium citrate, 2% plycerol, 10 mM magnesium chloride, temperature range: 30–84° C., measured in 2.0 degree increments; human alpha estrogen receptor: 0.9 μM protein, 50 mM Tris pH 8, 0.25 mM KCL, 5% glycerol, 1 mM EDTA, 2 mM dithiothreitol, 1 mM sodium vanadate, 10 mM magnesium chloride, temperature range: 30–75° C., measured in 1.0 degree increments; for Halobacterium halobium bacteriorhodopsin: 5 μM protein, 5 mM sodium acetate pH 5.0, 6.5 mM nonyl-β-glucopyranoside, temperature range: 30–95° C., measured in 1.0 degree increments; bovine muscle myosin: 0.5 mg/mL protein, 50 mM HEPES, 100 mM NaCl, pH 7.5, temperature range: 30–90° C., measured in 1.0 degree increments; for chicken muscle pyruvate kinase: 0.5 mg/mL, protein, 50 mM HEPES, pH 7.5, 100 mM NaCl, temperature range: 30–90° C., measured in 1.0 degree increments.

TABLE 10

Transition midpoint temperatures for different proteins, measured using 5-(4"-dimethylaminophenyl)-2-(4'-phenyl)oxazole sulfonate.

| Protein | $T_m$(° C.) |
|---|---|
| Human mdm2, 12 kDa fragment (residues 17–127) | 65.5 |
| Human plasminogen activator inhibitor 1 | 47.6 |
| Bovine liver dihydrofolate reductase | 52.5 |
| Human basic fibroblast growth factor | 48.5 |
| Human basic fibroblast growth factor receptor, D2/D3 fragment | 59.0 |
| Human alpha estrogen receptor | 46.0 |
| *Halobacterium halobium* bacteriorhodopsin | 73.4 |
| Bovine muscle myosin | 49.4 |
| Chicken muscle pyruvate kinase | 54.5 |

What is claimed is:

1. A method for ranking the affinity of each of a multiplicity of different molecules for a target molecule which is capable of unfolding due to a thermal change, said method comprising
   (a) contacting the target molecule with one molecule of a multiplicity of different molecules, in the presence of a 5-(4"-dimethylaminophenyl)-2-(4'-phenyl)oxazole derivative dye, in each of a multiplicity of containers;
   (b) simultaneously heating said multiplicity of containers;
   (c) measuring the fluorescence in each of said containers;
   (d) generating thermal unfolding information for the target molecule as a function of temperature for each of said containers;
   (e) comparing the thermal unfolding information obtained for each of said containers to (i) the thermal unfolding information obtained for each of the other containers, and (ii) the thermal unfolding information obtained for the target molecule in the absence of any of said molecules in said multiplicity of different molecules; and
   (f) ranking the affinities of each of said molecules according to the difference in said thermal unfolding information between the target molecule in each of said containers and the target molecule in the absence of any of said molecules in the multiplicity of different molecules.

2. The method of claim 1, wherein said thermal unfolding information is the thermal unfolding $T_m$.

3. The method of claim 1, wherein said target molecule is a protein.

4. The method of claim 1, wherein said multiplicity of different molecules comprises a combinatorial library.

5. The method of claim 1, wherein said fluorescence in each of said containers is measured simultaneously.

6. The method of claim 1, wherein said heating, said measuring, said generating, and said comparing are performed automatically.

7. The method of claim 6, wherein said contacting is performed automatically.

8. The method of claim 6, wherein said ranking is performed automatically.

9. The method of claim 6, wherein said method is high-throughput.

10. The method of claim 1, wherein said 5-(4"-dimethylaminophenyl)-2-(4'-phenyl)oxazole derivative dye is selected from the group consisting of 5-(4"-dimethylaminophenyl)-2-(4'-phenyl)oxazole butylsulfonamide, or a salt or ester thereof; 5-(4"-dimethylaminophenyl)-2-(4'-phenyl)oxazole-(2-aminoethyl)sulfonamide, or a salt or ester thereof; 5-(4"-dimethylaminophenyl)-2-(4'-phenyl)oxazole-3-sulfonamidophyenylboronic acid, or a salt or ester thereof; 5-(4"-dimethylaminophenyl)-2-(4'-phenyl)oxazole sulfonic acid, or a salt or ester thereof, 5-(4"-dimethylaminophenyl)-2-(4'-phenyl)oxazole sulfonyl hydrazine, 5-(4"-dimethylaminophenyl)-2-(4'-phenyl)oxazole-(2-bromoacetamidoethyl)sulfonamide, or a salt or ester thereof; 5-(4"-dimethylaminophenyl)-2-(4'-phenyl)oxazole-2-(3-(2-pyridyldithio) propionamidoethyl)sulfonamide, or a salt or ester thereof; 5-(4"-dimethylaminophenyl)-2-(4'-phenyl) oxazole sulfonyl chloride, or a salt or ester thereof; 5-(4"-dimethylaminophenyl)-2-(4'-phenyl)oxazole-3-sulfonamidopropionic acid, or a salt or ester thereof, 5-(4"-dimethylaminophenyl)-2-(4'-phenyl)oxazole carboxylic acid, or a salt or ester thereof, and 5-(4"-dimethylaminophenyl)-2-(4'-phenyl)oxazole sulfonate, or a salt or ester thereof.

11. The method of claim 10, wherein said 5-(4"-dimethylaminophenyl)-2-(4'-phenyl)oxazole derivative dye is 5-(4"-dimethylaminophenyl)-2-(4'-phenyl)oxazole sulfonate, or a salt or ester thereof.

12. The method of claim 11, wherein said 5-(4"-dimethylaminophenyl)-2-(4'-phenyl)oxazole derivative dye is 5-(4"-dimethylaminophenyl)-2-(4'-phenyl)oxazole sulfonate, sodium salt.

* * * * *